United States Patent
Bachmann et al.

(10) Patent No.: US 10,494,527 B2
(45) Date of Patent: Dec. 3, 2019

(54) CATIONIC DIRECT DYES

(71) Applicant: BASF SE, Ludwigshafen (DE)

(72) Inventors: Frank Bachmann, Freiburg (DE);
Christian Cremer, Loerrach (DE);
Beate Froehling, Neustadt (DE); Bryan Patrick Murphy, Cincinnati, OH (US);
Guiru Zhang, Cincinnati, OH (US);
Peter Marte Torgerson, Washington Courthouse, OH (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/557,594

(22) PCT Filed: Mar. 18, 2016

(86) PCT No.: PCT/EP2016/055958
§ 371 (c)(1),
(2) Date: Sep. 12, 2017

(87) PCT Pub. No.: WO2016/146813
PCT Pub. Date: Sep. 22, 2016

(65) Prior Publication Data
US 2018/0244924 A1 Aug. 30, 2018

(30) Foreign Application Priority Data
Mar. 19, 2015 (EP) .................................... 15159861

(51) Int. Cl.
| | | |
|---|---|---|
| *C09B 44/16* | (2006.01) | |
| *C09B 44/20* | (2006.01) | |
| *C09B 44/08* | (2006.01) | |
| *A61Q 5/06* | (2006.01) | |
| *A61K 8/49* | (2006.01) | |
| *A61Q 5/10* | (2006.01) | |
| *C09B 23/10* | (2006.01) | |
| *C09B 44/12* | (2006.01) | |
| *C09B 55/00* | (2006.01) | |
| *C09B 56/12* | (2006.01) | |

(52) U.S. Cl.
CPC .............. *C09B 44/16* (2013.01); *A61K 8/49* (2013.01); *A61K 8/4926* (2013.01); *A61K 8/4946* (2013.01); *A61Q 5/065* (2013.01); *A61Q 5/10* (2013.01); *C09B 23/105* (2013.01); *C09B 44/08* (2013.01); *C09B 44/126* (2013.01); *C09B 44/20* (2013.01); *C09B 55/003* (2013.01); *C09B 56/12* (2013.01); *A61K 2800/4322* (2013.01); *A61K 2800/4324* (2013.01)

(58) Field of Classification Search
USPC ..................................................... 548/331.5
See application file for complete search history.

(56) References Cited

U.S. PATENT DOCUMENTS

| | | | |
|---|---|---|---|
| 2009/0126755 A1 | 5/2009 | Guerin et al. | |
| 2010/0011518 A1* | 1/2010 | Cremer | A61K 8/49 8/426 |
| 2016/0271041 A1* | 9/2016 | Zhang | A61Q 5/10 |

FOREIGN PATENT DOCUMENTS

| | | | | |
|---|---|---|---|---|
| EP | 2 018 847 | A1 | 1/2009 | |
| FR | 2912143 | A1 | 8/2008 | |
| FR | 2921379 | A1 | 3/2009 | |
| WO | WO-2006/136617 | A2 | 12/2006 | |
| WO | WO-2007/025889 | A2 | 3/2007 | |
| WO | WO-2007/039527 | A2 | 4/2007 | |
| WO | WO-2007144280 | A2 * | 12/2007 | .............. A61K 8/49 |
| WO | WO-2008/019977 | A2 | 2/2008 | |
| WO | WO-2009/009121 | A1 | 1/2009 | |
| WO | WO-2009/037325 | A2 | 3/2009 | |
| WO | WO-2009/090125 | A1 | 7/2009 | |
| WO | WO-2012/113722 | A2 | 8/2012 | |
| WO | WO-2012/113725 | A2 | 8/2012 | |
| WO | WO-2012113722 | A2 * | 8/2012 | .......... A61K 8/4926 |
| WO | WO-2012/150549 | A1 | 11/2012 | |
| WO | WO-2013/046041 | A1 | 4/2013 | |

OTHER PUBLICATIONS

Bergeron, R.J., et al, "Reagents for the Selective Acylation of Spermidine, Homospermidine, and Bis [3-aminopropyl]-amine," *Synthesis*, 1981, Vol., pp. 732-733.
Bergeron, R.J., et al., "Reagents for the Selective Secondary N-acylation of Linear Triamines," *Synthesis*, 1982, vol. 8, pp. 689-692.
Covassin, L., et al, "Xylylated Dimers of Putrescine and Polyamines: Influence of the Polyamine Backbone on Spermidine Transport Inhibition," *Bioorganic & Medicinal Chemistry Letters*, 2003, vol. 13, No. 19, pp. 3267-3271.
Extended European Search Report for Ep Patent Application No. 15159861.2, dated Sep. 29, 2015 (12 pages).
Marsh, I.R., et al. "Solid Phase Synthesis of Polyamine Conjugates for the Study of Trypanothione Reductase," *Tetrahedron*, 1997,vol. 53, No. 51, pp. 17317-17334.
(Continued)

*Primary Examiner* — Kamal A Saeed
(74) *Attorney, Agent, or Firm* — Marshall, Gerstein & Borun LLP

(57) ABSTRACT

The invention relates to cationic direct dyes of the formula I (1), wherein m and n are independently from each other 0 or 1, D is an aromatic or a cationic heteroaromatic group, which are further specified, K is an aromatic or heteroaromatic group, $E_1$ and $E_2$ are independently from each other =CH— or =N—, An is an anion and a is a number from 1 to 6 and $R_1$ and $R_2$ are independently from each other and further specified. The compounds show washfastness at hair-dying.

(1)

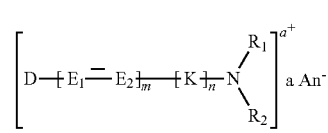

7 Claims, No Drawings

(56) References Cited

OTHER PUBLICATIONS

Patil, K.M., et al., Second Generation, Arginine-Rich (R-X'-R) 4-Type Cell-Penetrating α-ω-α-Peptides with Constrained, Chiral ω-amino acids (X') for Enhanced Cargo Delivery Into Cells, *Bioorganic & Medicinal Chemistry Letters*, 2014, vol. 24, No. pp. 4198-4202.
Peor, N., et al., "Variable Density Effect of Self-Assembled Polarizable Monolayers on the Electronic Properties of Silicon," *Journal of the American Chemical Society*, 2008, vol. 130, No. 12, pp. 4158-4165.
Taylor, E.C., et al., "Conversion of a Primary Amino Group Into a Nitroso Group," *Synthesis of Nitroso-Substituted Heterocycles, The Journal of Organic Chemistry*, 1982, vol. 47, No. 3, pp. 552-555.
Written Opinion for PCT Patent Application No. PCT/EP2016/055958, dated Aug. 29, 2016 (12 pages).
International Search Report for Patent Application No. PCT/EP2016/055958, dated Aug. 29, 2016.

* cited by examiner

CATIONIC DIRECT DYES

CROSS-REFERENCE TO RELATED APPLICATIONS

This application is the U.S. National Stage application of International Patent Application No. PCT/EP2016/055958, filed Mar. 18, 2016, which claims the benefit of European Patent Application No. 15159861.2, filed Mar. 19, 2015.

The present invention relates to washfast and acid perspiration resistant direct dye compounds. The direct dye compounds each have one or two permanent cations, one to four incipient cations, and optionally one or more C5-C9 hydrophobic moieties.

BACKGROUND OF THE INVENTION

In general, direct dye products last only 6-10 shampoos and are hence known as semi-permanent. However, many consumers want more permanent results, and therefore default to oxidative dye products that contain hydrogen peroxide or other oxidants. The direct dye compounds and the method described herein can be used in either direct dye or oxidation dye products.

The permanent alteration of the color of keratinous fibers, in particular human hair, by the application of hair dyes is well known. In order to provide the consumer with the shade, longevity, and the intensity of color desired, an oxidative coloring process involving complex chemical reactions is utilized. Permanent hair dyeing formulations typically comprise primary intermediates (also known as oxidative hair dye precursors or developers) and couplers (also known as color modifiers or secondary intermediates). These dye precursors are sufficiently small, polar and soluble to diffuse into the hair shaft where, once activated by an oxidizing agent under basic conditions, such as hydrogen peroxide, the primary intermediates react with other dye precursors, e.g., couplers, to form larger colored chromophores in the hair shaft. The chromophores formed in the hair shaft do not readily diffuse out of the hair during subsequent washing with water and/or detergents because they are bigger, less polar and soluble than dye precursors that diffused in.

Hair colorant products are typically sold in the form of kits containing a dye component (e.g., a dye solution) and an oxidizing component (e.g., a hydrogen peroxide solution). In use, the dye component is mixed with the oxidizing component and the resultant mixture is applied to hair. When the two components are mixed, oxidizing agents present in the oxidizing component begins to oxidize primary intermediates present in the dye component and the oxidized primary intermediates begin to react with couplers to form chromophores. Since coloring hair is one of the beauty routines, it is highly desirable that the dyeing process, excluding bleaching, be rather a physical process, which would allow it to be aligned with many other beauty routines such as applying lip color and facial touchups. The challenge is to still meet all of the other requirements of hair color (e.g., washfastness, little or no bleeding of color from the hair when it is wet, no skin staining, evenness, and resistance to acid perspiration).

Many attempts have been made by the hair color industry to enhance the washfastness of direct dyes by either forming a covalent bond between chromophore and proteins inside hair or increasing the number of binding sites, typically cationic centers, on the chromophore. However, each attempt has its drawbacks. The approach through covalent bonding does not differentiate proteins in hair from skin. The approach through multiple binding sites on the dyes (i.e. multiple positive charges to interact with negative sites on hair, either by bonding several monocationic 10 dyes together or by installing multiple cationic centers on a single chromophore) runs into the obstacles of uneven color due to uneven damage (negative charges) along the length of the hair fibers and reduced dye penetration into hair fibers because the dyes are typically at least twice as large as common oxidative dye precursors. An increase in the number of binding sites minimizes bleeding and color loss caused by rinsing by providing stronger hair-chromophore interactions. However, the same strong binding force to the cuticle also prevents the chromophores from penetrating deep into the cortex of hair, because it is difficult for dyes with multiple positive charges to diffuse through negatively charged networks of keratin proteins. Additionally, since polycationic dyes remain bound to the hair surface rather than penetrating into the fiber, it's difficult to produce dark shades due to limited binding sites on the surface of hair.

Conventional cationic direct dyes do not have much resistance to acid perspiration as they undergo a natural ion exchange process where the cations in human sweat (mainly protons and sodium ions) replace the cationic dyes that are deposited on hair. Even washfast cationic dyes with multiple cationic anchoring groups have little resistance against a low pH saline solution.

The present invention refers to hair dye compounds of formula

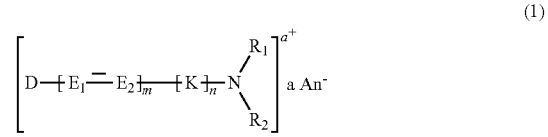

wherein
D is an aromatic or a cationic heteroaromatic group selected from
the radicals of formula

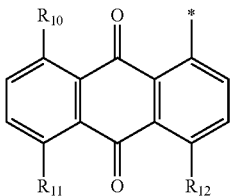

(1e)

K is an aromatic or heteroaromatic group;

$R_1$ and $R_2$ independently from each other are hydrogen; $C_1$-$C_{12}$alkyl; $C_1$-$C_{12}$alkyl, which is substituted by hydroxy; $N^+(R_3R_4R_5)$—$C_1$-$C_{12}$alkyl; amino-$C_6$-$C_{10}$aryl; $N(R_6R_7)$—$C_1$-$C_8$alkyl; $N(R_6R_7)$—$C_1$-$C_{12}$alkyl, which is substituted by hydroxy or interrupted by —$NR_9$—; $C_6$-$C_{10}$aryl; or $R_1$ and $R_2$ together with the linking nitrogen atom form a 5- to 7-membered heterocyclic ring comprising at least two nitrogen atoms;

$R_3$, $R_4$, $R_5$, $R_6$, $R_7$ and $R_9$, independently from each other are hydrogen; $C_1$-$C_5$alkyl; amino-$C_1$-$C_5$alkyl; $C_1$-$C_5$alkylamino-$C_1$-$C_5$alkyl; or di-$C_1$-$C_5$alkylamino-$C_1$-$C_5$alkyl;

$R_{10}$, $R_{11}$ and $R_{12}$ independently from each other are hydrogen; $C_1$-$C_{12}$alkyl; $N(R_{13}R_{14})$—$C_1$-$C_{12}$alkyl; $N(R_{13}R_{14})$—$C_1$-$C_{12}$alkyl which is interrupted by phenylene; $N^+(R_{13}R_{14}R_{15})$—$C_1$-$C_{12}$alkyl which is interrupted by phenylene;

$R_{13}$, $R_{14}$, $R_{15}$ independently from each other are hydrogen; $C_1$-$C_5$alkyl; amino-$C_1$-$C_5$alkyl; $C_1$-$C_5$alkylamino-$C_1$-$C_5$alkyl; or di-$C_1$-$C_5$alkylamino-$C_1$-$C_5$alkyl;

$E_1$ and $E_2$ independently from each other are =CH—; or =N—;

An is an anion a is a number from 1 to 6;

m and n independently from each other are 0; or 1;

if D is a radical of formula (1a), (1b) or (1e), at least one of the radicals $R_1$, $R_2$, $R_{10}$, $R_{11}$ and $R_{12}$ is substituted by radical comprising at least one amino group;

if D is a radical of formula (1c) or (1d), at least one of the radicals $R_1$ and $R_2$ is substituted by at least one amino-substituted radical; and wherein the compounds of formula (1) comprise one to four incipient cations, wherein the incipient cations are pendant to the core structure, and wherein the incipient cations are neutral and comprise optionally one or more $C_5$-$C_9$ hydrophobic moieties $C_1$-$C_{14}$alkyl are straight chain or branched alkyl radicals like methyl, ethyl, n-propyl, isopropyl, n-butyl, sec.butyl, tert.butyl, amyl, isoamyl or tert.amyl, hexyl, 2-ethylhexyl, heptyl, octyl, isooctyl, nonyl, decyl, undecyl, dodecyl or tetradecyl.

$C_6$-$C_{10}$aryl is for example naphthyl or phenyl, which are optionally substituted by one or more hydroxy, amino, halogen or $C_1$-$C_5$alkyl.

Aromatic groups are coplanar structured rings of atoms containing a number of double bonds in form of a delocalized conjugated π system, most commonly an arrangement of alternating single and double bonds. Most preferred representatives are benzene and its derivatives, benzoquinones, naphthaline and athracene.

In heterocyclic aromatic groups (heteroaromats), one or more of the carbon atoms in the aromatic ring is replaced by the heteroatoms oxygen, nitrogen, or sulfur like pyridine, pyrazine, imidazole, oxazole, thiophene, and their benzannulated analogs like benzimidazole. Most preferred heterocyclic groups comprise one, two or three, preferably one or two identical or different hetero atoms. The heterocyclic groups may be mono- or polycyclic, for example mono-, bi- or tricyclic. Preferably, they are mono- or bicyclic, mot preferably monocyclic. The rings preferably comprise 5, 6 or 7 ring members. Examples for monocyclic and bicyclic heterocyclic systems are for example pyrrol, furan, thiophene, imidazole, pyrazole, 1,2,3-triazole, 1,2,4-triazole, pyridine, Pyridazine, pyrimidine, pyrazine, pyrane, thiopyrane, 1,4-dioxane, 1,2-oxazine, 1,3-oxazine, 1,4-oxazine, indol, benzothiophene, benzofurane, pyrrolidine, piperidine, piperazine, morpholine and thiomorpholine.

Preferred compounds of the present invention are those representatives, wherein D in formula (1) is selected from the radicals of formula

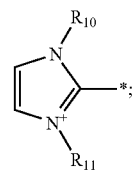

(1a)

wherein $R_{10}$ and $R_{11}$ independently from each other are $C_1$-$C_{12}$alkyl; amino-$C_1$-$C_{12}$alkyl; di-$C_1$-$C_5$alkylamino-$C_1$-$C_{12}$alkyl; or $N^+(R_3R_4R_5)$—$C_1$-$C_{12}$alkyl; and.

$R_3$, $R_4$ and $R_5$ are defined as in formula (1).

More preferred compounds according to the present invention correspond do formula

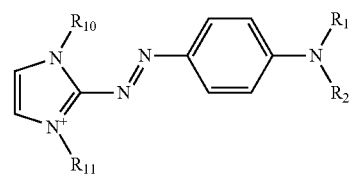

(2)

wherein $R_1$ and $R_2$ independently from each other are hydrogen; $C_1$-$C_{12}$alkyl; $C_1$-$C_{12}$alkyl, which is substituted by hydroxy; $N^+(R_6R_7R_8)$—$C_1$-$C_8$alkyl; amino-$C_6$-$C_{10}$aryl; $N(R_6R_7)$—$C_1$-$C_8$alkyl; $N(R_6R_7)$—$C_1$-$C_8$alkyl, which is interrupted by —$NR_9$—;

$R_{10}$ and $R_{11}$ independently from each other are $C_1$-$C_{12}$alkyl; $C_1$-$C_{12}$alkyl which is substituted by hydroxy or interrupted by phenylene; amino-$C_1$-$C_{12}$alkyl; di-$C_1$-$C_5$alkylamino-$C_1$-$C_{12}$alkyl; or $N^+(R_3R_4R_5)$—$C_1$-$C_{12}$alkyl;

An is an anion; and $R_3$, $R_4$, $R_5$, $R_6$, $R_7$, $R_8$ and $R_9$ independently from each other are hydrogen; $C_1$-$C_5$alkyl; amino-$C_1$-$C_5$alkyl; $C_1$-$C_5$alkylamino-$C_1$-$C_5$alkyl; or di-$C_1$-$C_5$alkylamino-$C_1$-$C_5$alkyl.

Most preferred are compounds of formula (2), wherein $R_1$ and $R_2$ independently from each other are $C_1$-$C_{12}$alkyl; or $N^+(R_6R_7R_8)$—$C_1$-$C_{12}$alkyl;

$R_6$, $R_7$, $R_8$, independently from each other are hydrogen; or $C_1$-$C_6$alkyl;

$R_{10}$ and $R_{11}$ independently from each other are $C_1$-$C_{12}$alkyl; or $N^+(R_3R_4R_5)$—$C_1$-$C_{12}$alkyl; and $R_3$, $R_4$ and $R_5$ independently from each other are hydrogen; or $C_1$-$C_5$alkyl.

Even more preferred are compounds of formula (2), wherein $R_1$ and $R_2$ are hydrogen; or $C_1$-$C_5$alkyl which is optionally substituted by $N^+(R_6R_7R_8)$;

$R_6$, $R_7$, $R_8$, independently from each other are hydrogen; or $C_1$-$C_5$alkyl; and $R_{10}$ and $R_{11}$ are $C_1$-$C_5$alkyl; $N^+(R_3R_4R_5)$—$C_1$-$C_5$alkyl; or $N(R_3R_4)$—$C_1$-$C_5$alkyl; and $R_3$, $R_4$ and $R_5$ independently from each other are hydrogen; or $C_1$-$C_5$alkyl.

Further preferred compounds of the present invention are those representatives, wherein D in formula (1) corresponds to formula

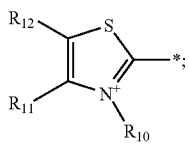

(1b)

wherein $R_{10}$, $R_{11}$, $R_{12}$ independently from each other are hydrogen; $C_1$-$C_5$alkyl; or amino-$C_1$-$C_5$alkyl.

More preferred representative compounds of the present invention correspond to formula

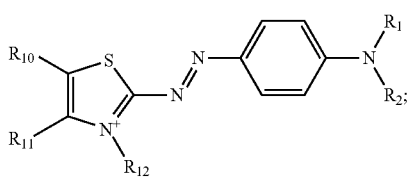

(3)

wherein $R_1$ and $R_2$ independently from each other are $C_1$-$C_{12}$alkyl; $N^+(R_6R_7R_8)$—$C_1$-$C_8$alkyl; amino-$C_6$-$C_{10}$aryl; or $N(R_6R_7)$—$C_1$-$C_8$alkyl;

$R_6$, $R_7$ and $R_8$ independently from each other are hydrogen; or $C_1$-$C_5$alkyl; and $R_{10}$, $R_{11}$, $R_{12}$ independently from each other are hydrogen; $C_1$-$C_5$alkyl; or amino-$C_1$-$C_5$alkyl.

Even more preferred are compounds of formula (3), wherein $R_1$ and $R_2$ independently from each other are $C_1$-$C_{12}$alkyl; and $R_{10}$, $R_{11}$ and $R_{12}$ independently from each other are $C_1$-$C_5$alkyl; or amino-$C_1$-$C_5$alkyl.

Further preferred compounds of the present invention are those representatives, wherein D in formula (1) corresponds to formula

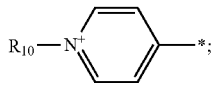

(1c)

wherein $R_{10}$ is hydrogen; $C_1$-$C_{12}$alkyl; or amino-$C_1$-$C_5$alkyl; or $N^+(R_3R_4R_5)$—$C_1$-$C_{12}$alkyl; wherein $R_3$, $R_4$ and $R_5$ independently from each other are hydrogen; or $C_1$-$C_5$alkyl.

More preferred representatives of the present invention correspond to formula

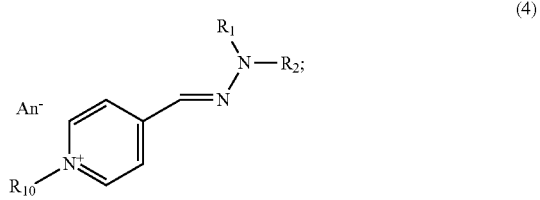

(4)

wherein $R_1$ and $R_2$ independently from each other are hydrogen; $C_1$-$C_{12}$alkyl; $N(R_6R_7)$—$C_1$-$C_{12}$alkyl; phenyl; or amino-phenyl;

$R_{10}$ is $C_1$-$C_{12}$alkyl; or $N^+(R_3R_4R_5)$—$C_1$-$C_{12}$alkyl; wherein $R_3$, $R_4$, $R_5$ $R_6$ and $R_7$ independently from each other are hydrogen; or $C_1$-$C_5$alkyl; and An is an anion.

Further preferred compounds of the present invention are those representatives, wherein D in formula (1) corresponds to formula

(1d)

wherein $R_{10}$ is $C_1$-$C_5$alkyl; or $N^+(R_3R_4R_5)$—$C_1$-$C_5$alkyl; and $R_3$, $R_4$ and $R_5$ independently from each other are hydrogen; or $C_1$-$C_5$alkyl.

More preferred representatives of the present invention correspond to formula

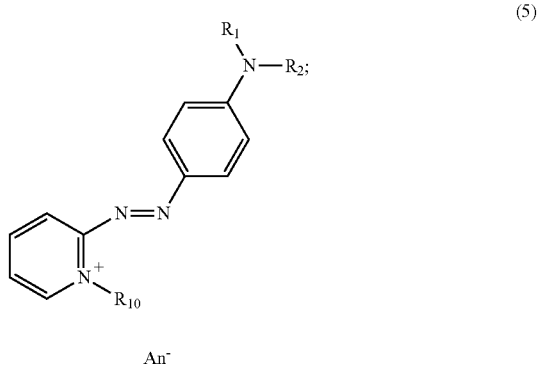

(5)

wherein $R_1$ and $R_2$ independently from each other are hydrogen; or aminophenyl;

$R_{10}$ is $C_1$-$C_5$alkyl; or $N^+(R_3R_4R_5)$—$C_1$-$C_5$alkyl;

$R_3$, $R_4$ and $R_5$ independently from each other are hydrogen; or $C_1$-$C_5$alkyl; and An is an anion.

Further preferred compounds of the present invention are those representatives, wherein in formula (1) corresponds to formula

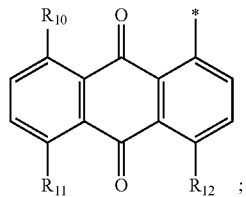

(1d)

wherein
$R_{10}$, $R_{11}$ and $R_{12}$ independently from each other are hydrogen; halogen; $C_1$-$C_{12}$alkyl; or $N^+(R_3R_4R_5)$—$C_1$-$C_{12}$alkyl; $C_1$-$C_{12}$alkylamino; $N^+(R_3R_4R_5)$—$C_1$-$C_{12}$alkylamino; and
$R_3$, $R_4$ and $R_5$ independently from each other are hydrogen; $C_1$-$C_{12}$alkyl; or amino-$C_1$-$C_5$alkyl.

More preferred representatives of the present invention correspond to formula

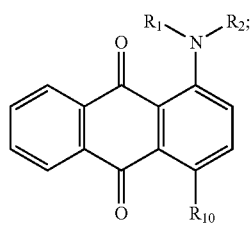

(6)

wherein
$R_1$ and $R_2$ independently from each other are hydrogen; $C_1$-$C_5$alkyl; $N(R_3R_4)$—$C_1$-$C_{12}$alkyl; or $N^+(R_3R_4R_5)$—$C_1$-$C_{12}$alkyl;
$R_3$, $R_4$ and $R_5$ independently from each other are hydrogen; $C_1$-$C_5$alkyl; or amino-$C_1$-$C_5$alkyl; and
$R_{10}$ is halogen; $C_1$-$C_{12}$alkyl; or amino-$C_1$-$C_{12}$alkyl.

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. When more than one composition is used during a treatment, as in mixing of the components of a typical oxidative dye product, the total weight to be considered is the total weight of all the compositions applied on the hair simultaneously (i.e. the weight found "on head") unless otherwise specified. The term "weight percent" may be denoted as "wt. %" herein.

As used herein, the term "hair" to be treated may be "living" i.e. on a living body or may be "non-living" i.e. in a wig, hairpiece or other aggregation of non-living keratinous fibers. Mammalian, particularly human, hair is preferred. However, wool, fur, and other keratin containing fibers are suitable substrates for the compositions according to the present invention.

As used herein, the term "pendant group" means a group of atoms attached to the core structure or chromophore. As described herein, the pendant group itself is not colored although it may influence the color of the chromophore. The pendant group may be further classified as an anchoring group or a hydrophobic group. A hydrophobic group (hydrophobe) is typically a carbon chain. An anchoring group is a group attached to either a permanent cation or incipient cation, occasionally it is attached to both a permanent cation and one or more incipient cations.

As used herein, the term "chromophore" means the part of the direct dye compound responsible for its color.

As used herein, the term "direct dye compound" means a dye used in a process in which dye molecules are attracted by physical forces at the molecular level to a textile or substrate such as the hair. As opposed to oxidative dyes, there is no chemical reaction required to form the chromophore. Additionally, there is no covalent bond formation between the direct dye and the substrate as opposed to reactive dyes. The direct dye compound does not undergo a chemical transformation before and after the dyeing process.

As used herein, the term "acid perspiration resistant" means resistant to human sweat, which is acidic in pH.

As used herein, the term "core structure" means the chromophore including one or two 5 permanent cations that are pendant to the chromophore or part of the chromophore.

In an embodiment, the chromophore is charged. In an embodiment, the chromophore is not charged as the permanent cation is pendant to the chromophore.

As used herein, the term "pendant" means when a functional group is linked to a core structure via covalent bond.

As used herein, the term "incipient cation" means a functional group that goes from neutral to positively charged due to protonation during a change in pH.

As used herein, the term "non-anionic foaming agent" is a material that facilitates formation of foam. The term typically refers to a surfactant which, when present in small amounts, reduces the surface tension of a liquid or increases its colloidal stability by inhibiting coalescence of bubbles.

As used herein, the term "hydrophobic moieties" means either hydrophobic molecules or hydrophobic functional groups.

The hair colorant compositions comprise one or more washfast direct dyes, optionally, oxidative dyes as well.

The compounds of formula (1) according to the present invention are suitable for dyeing organic materials, such as keratin-containing fibers, wool, leather, silk, cellulose or polyamides, cotton or nylon, and preferably human hair. The method of dyeing the hair comprises (a) applying to the hair a hair color composition comprising one or more direct dye compounds of formula (1), wherein the one or more direct dye compounds enter the hair shaft after the hair color composition is applied to the hair; and wherein the hair color composition has a pH of from about 7 to about 11; (b) rinsing the hair with water; wherein the pH of the hair after rinsing is from about 3.5 to about 6; and wherein the rinsing of the hair causes one or more of the one to four incipient cations to change from neutral to positively charged inside of the hair shaft.

The one to four incipient cations, typically an amino group or groups, are attached to the chromophore in addition to the existing permanent cation(s) to overcome the problems encountered in previous attempts to make cationic direct dyes more washfast. The chromophore would typically carry only one or two permanent positive charges such as quaternary ammonium salts, pyridinium, imidazolium, thiazolium, oxazolium, triazolium, pyrimidinium, triazinium, tetrazolium phenoxazinium, phenazinium or an analogous cation under basic conditions for typical hair color applications. The amino group(s) would remain mostly neutral under dyeing conditions (pH 10~11) because the typical pKa of aliphatic amines falls between 9~10.5. The dye would carry only one or two cationic charges under dyeing conditions, which provides the needed affinity (Coulombic attraction) for optimized uptake without preventing penetration due to relatively low charge density compared to polycationic dyes. However, once the coloring application is done and hair is rinsed, pH inside hair drops back to its natural pH, which is acidic, the amino group(s) attached to the chromophore would be protonated to become an ammonium cation, which adds one or more binding sites to the chromophore.

The pH change functions as a convenient switch to turn on additional binding group(s) to make the chromophores more washfast. Primary amines work the best when compared to secondary and tertiary amines for the following two reasons: 1. primary amines resist oxidation by hydrogen peroxide, while secondary and tertiary amines can be oxidized and lose their anchoring capability when used together with a bleaching agent; 2. the protonated primary ammonium cation is the smallest in size, which allows stronger interaction with anions on hair compared to secondary and tertiary amines with more steric hindrance.

The pH change functions as a convenient switch to turn on additional binding group(s) to make the chromophores more washfast. Overall, primary amines are more desirable than secondary and tertiary amines for the following two reasons: (1) the protonated primary ammonium cation is the smallest in size, which allows stronger interactions with anions on hair compared to secondary and tertiary amines with more steric hindrance; and (2) in the presence of oxidants like hydrogen peroxide which is used when bleaching of the hair's melanin is also desired at the same time, primary amines resist oxidation by hydrogen peroxide, while secondary and tertiary amines can be oxidized and lose their anchoring capability.

Surprisingly, dyes with hydrophobic moieties resist acid perspiration better than dyes without hydrophobic moieties.

The linear alkyl groups, and the one or more hydrophobic moieties may also function as modulators for the overall hydrophobicity of the dye. One of the common drawbacks of using exclusively cationic direct dyes for shading is off-tone fading as different dyes would be washed off hair at different rates, causing undesirable gradual color shift over time. Our technical approach minimizes off-tone fading by designing dyes of different colors with identical charge patterns with similar overall hydrophobicity, at the mean time, the fact that these inventive dyes are far more washfast than typical cationic dyes also contributes to minimal color lost and on-tone fading.

The synthesis procedure for the disclosed compounds is as follows: In a first step, a suitable chromophore is prepared.

Suitable chromophores for the present invention are: charged imidazole azoaryl or thiazole azoaryl residues, 1-alkylpyridinium azoaryl dyes, 1-alkylpyridinium-4-azoaryl compounds or 4-methyl(phenyl)hydrazono)methyl pyridinium compounds or charged aminoalkylated anthraquinone dyes. The presence of at least one permanent cation is mandatory for all compounds.

These chromophores can be prepared according to known procedures, preferably diazotization and coupling procedures. For example, the diazotization of imidazole is performed with p-anisidine or p-fluoroaniline; the thiazole residue is typically prepared by a diazotization of thiazole-2-amine and coupling to a corresponding aromatic compound. The 1-alkylpyridinium azo chromophore is accessible by a reduced coupling procedure of pyridine-2-amine with 4-nitroanisole in presence of sodium. The final blue chromophore is obtained by the reaction with p-phenylene diamine. 1-pyridinium-4-azoaryl chromophores are easily built up by a diazotization of 4-aminopyridines and subsequent coupling with suitable dialkyl aniline derivatives. 4-methyl(phenyl)hydrazono)methyl pyridinium chromophores are prepared by the condensation of a phenylhydrazine derivative with a 4-pyridinecarboxaldehyde.

All mentioned synthesis of chromophore structures are already described in the prior art and known to the expert person of ordinary skill. For a suitable color shade, the chromophore must comprise an electron-donating group—for example a dialkylamino- or alkyl- or amino group. Those groups can be introduced by a nucleophilic substitution reaction starting—for example—from the corresponding imidazole-azoaryl derivative p-substituted by chloride, bromide, fluoride or methoxy. An incipient cation can also be introduced in this step by using a suitable bis-alkyl-trisamine, i.e. dipropylenetriamine. Preferably, the primary groups of such trisamines are blocked by a protection group. Suitable protection groups for aminofunctions are for example: the tert.butyloxycarbonyl (BOC) group, phthalimide groups, acetyl or trifluoroacetyl groups and different Schiff bases.

The permanent cationic charge of the chromophore is introduced by an alkylation step of the imidazole, thiazole, pyridine or hydrazine chromophore. For the alkylation, suitable alkyl halogenides (alkylchlorides, -bromide, -iodides) or alkylmesylates, alkyltriflates or alkylsulfates are used. As alkylating agent, for example bromopropylamine hydrobromide is used for additionally introducing an alkyl group with a terminal primary amino. The presence of at least one of such an incipient cation is mandatory for all compounds according to the present invention.

Hydrophobic alkyl halogenides are used to introduce a hydrophobic aliphatic chain. A protected bromopropylamino derivative is for example suitable to introduce an incipient cation. As protecting groups, the same protecting groups for the amino group mentioned above are used.

Optionally, the introduction of additional hydrophobic groups to the chromophores are performed by a suitable alkylation process, i.e. alkylation of an imidazole azoaryl derivative with pentylbromide or by a substitution reaction of an imidazole azo arylfluoride with a hydrophobic alkyl derivative, i.e. bispentylamine.

When protected amino compounds are used, the cationic dyes must be deprotected in a final step. The Boc as well as acetyl and trifluoroacetyl groups are easily deprotected with acids, i.e. hydrochloride acid.

The synthesis of the compounds according to the present invention are disclosed in detail in the experimental part.

The hair color compositions described herein may be formed as thick liquid, cream, gel, emulsion, foam, aerosol mousse or as a solid form to which water is added to generate the oxidant and form a thickened vehicle suitable for hair coloring. They may comprise in addition to the ingredients indicated above further ingredients in order to further enhance the properties of the composition, including but not limited to: solvents; oxidative dyes, direct dyes; oxidizing agents; radical scavengers; thickeners and or rheology modifiers; chelants; pH modifiers and buffering agents; carbonate ion sources; peroxymonocarbonate ion sources; anionic, cationic, nonionic, amphoteric or zwitterionic surfactants, or mixtures thereof; anionic, cationic, nonionic, amphoteric or zwitterionic polymers, or mixtures thereof; fragrances; enzymes; dispersing agents; peroxide stabilizing agents; antioxidants; natural ingredients, e.g. proteins and protein compounds, and plant extracts; conditioning agents including silicones and cationic polymers, ceramides, preserving agents; and opacifiers and pearling agents (such as titanium dioxide and mica). Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose. A few of these ingredients are discussed hereinbelow, whose disclosure is of course non-exhaustive.

Optional Ingredients

The hair color compositions described herein may comprise, in addition to the ingredients indicated above, optional ingredients in order to further enhance the properties of the composition.

Suitable optional ingredients include, but are not limited to: solvents; oxidizing agents; alkalizing agents; oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Solvents

The hair color compositions described herein may further comprise a solvent. The solvent may be selected from water or a mixture of water and at least one organic solvent to dissolve the compounds that would not typically be sufficiently soluble in water. Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof. In an embodiment, the solvent may be selected from the group consisting of water, ethanol, propanol, isopropanol, glycerol, 1,2-propylene glycol, hexylene glycol, ethoxy diglycol, and mixtures thereof.

The composition may comprise water as a main ingredient, particularly in a total amount ranging from at least about 50%, alternatively from at least about 60%, alternatively from at least about 70%, by weight of the total composition.

In an embodiment, the composition may comprise a total amount of organic solvents ranging from about 1% to about 30%, by weight of 30 the total hair color composition.

Oxidizing Agents

The hair color composition described herein may comprise at least one source of an oxidizing agent. Preferred oxidizing agents for use herein are water soluble peroxygen oxidizing agents. Water-soluble peroxygen oxidizing agents are well known in the art and include, but are not limited to, hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulfates and the like. These inorganic perhydrate salts may be incorporated as monohydrates, tetrahydrates etc. Alkyl and aryl peroxides, and or peroxidases, oxidases, and uricases and their substrates may also be used. Mixtures of two or more such oxidizing agents can also be used if desired. The oxidizing agents may be provided in aqueous solution or as a powder which is dissolved prior to use. In an embodiment, the oxidizing agents may be selected from the group consisting of hydrogen peroxide, percarbonate, persulfates and combinations thereof.

In an embodiment, the hair color composition may comprise from 0.1% to 20% by weight, or from 1% to 15% by weight, or from 2% to 10% by weight of oxidizing agent.

A potential oxidizing agent for use herein is a source of peroxymonocarbonate ions formed in situ from a source of hydrogen peroxide and a hydrogen carbonate ion source. Moreover, this system is also particularly effective in combination with a source of ammonia or ammonium ions. Accordingly, any source of these peroxymonocarbonate ions may be used. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may be used both as an oxidizing agent and as a source of carbonate ions. Preferred sources of carbonate ions, carbamate and hydrocarbonate ions are sodium hydrogen carbonate, potassium hydrogen carbonate, ammonium carbamate, and mixtures thereof.

The oxidizing agent may comprise from 0.1% to 15% by weight, or from 1% to 10% by weight, or from 1% to 8% by weight of a hydrogen carbonate ion; and from 0.1% to 10% by 30 weight, or from 1% to 7% by weight, or from 2% to 5% by weight of the oxidizing agent of a source of hydrogen peroxide.

Alkalizing Agents

The hair color composition described herein may further comprise an alkalizing agent as known in the art. Any alkalizing agent known in the art may be used such as ammonia, alkanolamines for example monoethanolamine, diethanolamine, triethanolamine, monopropanolamine, dipropanolamine, tripropanolamine, 2-amino-2-methyl-1,3-propanediol, 2-5 amino-2-methyl-1-propanol, and 2-amino-2-hydroxymethyl-1,3-propanediol, guanidium salts, alkali metal and ammonium hydroxides such as sodium hydroxide, alkali metal and ammonium carbonates, and mixtures thereof. In an embodiment, the alkalizing agent may be ammonia and/or monoethanolamine.

The hair color compositions described herein may comprise from about 0.1% to about 10%, preferably from about 0.5% to about 6%, more preferably from about 1% to about 4% by weight of the alkalizing agent relative to the total weight of the composition.

The hair colorant compositions described above may have a pH of from 7 to 12, alternatively from 8 to 11. For embodiments comprising a peroxymonocarbonate ion, the pH may be up to and including pH 9.5, alternatively from 7.5 to 9.5, alternatively from 8.4 to 9.5, alternatively from 8.5 to 9.4, alternatively 9.0, and alternatively 9.3.

Any sub-components of the hair color compositions, such as a tint composition or an oxidizing composition, may have a different pH from the hair colorant composition. For example, if the tint composition comprises an alkalizing agent, the tint composition will have an alkaline pH, such as higher than 7. The oxidizing composition may comprise an acidic pH of less than 7.

When the hair color composition described herein is obtained by mixing a developer and a tint composition prior to use, the alkalizing agent is generally present in the tint composition.

Oxidative Dye Precursors

In addition to the direct dye compounds described herein, the hair color composition may further comprise one or more oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

In an embodiment, the hair color composition may comprise a total amount of oxidative dye precursors ranging up to about 12%, alternatively from about 0.1% to about 10%, alternatively from about 0.3% to about 8%, alternatively from about 0.5% to about 6%, by weight of the total composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-5 phenylenediamine), 2-methoxymethyl-p-phenylenediamine, 2-(1,2-dihydroxyethyl)p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, (2,3-diamino-6,7-dihydro-1H,5H-pyrazolo[1,2-a]pyrazol-1-one dimethanesulfonate), 4,5-diamino-1-hexylpyrazole, 4,5-diamino-1-heptylpyrazole, 15 methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-30 dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the hair color composition described herein is obtained by mixing a tint composition and a developer composition, the primary intermediates and couplers may be incorporated into the tint composition. 5

Additional Direct Dyes

The hair color composition may further comprise additional compatible direct dyes, in an amount sufficient to provide additional coloring, particularly with regard to intensity. In an embodiment, the composition may comprise a total amount of direct dyes ranging from about 0.05% to about 4%, by weight of the total composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a, 10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-30 (methylamino)-4-nitrophenoxy)ethanol, 3-(3-amino-4-nitrophenyl)propane-1, 2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the hair color composition is obtained by mixing a tint composition and a developer composition, the additional direct dyes may be incorporated into the tint composition.

Chelants

The hair color composition described herein may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

In an embodiment, the hair color composition may comprise a total amount of chelants ranging from at least about 0.01%, alternatively from about 0.01% to about 5%, alternatively from about 0.25% to about 3%, alternatively from about 0.5% to about 1%, by weight of the total composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof.

By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-10 N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—PO3H2) or its derivative —PO3R2, wherein R2 is a C1 to C6 alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triaminepenta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

In a specific embodiment, the composition comprises a chelant selected from the group consisting of diethylenetriamine-N,N',N"-polyacids, diethylenetriaminepentaacetic acid (DTPA), 30 diethylenetriaminepenta(methylene phosphonic acid) (DTPMP), diamineN,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS)

When the hair color composition is obtained by mixing a tint composition and a developer composition, the chelants may be incorporated in the tint composition and/or in the developer composition. A chelant may be present in the developer composition for stability.

Radical Scavengers

The hair color compositions described herein may comprise a radical scavenger. As used herein the term radical scavenger refers to a species that can react with a radical, to convert the radical species by a series of fast reactions to an unreactive or less reactive species. The radical scavenger is also preferably selected such that it is not an identical species as the alkalising agent and is present in an amount sufficient to reduce the damage to the hair during the colouring/bleaching process. The compositions of the present invention comprise a radical scavenger from about 0.1% to about 10%, preferably from about 1% to about 7% by weight of the radical scavenger relative to the total weight of the composition.

Suitable radical scavengers for use herein may be selected from the classes of alkanolamines, amino sugars, amino acids, esters of amino acids and mixtures thereof. Suitable compounds include 3-substituted-pyrazol-5-ones, 3-carboxy-1H-pyrazol-5-one, 3-methyl-1-phenyl-pyrazol-5-one, 3-methyl-1-p-tolyl-pyrazol-5-one, 3-methyl-1-(4-sulfophenyl)-pyrazol-5-one, 3-methyl-1-(4-sulfoamidophenyl)-pyrazol-5-one, 3-methyl-1-(3-sulfophenyl)-pyrazol-5-one, 3-methyl-1-(3-sulfoamidophenyl)-pyrazol-5-one, 3-methyl-1-(2-chloro-5-sulfophenyl)-pyrazol-5-one, 3-methyl-1-(2,5-dichloro-4-sulfophenyl)-pyrazol-5-one, 3-methyl-1-(4-chlorophenyl)-pyrazol-5-one, 3-methyl-1-(4-carboxyphenyl)-pyrazol-5-one, 3-carboxy-1-phenyl-pyrazol-5-one, 3-carboxy-1-(4-sulfophenyl)pyrazol-5-one, 1,3-diphenyl-pyrazol-5-one, methyl pyrazol-5-one-3-carboxylate, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, or mixtures thereof, or the salts, such as the potassium, sodium, or ammonium salts thereof, or mixtures thereof. In some embodiments, the inventive compositions may comprise glycine, sarcosine, lysine, serine, 2-methoxyethylamine, glucosamine, glutamic acid, morpholine, piperidine, ethylamine, 3-amino-1-propanol, or mixtures thereof.

pH Modifiers and Buffering Agents

The hair color compositions described herein may further comprise, in addition to the alkalizing agent discussed above, a pH modifier and/or buffering agent in an amount that is sufficiently effective to adjust the pH of the composition to fall within a range from about 3 to about 13, alternatively from about 8 to about 12, alternatively from about 9 to about 11.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-5 1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

The hair color compositions described herein may further comprise a thickener in an amount sufficient to provide the composition with a viscosity so that it can be readily applied to the hair without unduly dripping off the hair and causing mess.

In an embodiment, the hair color compositions may comprise a total amount of thickeners ranging from at least about 0.1%, alternatively at least about 1%, alternatively at least about 10%, alternatively at least about 20%, by weight of the total composition. Suitable thickeners include, but are not limited to: associative polymers, polysaccharides, non-associative polycarboxylic polymers, and mixtures thereof.

As used herein, the expression "associative polymers" means amphiphilic polymers comprising both hydrophilic units and hydrophobic units, for example, at least one C8 to C30 fatty chain and at least one hydrophilic unit. Associative polymers are capable of reversibly combining with each other or with other molecules. Suitable associative thickeners include, but are not limited to: nonionic amphiphilic polymers comprising at least one hydrophilic unit and at least one fatty-chain unit; anionic amphiphilic polymers comprising at least one hydrophilic unit and at least one fatty-chain unit; cationic amphiphilic polymers comprising at least one hydrophilic unit and at least one fatty-chain unit; and amphoteric amphiphilic polymers comprising at least one hydrophilic unit and at least one fatty-chain unit, and mixtures thereof.

Suitable nonionic amphiphilic polymers comprising at least one fatty chain and at least one hydrophilic unit include, but are not limited to: celluloses modified with groups comprising at least one fatty chain (such as hydroxyethylcelluloses modified with groups comprising at least one fatty chain chosen from alkyl, alkenyl and alkylaryl groups); hydroxypropyl guars modified with groups comprising at least one fatty chain; polyether urethanes comprising at least one fatty chain (such as C8-C30 alkyl or alkenyl groups); copolymers of vinylpyrrolidone and of fatty-chain hydrophobic monomers; copolymers of C1-C6 alkyl acrylates or methacrylates and of amphiphilic monomers comprising at least one fatty chain; copolymers of hydrophilic acrylates or methacrylates and of hydrophobic monomers comprising at least one fatty chain, and mixtures thereof. Commercially available anionic materials include those sold as Sepigel 305 by Seppic.

Suitable nonionic amphiphilic polymers comprising at least one hydrophilic unit and at least one fatty-chain unit include, but are not limited to: those polymers comprising at least one fatty-chain allyl ether unit and at least one hydrophilic unit comprising an ethylenic unsaturated anionic monomeric unit (such as a vinylcarboxylic acid unit, particularly a unit chosen from units derived from acrylic acids, methacrylic acids, and mixtures thereof), wherein the fatty-chain allyl ether unit corresponds to the monomer of formula (XXIII) below $$CH2=C(R1)CH2OBnR \qquad (XXIII)$$

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

Suitable anionic amphiphilic polymers include, but are not limited to: those polymers comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid, wherein the hydrophilic unit of unsaturated olefinic carboxylic acid type corresponds to, for example, the monomer of formula (XXIV) below $$CH2=C(R1)COOH \qquad (XXIV)$$

in which R1 is chosen from H, CH3, C2H5 and CH2COOH (i.e. acrylic acid, methacrylic, ethacrylic and itaconic acid units); and wherein the hydrophobic unit of the type such as a (C8-C30) alkyl ester or (C8-C30) oxyethylenated alkyl ester of an unsaturated carboxylic acid corresponds to, for example, the monomer of formula (XXV) below $$CH2=C(R1)COOBnR2 \qquad (XXV)$$

in which R1 is chosen from H, CH3, C2H5 and CH2COOH (i.e. acrylate, methacrylate, 30 ethacrylate and itaconate units), B is an ethyleneoxy radical, n is chosen from zero and integers ranging from 1 to 100, R2 is chosen from C8-C30 alkyl radicals, for example, C12-C22 alkyl radical. Anionic amphiphilic polymers may further be cross-linked. The crosslinking agent can be a monomer comprising a group (XXVI) below $$CH2=C< \qquad (XXVI)$$

with at least one other polymerizable group whose unsaturated bonds are not conjugated with respect to one another. Mention may be made, for example, of polyallyl ethers such as polyallylsucrose and polyallyl pentaerythritol.

Suitable cationic amphiphilic polymers include, but are not limited to: quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Suitable amphoteric amphiphilic polymers comprising at least one hydrophilic unit and at least one fatty-chain unit, may be made, for example, of methacrylamidopropyltrimethylammonium chloride/acrylic acid/C8-C30 alkyl methacrylate copolymers, wherein the alkyl radical is, for example, a stearyl radical.

In an embodiment, the associative polymers may comprise at least one hydrophilic unit which is unsaturated carboxylic acid or its derivatives, and at least one hydrophobic unit which is a C8 to C30 alkyl ester or oxyethylenated C8-C30 alkyl ester of unsaturated carboxylic acid. The unsaturated carboxylic acid is preferably acrylic acid, methacrylic acid or itaconic acid. Commercially available materials include those sold as Aculyn-22 by Rohm & Haas; Permulen TR1, Carbopol 20, Carbopol Ultrez-21/-30 by Noveon, Structure 2001/3001 by National Starch. Other preferred associative polymers include polyether polyurethane, commercially available as Aculyn-44/-46 by Rohm and Haas. Further preferred associative polymers include cellulose modified with groups comprising at least one C8-C30 fatty chain, commercially available under the trade name Natrosol Plus Grade 330 CS by Aqualon.

Suitable non-associative cross-linked polycarboxylic polymers include, but are not limited to: cross-linked acrylic acid homopolymers, copolymers of acrylic or (meth)acrylic acid 30 and of C1-C6 alkyl acrylate or (meth)acrylate, and mixtures thereof. Commercially available materials include those sold as Carbopol 980/981/954/1382/2984/5984 by Noveon, Synthalen M/Synthalen L/Synthalen K/Synthalen CR by 3V, Aculyn-33 by Rohm and Haas.

Suitable polysaccharides include, but are not limited to: glucans, modified and unmodified starches (such as those derived, for example, from cereals, for instance wheat, corn or rice, from vegetables, for instance yellow pea, and tubers, for instance potato or cassava), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and non-ionic derivatives thereof (hydroxypropyl guar) and biopolysaccharides, such as xanthan gums, gellan gums, welan gums, scleroglucans, succinoglycans, and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums—Polysaccharides and their Derivatives", edited by Roy L. Whistler, Second Edition, published by Academic Press Inc., all three being incorporated herein by reference. A preferred polysaccharide is a bio-polysaccharide, particularly bio-polysaccharides selected from xanthan gum, gellan gum, welan gum, scleroglucan or succinoglycan; commercially available as Keltrol® T by Kelco and Rheozan® by Rhodia Chimie. Another preferred polysaccharide is hydroxypropyl starch derivative, particularly hydroxypropyl starch phosphate, commercially available as Structure XL® by National Starch, a hydrophobically modified cellulose derivative, commercially available as Structure® Cel 500 HM by AkzoNobel.

Commercially available salt-tolerant thickeners include, but not limited to: xanthan, guar, hydroxypropyl guar, scleroglucan, methyl cellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), polyvinylpyrrolidone (Povidone, FlexiThix™), Acrylates/Ceteth-20 Itaconate Copolymer (Structure 3001), hydroxypropyl starch phosphate (Structure ZEA), polyethoxylated urethanes or 30 polycarbamyl polyglycol ester such as PEG-150/Decyl/SMDI copolymer (Aculyn 44), PEG-150/Stearyl/SMDI copolymer (Aculyn 46), trihydroxystearin (Thixcin), acrylates copolymer (Aculyn 33) or hydrophobically modified acrylate copolymers (such as Acrylates/Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphophilic polymers comprising at least one fatty chain and at least one hydrophilic unit selected from polyether urethanes comprising at least one fatty chain, blends of Ceteth—10 phosphate, Dicetyl phosphate and Cetearyl alcohol (available as Crodafos CES), and mixtures thereof.

Salt

In an embodiment, cosmetically acceptable salt, such as ammonium, sodium or potassium salts with appropriate counter ions, may be added to the hair color compositions described herein to act as leveling agents to minimize patchy coloring results.

Carbonate Ion Sources

The hair color compositions described herein may further comprise a source of carbonate ions, carbamate ions, hydrogen carbonate ions, and mixtures thereof in a sufficient amount to reduce damage to the hair during the coloring process.

In an embodiment, the hair color compositions may comprise a total amount of a carbonate ion source ranging from about 0.1% to about 15%, alternatively from about 0.1% to about 10%, alternatively from about 1% to about 7%, by weight of the total composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

Conditioning Agents

The hair color compositions described herein may further comprise a conditioning agent, and/or be used in combination with a composition comprising a conditioning agent.

In an embodiment, the hair color compositions may comprise a total amount of conditioning agents ranging from about 0.05% to about 20%, alternatively from about 0.1% to about 15%, alternatively from about 0.2% to about 10%, alternatively from about 0.2% to about 2%, alternatively from about 0.5% to 2%, by weight of the total composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Particularly useful conditioning materials may be cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain, described hereinafter.

Suitable silicones include, but are not limited to: polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain and mixtures thereof. Said organofunctional group(s) may be selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion. Suitable silicones also include: silicones containing groups that may be ionized into cationic groups, for example aminosilicones containing at least 10 repeating siloxane (Si(CH3)2-O) units within the polymer chain, with either terminal, graft, or a mixture of terminal and graft aminofunctional groups. Example functional groups are not limited to aminoethylaminopropyl, aminoethylaminoisobutly, aminopropyl. In the case of graft polymers, the terminal siloxane units can be (CH3)3Si—O, R12(CH3)2Si—O, where R12 can be either OH or OR13, where R13 is a C1-C8 alkyl group, or a mixture of both terminal groups. These silicones are also available as preformed emulsions. Commercially available aminosilicones include those sold as DC-2-8566, DC 7224, DC-2-8220 by Dow Corning; 30 SF1708, SM2125 by GE Silicones; Wacker Belsil ADM 653/ADM 1100/ADM 1600/ADM 652/ADM 6057E/ADM 8020 by Wacker Silicones; DC929, DC939, DC949 by Dow Corning; SM2059 by GE Silicones. Suitable aminosilicones may also contain additional functional groups, particularly additional functional groups including polyoxyalkylene, the reaction product of amines and carbinols, and alky chains. Commercially available materials are known as methoxy PEG/PPG-7/3 Aminopropyl Dimethicone (e.g. Abil Soft AF100, by Degussa), or as Bis(C13-15 Alkoxy)PG Amodimethicone (e.g. DC 8500, by Dow Corning).

Suitable cationic polymers include, but are not limited to: polymers comprising units of at least one amine group chosen from primary, secondary, tertiary and quaternary amine groups that may either form part of the main polymer chain or be borne by a side substituent that is directly attached to the main polymer chain. Such cationic polymers generally have a number average molecular mass ranging from about 500 to about 5×106, alternatively from about 1000 to about 3×106. Preferably the cationic polymers are selected from polymers of the polyamine, polyamino amide and polyquaternary ammonium type.

Suitable polymers of the polyamine, polyamino amide and polyquaternary ammonium type include, but are not limited to:

1) Homopolymers and copolymers derived from acrylic or methacrylic esters or amides. Copolymers of these polymers may also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinylactams such as vinlypyrrolidone and vinylcaprolactam, and vinyl esters. Suitable examples include copolymers of acrylamide and of methacryloyloxyethyltrimethylammonium methosulfate, including polymers known as Polyquaternium-5 (e.g. commercially available under the trade name Reten 210/220/230/240/1104/1105/1006 by Hercules; Merquat 5/5 SF by Nalco); copolymers of vinylpyrrolidone and dimethylaminopropyl methacrylamide, including polymers known as Polyquaternium-28 (e.g. Gafquat HS-100 by ISP); copolymers of vinyl pyrrolidone and dialkyaminoalkyl acrylates or methactylates, including polymers known as Polquaternium-11 (see Gafquat 440/734/755/755N by ISP; Luviquat PQ11 PM by BASF; Polyquat-11 SL by Sino 25 Lion); copolymers vinylpyrrolidone, dimethylaminopropyl methacrylamide and methacryloylaminopropyl lauryldimonium chloride, including polymers known as polyquaternium-55 (e.g. Styleze W-20 by ISP); copolymers of acrylic acid, acrylamide and methacrylamidopropyltrimonium chloride, including polymers known as Polyquaternium-53 (e.g. Merquat 2003 by Nalco); copolymers of dimethyaminopropylacrylate (DMAPA), acrylic acid and acrylonitrogens and diethyl sulphate, including polymers known as Polyquaternium-31 (e.g. Hypan QT100 by Lipo); copolymers of acrylamide, acrylamidopropyltrimonium chloride, 2-amidopropylacrylamide sulfonate, and dimethyaminopropylacrylate (DMAPA), including polymers known as polyquaternium-43 (e.g. Bozequat 4000 by Clairant); copolymers of acrylic acid, methylacrylate and methacrylamidopropyltrimonium chloride, including polymers known as Polyquaternium-47 (e.g. Merquat 2001/2001N by Nalco); copolymers of methacryloyl ethyl betaine, 2-hydroxyethyl methacrylate and methacryloyl ethyl trimethyl ammonium chloride, including polymers known as Polyquaternium-48 (e.g. Plascize L-450 by Goo Chemical); copolymers of acrylic acid diallyl dimethyl ammonium chloride and acrylamide, including polymers known as polyquaternium-39 (e.g. Merquat 3330/3331 by Nalco). Further suitable examples include copolymers of methacrylamide methacrylamido-propyltrimonium and methacryloylethyltrimethyl ammonium chloride and their derivatives, either homo or copolymerised with other monomers, including polymers known as Polyquaternium-8, Polyquaternium-9, Polyquaternium-12, Polyquaternium-13 Polyquaternium-14, Polyquaternium-10 (e.g. Rohagit KF 720 F by Rohm), Polyquaternium-30 (e.g. Mexomere PX by Chimex), Polyquaternium-33, Polyquaternium-35, Polyquaternium-36 (e.g. Plex 3074 L by Rhon), Polyquaternium 45 (e.g. Plex 3073L by Rohn), Polyquaternium 49 (e.g. Plascize L-440 by Goo Chemicals), Polyquaternium 50 (e.g. Plascize L-441 by Goo Chemicals), Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Suitable examples include copolymers of hydroxyethylcelluloses and diallyldimethyl ammonium chlorides, including polymers known as Polyquaternium-4 (e.g. Celquat L 200 and Celquat H 100 by National Starch); copolymers of hydroxyethylcelluloses and a trimethyl ammonium substituted epoxide, including polymers known as Polyquaternium-10 (e.g. AEC Polyquaternium-10 by A&E Connock; Catinal C-100/HC-35/HC-100/HC-200/LC-100/LC-200 by Toho; Celquat SC-240C/SC-230M by National Starch; Dekaquat 400/3000 by Dekker; Leogard GP by Akzo Nobel; RITA Polyquat 400/3000 by RITA; UCARE Polymer JR-25 125/JR-400/JR-30M/LK/ LR 400/LR 30M by Amerchol); copolymers of hydroxyethylcelluloses and lauryl dimethyl ammonium substituted epoxides, including polymers known as Polyquaternium-24 (e.g. Quatrisoft polymer LM-200 by Amerchol); derivatives of hydroxypropyl guar, including polymers as guar hydroxypropyltrimonium chloride (e.g. Catinal CG-100, Catinal CG-200 by Toho; Cosmedia Guar C-261N, Cosmedia Guar C261N, Cosmedia 30 Guar C-261N by Cognis; DiaGum P 5070 by Freedom Chemical Diamalt; N-Hance Cationic Guar by Hercules/ Aqualon; Hi-Care 1000, Jaguar C-17, Jaguar C-2000, Jaguar C-13S, Jaguar C-14S, Jaguar Excel by Rhodia; Kiprogum CW, Kiprogum NGK by Nippon Starch); hydroxypropyl derivatives of guar hydroxypropyltrimonium chloride, including polymers known as hydroxypropyl guar hydroxypropyltrimonium chloride (e.g. Jaguar C-162 by Rhodia).

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Suitable examples include the polymer adipic acid/epxoypropyl/diethylenetriamine.

5) Cyclopolymers of dialkdiallylamine or of dialkyldiallylammonium, including: Dimethyldiallyammonium chloride polymers, including polymers known as Polyquaternium-6 (e.g. Merquat 100 by Nalco; Mirapol 100 by Rhodia; Rheocare CC6 by Cosmetic Rheologies; AEC polyquaternium-6 by A&E Connock; Agequat 400 by CPS; Conditioner P6 by 3V Inc.; Flocare C106 by SNF; Genamin PDAC by Clariant; Mackernium 006 by McIntyre); copolymers of acrylamides and dimethyldiallylammonium chlorides monomers, including polymers known as Polyquaternium-7 (e.g. AEC Polyquaternium-7 by A&E Connock; Agequat-5008/C-505 by CPS; Conditioner P7 by 3V Inc.; Flocare C 107 by SNF; Mackernium 007/007S by McIntyre; ME Polymer 09W by Toho; Merquat 550/2200/S by Nalco; Mirapol 550 by Rhodia; Rheocare CC7/CCP7 by Cosmetic Rheologies; Salcare HSP-7/SC10/Super 7 by Ciba); copolymers of dimethyldiallylammoniumchlorides and acrylic acids, including polymers known as polyquaternary-22 (e.g. Merquat 280/ Merquat 295 by Nalco).

6) Quaternary diammonium polymers comprising repeat units corresponding to [—N+(R1)(R2)-A1-N+(R3)(R4)-B1-][2X—], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are chosen from liner or branched C1-C6 alkyl radicals substituted with at least one group chosen from nitrile, ester, acyl and amide groups and groups of —CO—O—R5-D and —CO—NH-30 R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X— is an anion derived from inorganic and organic acids. D is chosen from a glycol residue, a bis-secondary diamine residue, a bis-primary diamine residue or a ureylene group. Suitable examples include polymers known as Hexadimethrine chloride, where R1, R2, R3 and R4 are each methyl radicals, A1 is (CH2)3 and B1 is (CH2)6 and X=Cl; as polyquaternium-34 where R1 and R2 are ethyl radicals and R3 and R4 are methyl radicals and A1 is (CH2)3 and B1 is (CH2)3 and X=Br (e.g. Mexomere PAX by Chimax).

7) Polyquaternary ammonium polymers comprising repeating units of formula [—N+(R6)(R7)-(CH2)r-NH—CO—(CH2)q-(CO)t-NH—(CH2)s-N+(R8)(R9)-A-][2X—], in which R6, R7, R8 and R9 which may be identical or different, are chosen from a hydrogen atom and a methyl, ethyl, propyl, hydroxyethyl, hydroxypropyl, and —CH2CH2(OCH2CH2)pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X— is anion such as a halide. T is an integer chosen to be equal to 0 or 1. A is chosen from divalent radicals such as —CH2-CH2-O—CH2-CH2-. Suitable examples include: polymers known as polyquaternium-2, where r=s=3, q=0, t=0, R6, R7, R8 and R9 are methyl groups, and A is —CH2-CH2-O—CH2-CH2 (e.g. Ethpol PQ-2 from Ethox; Mirapol A-15 by Rhodia); as polyquaternium-17 where r=s=3, q=4, t=1 R6, R7, R8 and R9 are methyl groups, and A is —CH2-

CH2-O—CH2-CH2; as Polyquaternium 18, where r=s=3, q=7, t=1 R6, R7, R8 and R9 are methyl groups, and A is —CH2-CH2-O—CH2-CH2; as the block copolymer formed by the reaction of Polyquaternium-2 with Polyquaternium-17, which are known as Polyquaternium 27 (e.g. Mirapol 175 by Rhodia).

8) Copolymers of vinylpyrrolidones and of vinylimidazoles and optionally vinylcaprolactums, including polymers known as Polyquaternary-16 formed from methylvinylimidazolium chlorides and vinylpyrrolidones (e.g. Luviquat FC370/FC550/FC905/HM-552 by BASF); copolymers of vinylcaprolactams and vinylpyrrolidones with methylvinylimidazolium methosulfates, including polymers known as Polyquaternium-46 (e.g. Luviquat Hold by BASF); copolymers of vinylpyrrolidones and quaternized imidazolines, including polymers known as polyquaternary 44 (e.g. Luviquat Care 30 by BASF).

9) Polyamines such as Polyquart H sold by Cognis under the reference name polyethylene glycol (15) tallow polyamine 10) Cross linked methacryloyloxy(C1-C4)alkyltri(C1-C4) alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, including polymers known as Polyquaternium-37 (e.g. Synthalen CN/CR/CU sold by 3V sigma; or as a dispersion in another media such as Salcare SC95/SC96 by Ciba; Rheocare CTH(E) by Cosmetic Rheologies) and polymers known as Polyquaternium-32 (e.g. sold as a dispersion in mineral oil such as Salcare SC92 by Ciba).

11) Further examples of cationic polymers include polymers known as Polyquaternium 10 51 (e.g. Lipidure-PMB by NOF), as Polyquaternium 54 (e.g. Qualty-Hy by Mitsui), as Polyquaternium 56 (e.g. Hairrol UC-4 by Sanyo chemicals), as Polyquaternium 87 (e.g. Luviquat sensation by BASF).

12) Silicone polymers comprising cationic groups and/or groups which may be ionised into cationic groups. Suitable examples include cationic silicones of the general formula (R10-15 N+(CH3)2)-R11-(Si(CH3)2-O)x-R11-(N+(CH3)2)-R10), where R10 is an alkyl derived from coconut oil, and R11 is (CH2CHOCH2O(CH2)3 and x is a number between 20 and 2000, including polymers known as Quaternium 80 (e.g. Abil Quat 3272/3474 sold by Goldschmidt); silicones containing groups which may be ionised into cationic groups, for example aminosilicones containing at least 10 repeating siloxane —(Si(CH3)2-O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3Si—O or R12(CH3)2Si—O, where R12 can be either OH or OR13, where R13 is a C1-C8 alky group, or a mixture of both functional terminal groups. These silicones are also available as preformed emulsions. Polymer with terminal siloxane units of (CH3)3Si—O examples includes polymers known as trimethylsilylamodimethicone (e.g. DC-2-8566, DC 7224, DC-2-8220 by Dow Corning; SF1708, SM 2125 GE Silicones; Wacker Belsil ADM 653 by Wacker silicones). Further examples include polymers with terminal siloxane units of (R12O)(CH3)2Si—O where R12 can be either OH or OR13, where R13 is a C1-C8 alky group, or a mixture of both 30 functional terminal groups, known as amodimethicone (e.g. Wacker Belsil ADM 1100/ADM 1600/ADM 652/ADM 6057E/ADM 8020 by Wacker Silicones; DC929, DC939, DC949 by Dow Corning; SM2059 by GE silicones). Silicones containing groups which may be ionised into cationic groups—for example silicones containing at least 10 repeating siloxane (Si(CH3)2-O) units within the polymer chain, with either terminal, graft or a mixture of terminal and graft aminofunctional groups, together with additional functional groups. Additional functional groups can include polyoxyalkylene, the reaction product of amines and carbinols, alky chains. For example, products known as methoxy PEG/PPG-7/3 Aminopropyl Dimethicone (e.g. Abil Soft AF100 by Degussa). For example products known as Bis (C13-15 Alkoxy) PG Amodimethicone (e.g. DC 8500 by Dow Corning).

In an embodiment, the cationic polymer may be selected from the group consisting of polyquaternium 37, polyquaternium 7, polyquaternium 22, polyquaternium 87, and mixtures thereof; alternatively from the group consisting of polyquaternium 37, polyquaternium 22, and mixtures thereof.

Surfactants

The hair color compositions described herein may further comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof.

In an embodiment, the hair color compositions may comprise a total amount of surfactants ranging from about 0.01% to about 60%, alternatively from about 0.05% to about 30%, alternatively from about 0.1% to about 25%, alternatively from about 0.1% to about 20%, by weight of the total composition.

The compositions may comprise a mixture of an anionic surfactant and an amphoteric surfactant with one or more nonionic surfactants. The composition may comprise a total amount of anionic surfactant ranging from about 0.01% to about 20%, alternatively from about 0.05% to about 15%, alternatively from about 0.1% to about 15%, by weight of the total composition; and a total amount of amphoteric and/or nonionic components, which may range independently from each other from about 0.01% to about 15%, alternatively from about 0.05% to about 10%, alternatively from about 0.1% to about 8%, by weight of the total composition.

Suitable anionic surfactants include, but are not limited to: salts (such as alkaline salts, for example, sodium salts, ammonium salts, amine salts, amino alcohol salts and magnesium salts) of the following compounds: alkyl sulphates, alkyl ether sulphates, alkylamido ether sulphates, 30 alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated (C6-C24) alkyl ether carboxylic acids, polyoxyalkylenated (C6-C24) alkylaryl ether carboxylic acids, polyoxyalkylenated (C6-C24) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Nonionic surfactants are compounds that are well known (see, for example, in this respect "Handbook of Surfactants" by M. R. Porter, published by Blackie & Son (Glasgow and London), 1991, pp. 116-178). Suitable non-ionic surfactants include, but are not limited to: polyethoxylated, polypropoxylated and polyglycerolated fatty acids, alkyl phenols, α-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their momoethanolamine and diethanolamine derivatives, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as (C10-C14)alkylamine oxides or N-acylaminopropylmorpholine oxides.

Suitable amphoteric surfactants include, but are not limited to: aliphatic secondary and tertiary amine derivatives in which the aliphatic radical is chosen from linear and branched chains comprising from 8 to 22 carbon atoms and comprising at least one water-soluble anionic 30 group (for example carboxylate, sulphonate, sulphate, phosphate or phosphonate); mention may also be made of (C8-C20) alkylbetaines, sulphobetaines, (C8-C20)alkylamido(C1-C6) alkylbetaines or (C8-C20)alkylamido(C1-C6)alkylsulphobetaines. Among the amine derivatives, mention may be made of the products sold as Miranol, as described, for example, in U.S. Pat. No. 2,528,378 and and having the structures of: R2-CON HCH2CH2-N+(R3)(R4)(CH2COO—), (XXVII) in which: R2 is chosen from alkyl radicals derived from an acid R2-COOH present in hydrolysed coconut oil, and heptyl, nonyl and undecyl radicals, R3 is a β-hydroxyethyl group and R4 is a carboxymethyl group; and of R5-CONHCH2CH2-N(B)(C) (XXVIII) wherein B represents —CH2CH2OX', C represents —(CH2)z-Y', with z=1 or 2, X' is chosen from the —CH2CH2-5 COOH group and a hydrogen atom, Y' is chosen from —COOH and —CH2-CHOH—SO3H radicals, R5 is chosen from alkyl radicals of an acid R5-COOH present in coconut oil or in hydrolysed linseed oil, alkyl radicals, such as C7, C9, C11 and C13 alkyl radicals, a C17 alkyl radical and its iso form, and unsaturated C17 radical. These compounds are classified in the CTFA dictionary, 5th edition, 1993, under the names disodium cocoamphodiacetate, disodium 10 lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid. Salts of diethyl aminopropyl cocoaspartamid can be also used. 2,781,354

Suitable cationic surfactants include, but are not limited to, the quaternary ammonium salts A) to D) as defined hereinafter:

A) Quaternary ammonium salts of general formula (XXIX) below:

wherein X— is an anion chosen from halides (chloride, bromide and iodide), (C2-C6)alkyl sulphates, such as methyl sulphate, phosphates, alkyl and alkylaryl sulphonates, and anions derived from organic acids, such as acetate and lactate, and wherein R1 to R4 are as below in i) or ii).

i) Radicals R1 to R3, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from: alkyl, alkoxy and alkylamide radicals. R4 is chosen from linear and branched alkyl radicals comprising from 16 to 30 carbon atoms. A suitable cationic surfactant is, for example, a behenyltrimethylammonium salt (for example chloride).

ii) Radicals R1 and R2, which may be identical or different, are chosen from linear and 30 branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from alkyl, alkoxy, alkylamide and hydroxyalkyl radicals comprising from about 1 to 4 carbon atoms. Radicals R3 and R4, which may be identical or different, are chosen from linear and branched alkyl radicals comprising from 12 to 30 carbon atoms, the said alkyl radicals comprise at least one function chosen from ester and amide functions. R3 and R4 may be chosen from (C12-C22)alkylamido(C2-5 C6)alkyl and (C12-C22) alkylacetate radicals. A suitable cationic surfactant is, for example, a dicetyldimethyl ammonium salt (for example chloride);

B) Quaternary ammonium salts of imidazolinium of formula below:

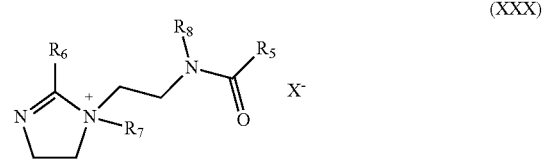

in which R5 is chosen from alkenyl and alkyl radicals comprising from 8 to 30 carbon atoms, for example fatty acid derivatives of tallow, R6 is chosen from a hydrogen atom, C1-C4 alkyl radicals and alkenyl and alkyl radicals comprising from 8 to 30 carbon atoms, R7 is chosen from C1-C4 alkyl radicals, R8 is chosen from a hydrogen atom and C1-C4 alkyl radicals, and X— is an anion chosen from halides, phosphates, acetates, lactates, alkyl sulphates, alkyl sulphonates and alkylaryl sulphonates. In one embodiment, R5 and R6 are, for example, a mixture of radicals chosen from alkenyl and alkyl radicals comprising from 12 to 21 carbon atoms, such as fatty acid derivatives of tallow, R7 is methyl and R8 is hydrogen. Such a product is, for example, Quaternium-27 (CTFA 1997) or Quaternium-83 (CTFA 1997), commercially available as "Rewoquat®" W75/W90/W75PG/W75HPG by Witco.

C) Diquaternary ammonium salts of formula (XXXI):

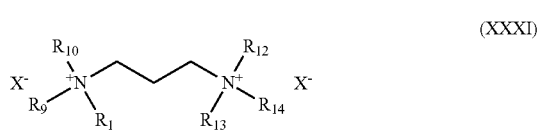

(XXXI)

EXAMPLES

Example 1: (E)-1,3-bis(3-aminopropyl)-2-((4-dimethylamino)phenyl)diazenyl)-1H-imidazol-3-ium bromide dihydrochloride

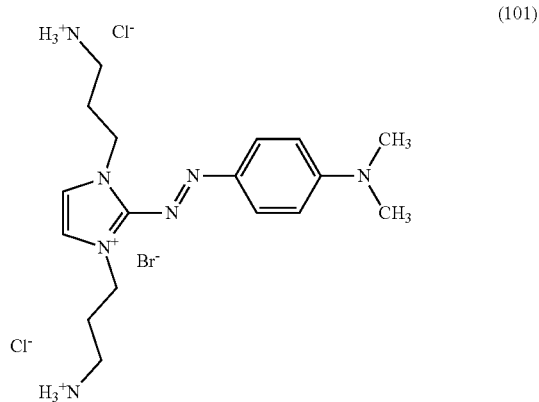

(101)

Example 1

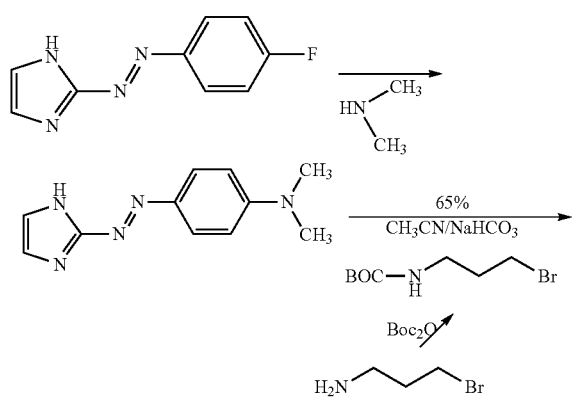

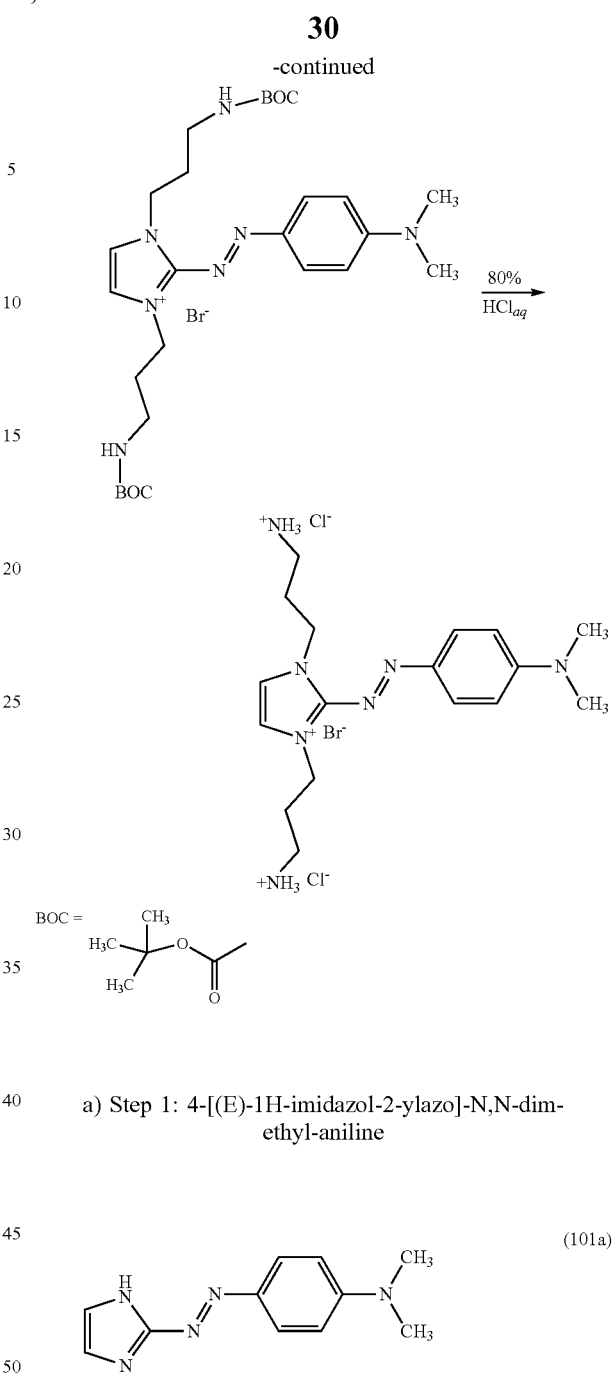

a) Step 1: 4-[(E)-1H-imidazol-2-ylazo]-N,N-dimethyl-aniline (101a)

20 g (0.105 mol) 2-((4-fluorphenyl)diazenyl)-1H-imidazole prepared according to literature (V. Eliu et al, WO2007025889) were suspended in 60 ml dimethylsulfoxide. To this suspension, 60 ml (0.532 mol) of an aqueous solution (40%) of dimethylamine was added within 10 minutes. The product mixture was heated to 80° C. and stirred at this temperature for 6 hours. Then the reaction solution was slowly cooled down to 20° C. A brown suspension was formed. The precipitate was filtered-off, washed with distilled water and dried at 40° C. at high vacuum.

Yield: 14 g, yellow solid.

$^1$H NMR (DMSO-$d_6$): δ=3.20 (s; 6H; 2×H$_3$), 6.80, 7.20 and 7.78 (each m; 2H; Aryl-H), 12.5 (s, br, NH) ppm.

b) Step 2: 2-((E)-(4-(dimethylamino)phenyl)diazenyl)-1,3-bis(3-((((1,1-dimethylethyl)oxy)carbonyl)amino)propyl)-1H-imidazol-3-ium bromide

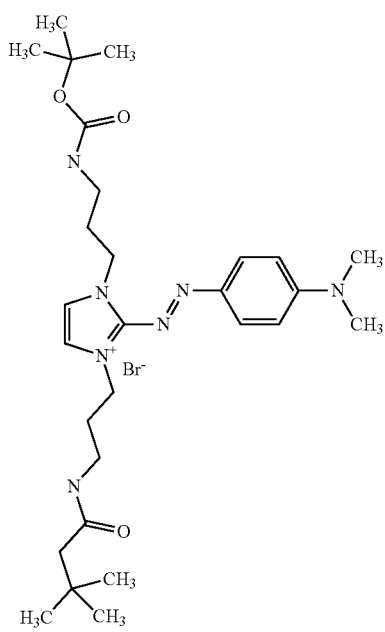

(101b)

13.2 g (0.061 mol) 4-[(E)-1H-imidazol-2-ylazo]-N,N-dimethyl-aniline prepared in step 1a) were suspended in 240 ml dioxane and stirred at 25° C. To this suspension, 10.2 g (0.121 mol) sodium bicarbonate and 43.8 g (0.184 mol) tert-butyl N-(3-bromopropyl)carbamate were added. The reaction mixture is heated to 100° C. After 4 hours, another 25.6 g sodium hydrogencarbonate were added. The reaction mixture is kept at 100° C. for another 10 hours and then cooled down to 20° C.

700 ml of ethyl acetate were poured into the product mixture. The formed precipitate was filtered-off. The residue was suspended in 100 ml methanol and stirred at 20° C. for 1 hour. The solid residue was again collected by filtration, washed with 100 ml ethanol and dried at 40° C. at high vacuum.

Yield: 37 g (74%), red solid.

$^1$H NMR (DMSO-$d_6$): δ=1.31 (s; 18H, CH$_3$), 1.93 (m; 4H, CH$_2$), 3.0 (m; 4H, CH$_2$), 3.24 and 3.35 (s; NCH$_3$), 4.37 (m; 4H, CH$_2$), 6.98 (m; 3H, Signals overlapping, Aryl-H and NH), 7.84 (s; 2H, Imidazoyl-H), 7.92 (m; 2H, Aryl-H) ppm.

c) Final Step 27 g (0.044 mol) of intermediate prepared in 1 b) were suspended in 30 ml water and stirred at 20° C. 200 ml of a 4N hydrochloric acid were slowly added within 5 minutes. The product mixture has been stirred at 20° C. for 4 hours. The obtained dark red solution was washed with 250 ml of 1-butanol. The aqueous phase was carefully evaporated in vacuum to give a dark violet raw product. It was suspended in 200 ml of ethyl acetate and stirred at 20° C. for two hours. The solid was collected by filtration, washed with ethyl acetate and dried in high vacuum at 40° C.

Yield: 18 g (99%), red solid.

UV $λ_{max}$=540 nm.

$^1$H NMR (DMSO-$d_6$): δ=2.16 (m; 4H, CH$_2$), 2.87 (m; 4H, CH$_2$), 3.25 (s; 6H, NCH$_3$), 4.53 (br t; 4H, CH$_2$), 6.98 (d; 2H, Aryl-H), 7.96 (s; 2H, Imidazoyl-H), 8.02 (d; 2H, Aryl-H), 8.26 (br; 6H, NH$_3$) ppm.

Example 2: (E)-1,3-bis-(3-ammoniopropyl)-2-((4-(dipentylamino)phenyl)diazenyl)-1H-imidazol-3-ium trifluoracetate

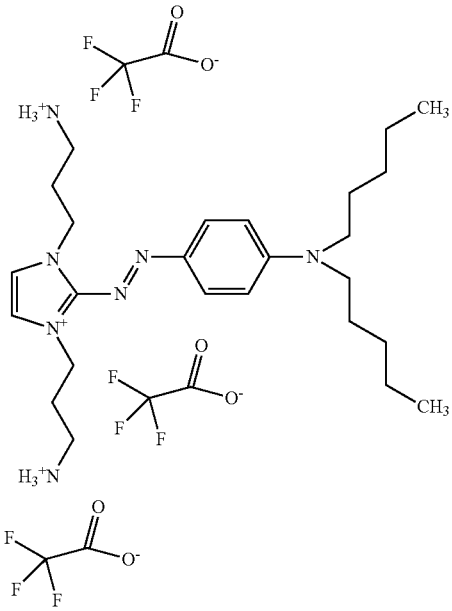

(102)

Synthesis Scheme of Example 2

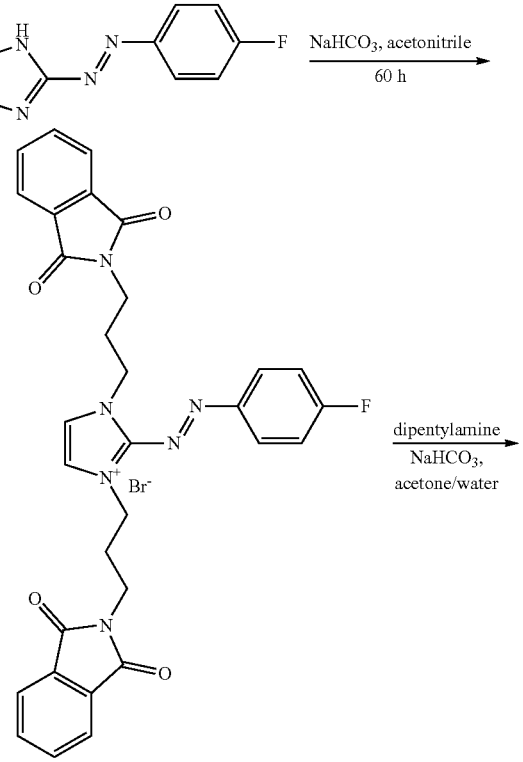

-continued

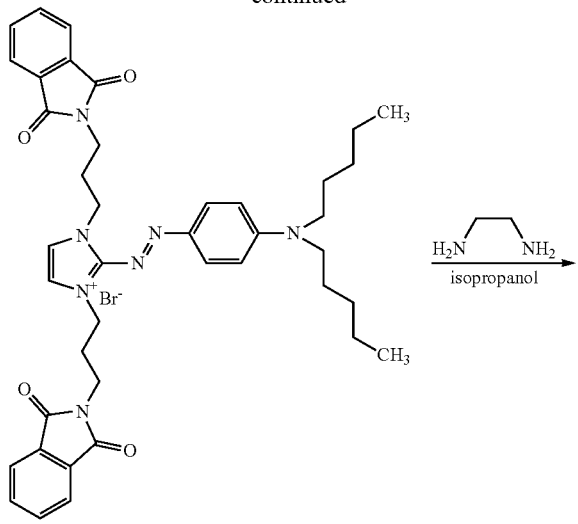

a) Step 1 1,3-bis(3-(1,3-dioxo-1,3-dihydro-2H-isoindole-2-yl)propyl)-2-((E)-(4-fluorophenyl)diazenyl)-1H-imidazol-3-ium bromide (102a)

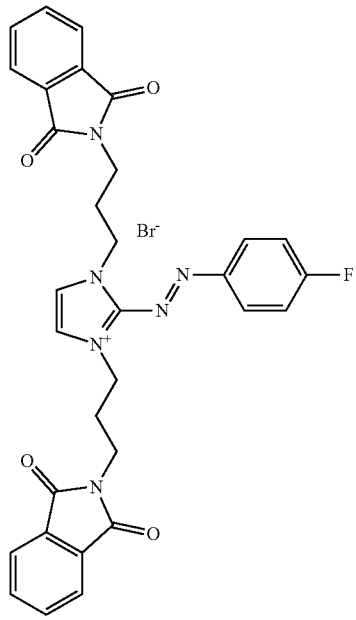

To a mixture of 3.8 g (20 mmol) 2-((4-fluorphenyl)diazenyl)-1H-imidazole and 3.4 g (40 mmol) sodium bicarbonate in 80 ml of acetonitrile was added 16.1 g (60 mmol) N-(3-bromopropyl)phthalimide. The mixture was refluxed for 60 hours. The formed precipitate was removed by filtration and the filtrate was concentrated under reduced pressure. The resulting residue was applied to flash chromatography to yield intermediate as brown solid.

Yield: 4.2 g (33%).

b) Step 2: 1,3-bis(3-(1,3-dioxo-1,3-dihydro-2H-isoindol-2-yl)propyl)-2-((E)-(4-dipentylaminophenyl)diazenyl)-1H-imidazol-3-ium bromide (102b)

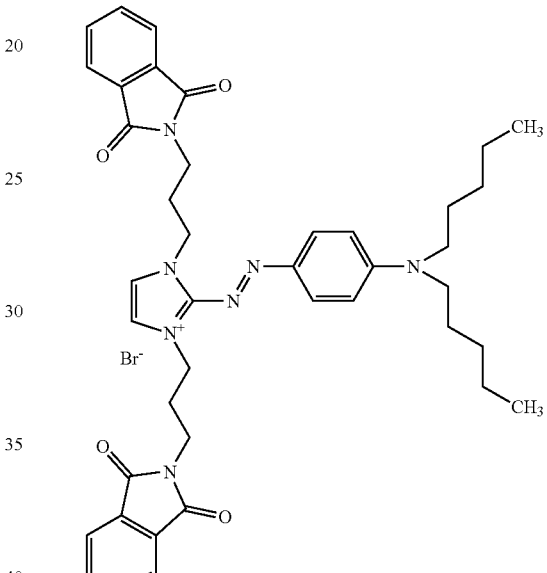

To a mixture of 1.94 g (3 mmol) crude intermediate from example 2a), 4.5 g (1.5 mmol) sodium bicarbonate in 2.5 ml of acetone and 10 ml of water was added 0.566 g (3.6 mmol) dipentylamine. The mixture was stirred at 20° C. for 3 hours. The mixture was diluted with water and extracted with dichloromethane. The crude product was purified with flash chromatography.

c) Final Step 2.3 g (2.94 mmol) was dissolved in isopropanol and 1.8 g (29.4 mmol) ethylenediamine was added. The mixture was refluxed for 5 hours. The crude product was purified by prep. HPLC with 0.1% trifluoroacetic acid added to the liquid phases to yield target compound (220 mg) as dark powder.

UV $\lambda_{max}$=538 nm.

$^1$H NMR (DMSO-d$_6$): δ=0.89 (t; 6H, CH$_3$), 1.30-1.37 (m; 8H, CH$_2$), 1.61 (m; 4H, CH$_2$), 2.17 (m, 4H, CH$_2$), 2.87 (m; 4H, CH$_2$), 3.52 (t; 4H, CH$_2$), 4.51 (t; 4H, CH$_2$), 6.95 (d; 2H, Aryl-H), 7.99 (s; 2H, Imidazoyl-H), 7.99 (d; 2H, Aryl-H), 8.35 (br; 6H, NH$_3$) ppm.

Example 3: (E)-2-((4-(bis(3-aminopropyl)amino)phenyl)diazenyl)-1,3-di-pentyl-1H-imidazol-3-ium bromide dihydro 2,2,2-trifluoroacetate
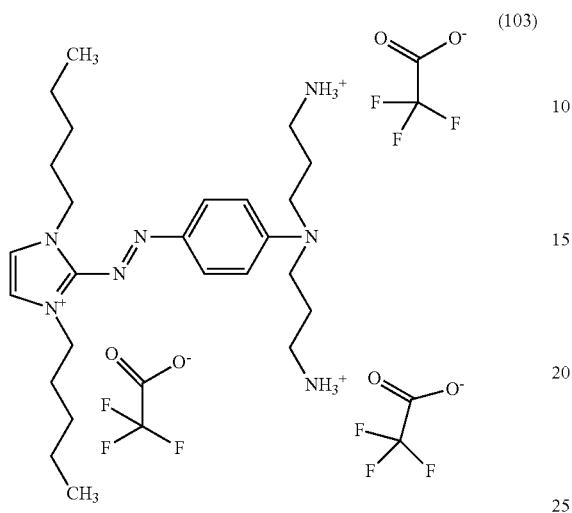
(103)
Synthesis Scheme of Example 3
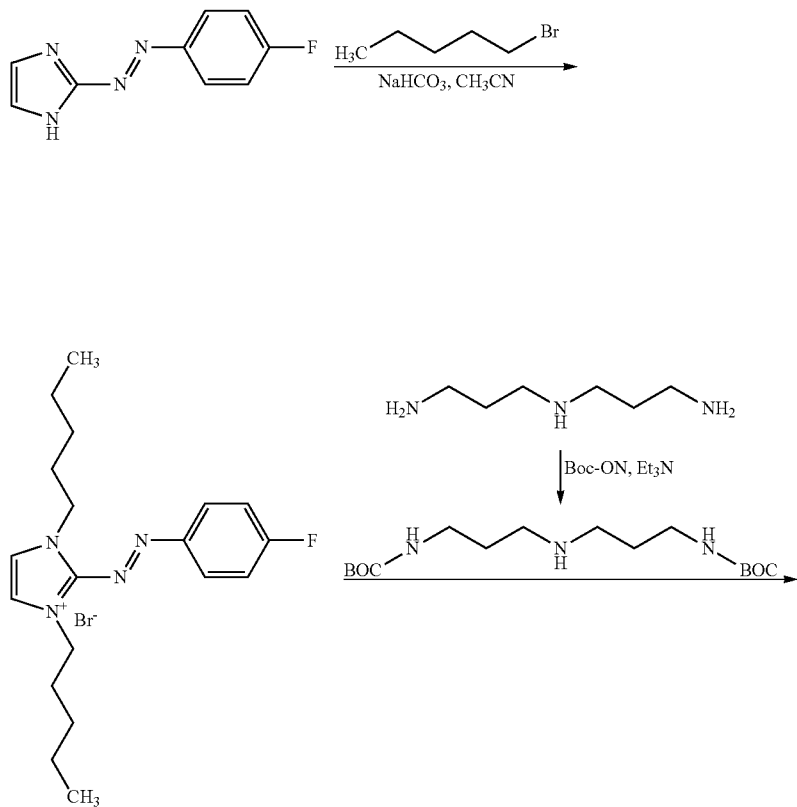

-continued

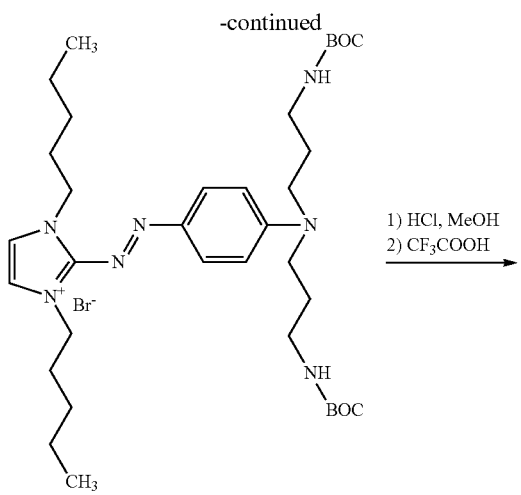

1) HCl, MeOH
2) CF₃COOH
→

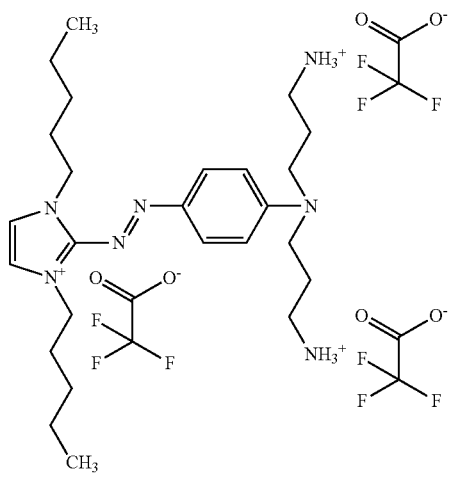

BOC-on =
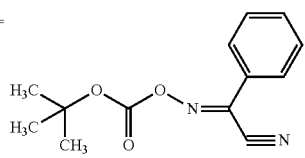

a) Step 1: (E)-2-((4-(fluorphenyl)diazenyl)-1,3-dipentyl-1H-imidazol-3-ium bromide (103a)

To a solution of 2.85 g (15 mmol) 2-((4-fluorphenyl)diazenyl)-1H-imidazole in 60 ml acetonitrile at 20° C. was added 3.78 g (45 mmol) sodium bicarbonate and 6.8 g (45 mmol) 1-bromopentane. The resulting reaction mixture was heated to reflux for 60 hours. The mixture was filtered to remove solid and the filtrate was concentrated under reduced pressure. The residue was purified to flash chromatography.

Yield: 1.6 g (25%), brownish solid.

$^1$H NMR (MeOD): δ=0.93 (t; 6H, CH₃), 1.43 (m; 8H, CH₂), 1.97 (m; 4H, CH₂), 4.61 (m; 4H, CH₂), 7.48 (m; 2H, Aryl-H), 8.00 (s; 2H, Imidazoyl-H), 8.22 (d; 2H, Aryl-H) ppm.

b) Step 2: (E)-2-((4-(bis(3((((1,1-dimethylethyl)oxy)carbonyl)amino)propyl)phenyl)diazenyl)-1,3-dipentyl-1H-imidazol-3-ium bromide

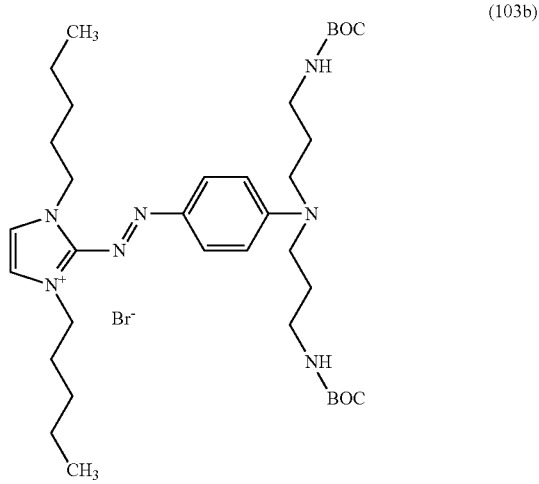 [SMILES: CCCCCn1cc[n+](CCCCC)c1/N=N/c1ccc(N(CCCNC(=O)OC(C)(C)C)CCCNC(=O)OC(C)(C)C)cc1 ; [Br-]]

(103b)

I)

Synthesis of di-tert butyl.(azanediylbis(propane-3,1-diyl))dicarbamate (1,9-bis boc 1,5,9-triazanonane)

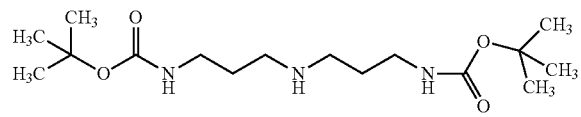 [SMILES: CC(C)(C)OC(=O)NCCCNCCCNC(=O)OC(C)(C)C]

To a mixture of 6.56 g (50 mmol) dipropylenetriamine, 7.08 g (70 mmol) triethylamine and 80 ml tetrahydrofuran at 0° C. was added a solution of 24.6 g (100 mmol) (2-tert-.butoxycarbonylox-imino)-2-phenylacetonitrile in 20 ml tetrahydrofuran dropwise. After addition, the reaction mixture was warmed to 20° C. and stirred for another 12 hours. The reaction mixture was concentrated to remove tetrahydrofuran, and the residue was diluted with 200 ml dichloromethane. The mixture was washed with 40 ml sodium hydroxide solution (10%), 40 ml of water and 40 ml of saturated sodium chloride solution. After washing, the organic phase was dried with anhydrous magnesium sulfate and then concentrated to give the crude product (12.4 g, white solid). This crude product was used directly in the next step without further purification.

II)

To a mixture of 1.59 g (3.87 mmol) (E)-2-((4-(fluorophenyl)diazenyl)-1,3-di-pentyl-1H-imidazol-3-ium bromide, 0.49 g (5.81 mmol) sodium bicarbonate in 8 ml acetone and 2.5 ml water was added 1.41 g (4.26 mmol) of di-tert butyl.(azanediylbis(propane-3,1-diyl)) in 2 ml acetone. The mixture was stirred at 20° C. for 12 hours. The mixture was diluted with 10 ml water and extracted three times with 50 ml of dichloromethane. The organic layers were washed with water and brine, dried and concentrated under vacuum. The residue (2.75 g) was used in the next step without further purification.

c) Final Step

To a solution of 2.74 g (3.80 mmol) from intermediate prepared in step 2 in 7 ml methanol was added 7 ml of 6M hydrochloric acid slowly. The resulting mixture was stirred at 20° C. for 2 hours. Then the mixture was heated to 60° C. for 2 additional hours. The reaction mixture was injected to preparative HPLC for purification with 0.1% trifluoro acetic acid added to the mobile phases. The liquid phases containing pure compound were collected and evaporated. The target molecule was isolated with trifluoracetate anions.

Yield: 1.3 g (43% yield for two steps).

$^1$H NMR (MeOD): δ=0.93 (m; 6H, $CH_3$), 1.3-1.5 (m; 8H, $CH_2$), 1.89 (m; 4H, $CH_2$), 2.12 (m; 4H, $CH_2$), 3.12 (m; 4H, $CH_2$), 3.77 (m; 4H, $CH_2$), 4.49 (t; 4H, $CH_2$), 7.11 (d; 2H, Aryl-H), 7.69 (s; 2H, Imidazoyl-H), 7.99 (d; 2H, Aryl-H) ppm.

UV $\lambda_{max}$=540 nm.

Example 4: (E)-2-((4-aminophenyl)diazenyl)-1,3-bis(3-aminopropyl)-1H-imidazol-3-ium trichloride

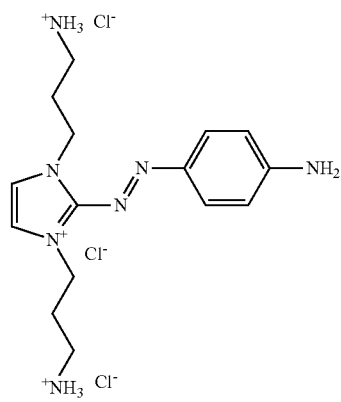

(104)

Synthesis Scheme of Example 4

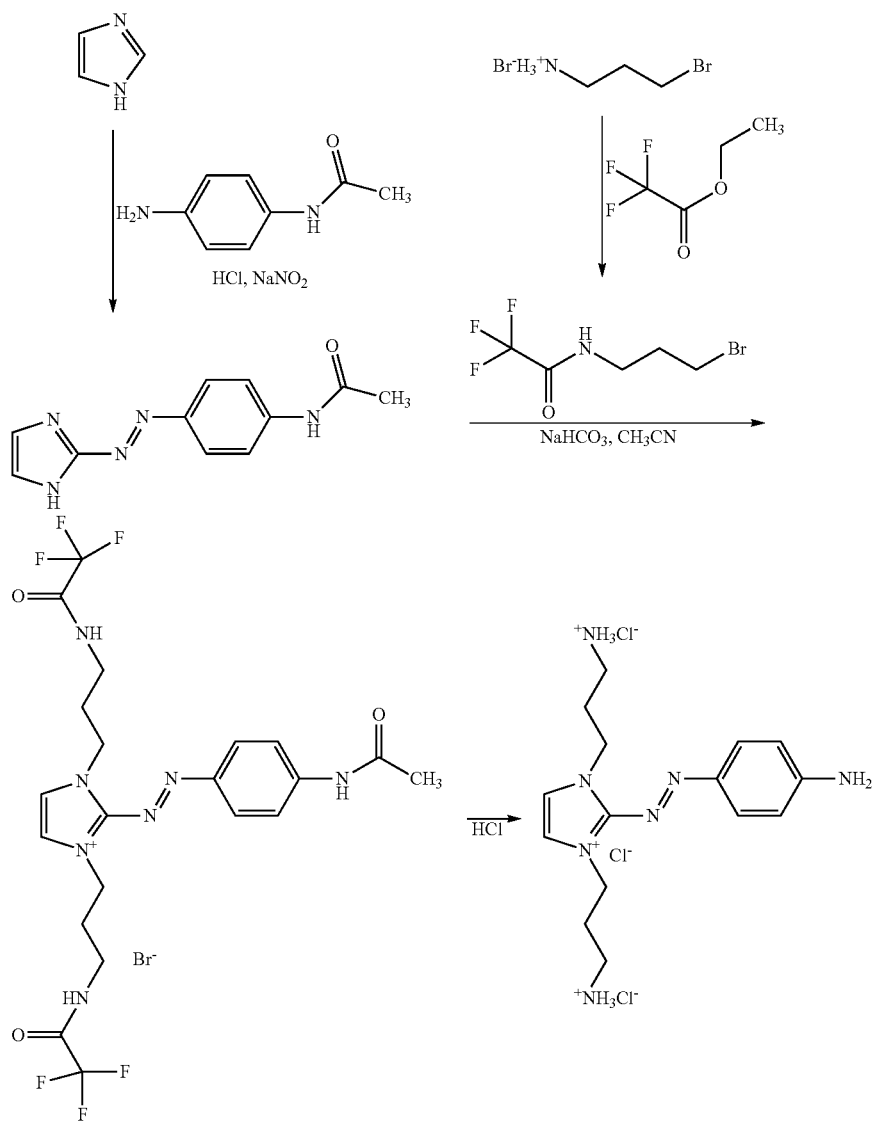

a) Step 1: N-[4-[(E)-1H-imidazol-2-ylazo]phenyl]acetamide (104a)

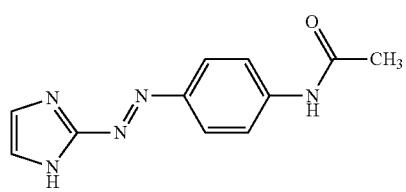

I)

Preparation of diazo compound: 30.45 g (0.2 mol) p-aminoacetanilide was suspended in 400 ml water. 49.2 g concentrated hydrochloric acid (37%) were added and cooled down to 0-5° C. Within 30 minutes, 49.9 ml of an aqueous sodium nitrite solution (4M) were added. The suspension was stirred for 1 hour at 0° C. An excess of nitrite was destroyed by the addition of amidosulfonic acid.

II)

Coupling component: 13.66 g (0.2 mol) imidazole were dissolved in 400 ml of water and cooled to 0-5° C. The solution was adjusted to pH10 by addition of 30% sodium hydroxide solution.

III)

Coupling: The cooled diazosolution prepared in I) was added portion wise within 45 minutes to the imidazole solution. The temperature of the reaction solution was kept between 0-5° C.; pH 10 was adjusted by addition of sodium hydroxide. The yellow reaction suspension was stirred 1 hour at 0-5° C., then warmed up to 20° C. and stirred for another 10 hours. A pH of 9.5 was adjusted (sodium hydroxide). The formed precipitate was collected by filtration, washed with 600 ml of warmed (50° C.) distilled water and dried in vacuum at 20° C.

Yield: 163 g, yellow solid.

¹H NMR (DMSO-d₆): δ=2.10 (s; 3H, CH₃); 7.30-7.8 (m; 6H, Aryl-H), 10.3 and 12.8 (s; br, each 1H, NH) ppm.

b) Step 2: 2-((E)-(4-(acetylamino)phenyl)diazenyl)-1,3-bis(3-((((1,1-dimethylethyl)oxy)carbonyl)amino)propyl)-1H-imidazol-3-ium bromide

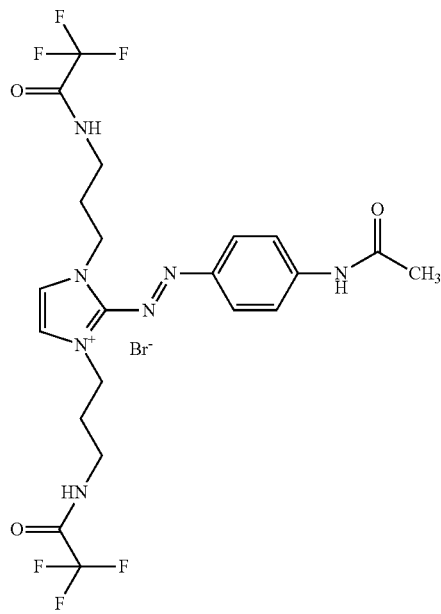

(104b)

I)

Synthesis of N-(3-bromopropyl)-2,2,2-trifluoroacetamide

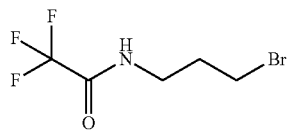 [SMILES: O=C(NCCCBr)C(F)(F)F]

To a cooled stirred solution of 64.4 g (0.297 mol) 3-bromopropylamine hydrobromide in 840 ml methanol at 00° C. was added 44 ml (32.1 g, 0.317 mol) triethylamine. Within 30 minutes, 45.5 g (0.32 mol) ethyl trifluoroacetate was added to the above reaction mixture dropwise. The mixture was stirred at 00° C. for 3 hours. Solvent was evaporated under reduced pressure. The residue was taken up in 1400 ml of dichloromethane and was washed with water (360 ml), sodium bicarbonate solution (twice with 150 ml) and brine (400 ml). The organic solution was evaporated to dryness.

Yield: 64 g (92%), colorless solid. This was used in the next step without further purification.

¹H NMR (CDCl₃): δ=2.20, 3.47 and 3.63 (m; each 2H, CH₂); 6.65 (s; br, NH) ppm.

II)

5 g (0.022 mol) intermediate prepared in 4a) were suspended in 200 ml acetonitrile. 15.3 g (0.065 mol) N-(3-bromopropyl)-2,2,2-trifluoroacetamide prepared above were added to this suspension. The product mixture was heated to reflux (60° C.). Then 3.66 g (0.043 mol) sodium bicarbonate were added. The product mixture was kept under reflux for 70 hours. The warm suspension was filtrated. The mother liquor was evaporated in vacuum; the obtained solid was treated with 200 ml dichloromethane. 10 ml of methanol and 15 ml of ethyl acetate were added. The precipitate was collected by filtration and washed with 10 ml of dichloromethane. The raw product was suspended in 250 ml water, filtrated and evaporated by freeze-drying.

Yield: 1.4 g (12%), dark orange solid.

¹H NMR (DMSO-d₆): δ=2.0-2.2 (m; signals overlapping, 7H, CH₃ and CH₂), 3.33 (m, 4H, CH₂), 4.50 (m; 4H, CH₂), 6.95 (d; 2H, Aryl-H), 8.0-8.2 (m; signals overlapping, 4H, Aryl-H), 7.99 (d; 2H, Aryl-H, Imidazoyl-H), 9.59 (m; 2H, N$\underline{H}$CF₃), 10.71 (s, 1H, N$\underline{H}$CO) ppm.

c) Step 3 (Final Step)

1.3 g (2 mmol) intermediate from 4b, II) was suspended in 26 ml hydrochloric acid (3M) and stirred for 3 hours at 90° C. The obtained product solution was evaporated in vacuum. Again, 26 ml hydrochloric acid was added, the obtained solution heated to 90° C. and kept at this temperature for 1 hour. Then, the solution was evaporated until dryness. The raw product is treated with small amount of dichloromethane, filtered-off and dried in high vacuum at 20° C.

Yield: 350 mg (80%), red solid.

UV λ$_{max}$=498 nm.

¹H NMR (D₂O): δ=2.23, 3.04 and 4.48 (m; 12H, CH₂), 6.95 (m; 2H, Aryl-H), 7.11 (d; 2H, Aryl-H), 7.56 (s; 2H, Imidazoyl-H), 7.88 (d; 2H, Aryl-H) ppm.

Example 5: (E)-1,3-bis(3-N,N-dimethylaminopropyl)-2-((4-(dimethylamino)phenyl)-diazenyl)-1H-imidazol-3-ium bis-trifluoracetate

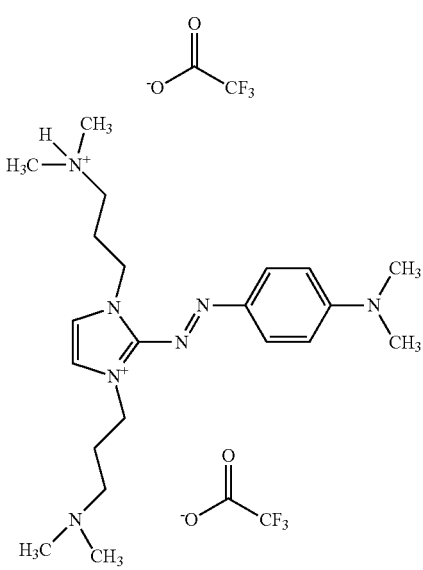

(105)

Synthesis Scheme of Example 5

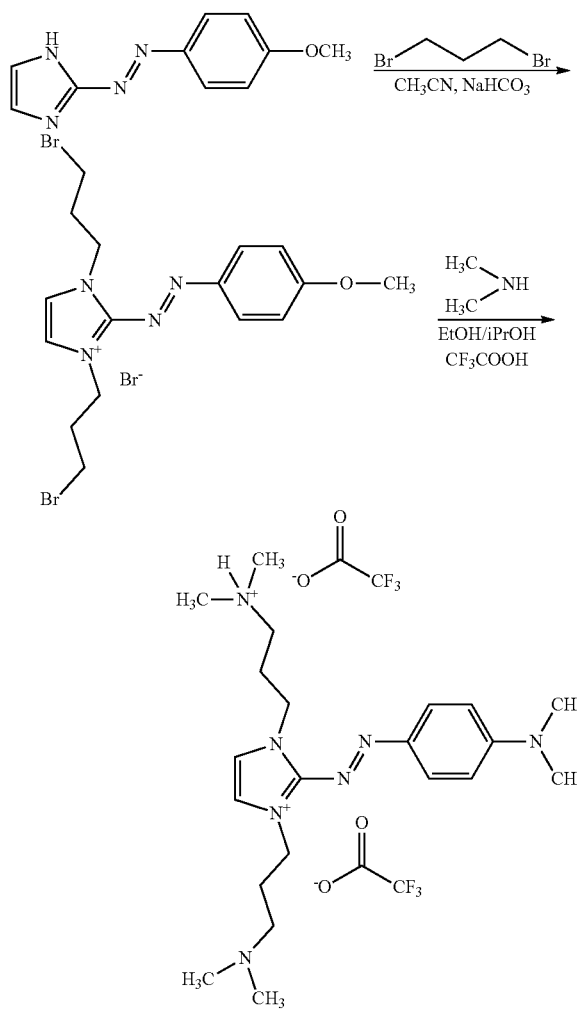

a) Step 1: (E)-[1,3-bis(3-bromopropyl)imidazol-1-ium-2-yl]-(4-methoxyphenyl)diazene; bromide 59.3 g (296.9 mmoles) dibromopropane and 12.47 g (148.45 mmoles) sodium bicarbonate were suspended in 100 ml of acetonitrile and heated to 70° C. 30 g (149 mmol) (E)-1H-imidazol-2-yl-(4-methoxyphenyl)diazene [prepared according to L. Skulski, D. Maciejewska, Polish J. Chem., 59 (1), 37 (1985)] was suspended in 100 ml acetonitrile and added in portions to the hot reaction mixture. The temperature was then raised to 90° C. and stirring was continued for 21 hours. The reaction mixture was then cooled to 25° C. and filtered. Evaporation of the filtrate provided 45 g of a black oil. The raw product was purified by column chromatography (silica gel, with 2% methanol in pure dichloromethane and increased 2% methanol every 2 liters until the product eluted with 6% methanol/dichloromethane). The product fractions were combined providing 0.90 g (8% yield) of the product.

b) Step 2 (Final Step)

870 mg of intermediate from step 1 (1.508 mmoles) was reacted with isopropanol (1 ml) and 40% ethanolic dimethyl amine solution (1.5 ml, 13.38 mmoles). The mixture was refluxed for 1 hour. The reaction was subsequently cooled and evaporated to dryness. The crude product was dissolved in 6 ml of water. Small portions of this solution, ranging from 0.5 ml to 2.0 ml, were purified by preparative HPLC (Column: Waters Xbridge Prep $C_{18}$, 5 µm, OBD 30×250 mm). The pure fractions from each run were combined to provide 540 mg (58% yield) of target compound.

$^1$H NMR (CD$_3$OD): δ=2.60 (dt; 4H, CH$_2$); 2.92 (s; 12H, CH$_3$), 3.32 (m; 10H, CH$_3$, CH$_2$), 4.55 (t; 4H, CH$_2$), 7.00 (d; 2H, CH), 7.65 (s; 2H, HC=CH), 8.03 (d; 2H, CH) ppm. ESI-MS m/z 386.35 [M$^+$].

Example 6: 4-[(E)-[3-(3-aminopropyl)-1-methyl-imidazol-2-yl]azo]-N,N-dimethyl-aniline chloride

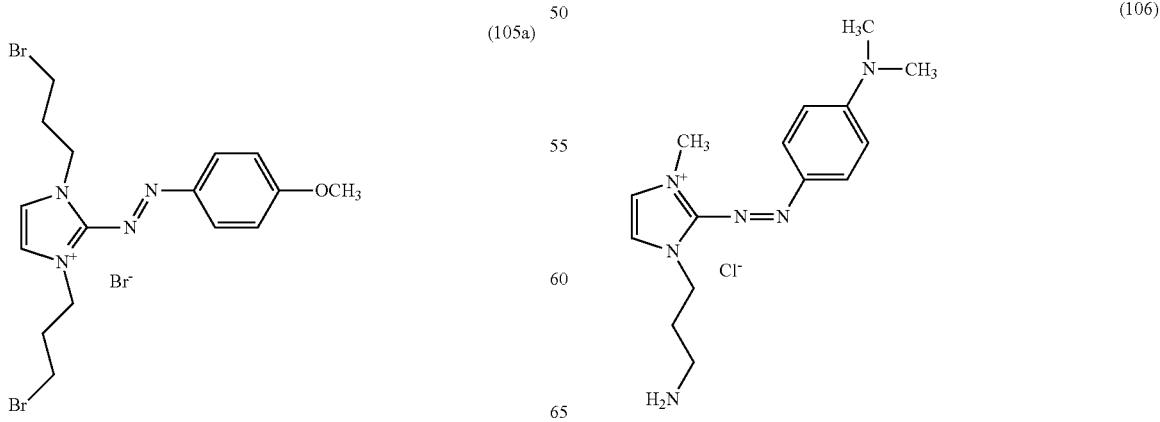

Synthesis Scheme of Example 6
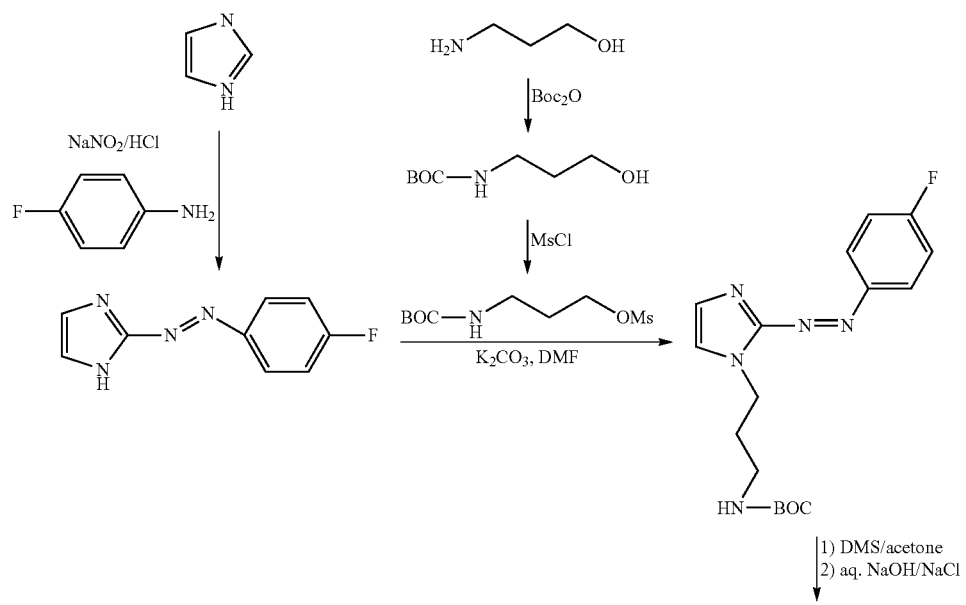
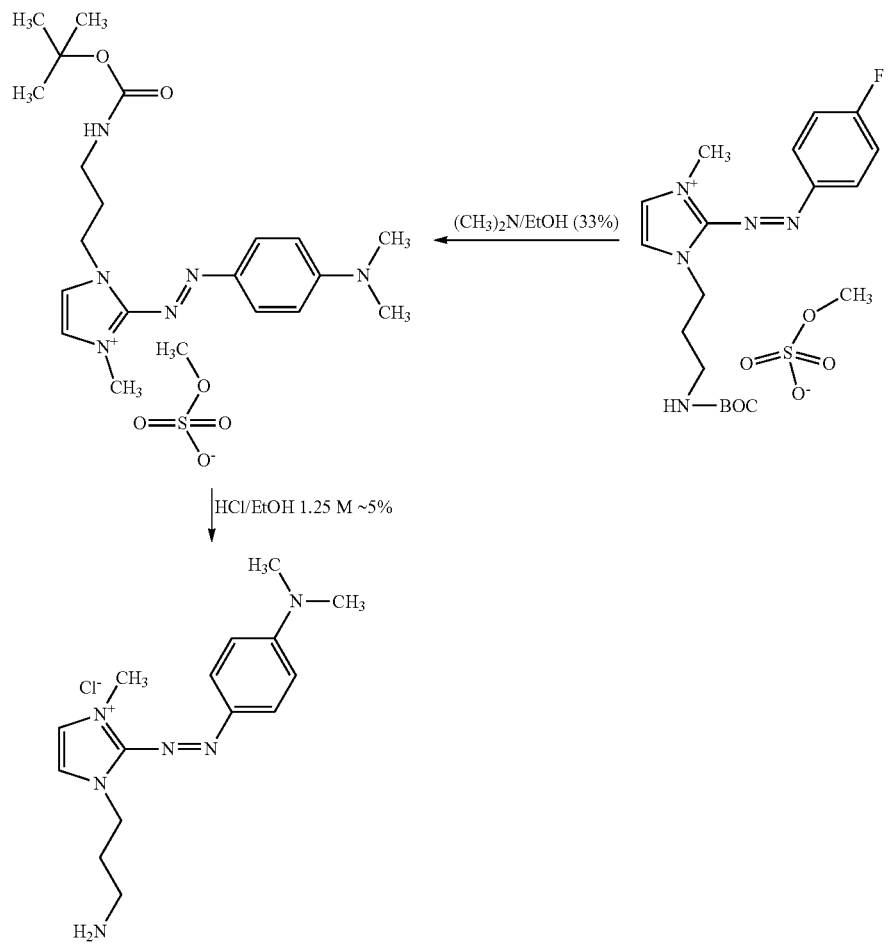

a) tert-butyl N-[3-[2-[(E)-(4-fluorophenyl)azo]imidazol-1-yl]propyl]carbamate

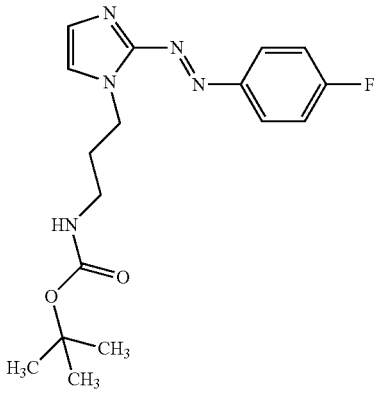

(106a)

11.5 g (0.06 mol) 2-((4-fluorphenyl)diazenyl)-1H-imidazole and 16.9 g (0.122 mol) potassium carbonate were suspended in 300 ml of N,N-dimethylformamide. To that suspension, a solution of 18.7 g (0.074 mol) 3-(tert-butoxycarbonylamino)propyl methanesulfonate [prepared according to literature: Ganguli et al., Bioorg. Med. Chem. Lett. 24 (2014) 4198] in 100 ml of N,N-dimethylformamide was added within 10 minutes. The reaction mixture was heated to 110° C. for three hours. Afterwards the reaction mixture was poured into 500 g of ice. The reaction was stirred at 20° C. for 10 hours to become an orange suspension. The formed precipitate was collected by filtration (suction filter), washed with 500 ml of water and dried in high vacuum at 30° C. Yield: 17.2 g, yellow solid (82%).

$^1$H NMR (DMSO-d$_6$): δ=1.32 (t; 9H, CH$_3$), 1.95 (m; 2H, CH$_2$), 4.41 (m; 2H, CH$_2$), 6.90 (m; 1H, NH), 7.25 (m; 1H, Aryl-H), 7.40 (m; 2H, Aryl-H), 7.65 (s; 2H, Imidazoyl-H), 8.0 (m; 2H, Aryl-H) ppm.

b) Step 2: tert-butyl N-[3-[2-[(E)-(4-fluorophenyl)azo]-3-methyl-imidazol-1-yl]propyl]carbamate methyl sulfate

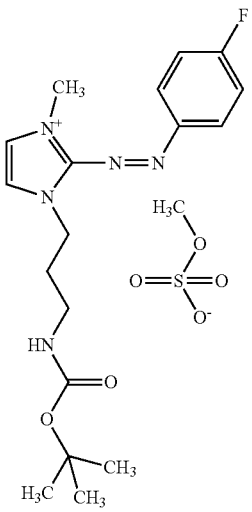

(106b)

12.4 g intermediate prepared in example 6a) was suspended in 150 ml of acetone and stirred at 20° C. 4.95 g (0.039 mol) dimethylsulfate is added dropwise within 20 minutes. The reaction mixture was stirred for 15 hours at 20° C. Then the solution was evaporated in vacuum and treated with 250 ml of distilled water. The pH was adjusted to 9 by addition of 1 M sodium hydroxide solution. The product was precipitated by addition of 250 ml brine. The formed precipitate was filtered-off and washed with brine. The raw product was suspended in ethanol, collected by filtration and dried in high vacuum at 30° C.

Yield: 13.2 g (78%), orange solid.

UV λ$_{max}$=535 nm.

$^1$H NMR (DMSO-d$_6$): δ=1.32 (t; 9H, CH$_3$), 1.95 (m; 2H, CH$_2$), 3.03 (m; 2H, CH$_2$), 4.13 (s; 3H, CH$_3$), 4.52 (m; 2H, CH$_2$), 7.05 (m; 1H, NH), 7.56, 8.15 and 8.25 (m; each 2H, Aryl-H) ppm.

c) Step 3: tert-butyl N-[3-[2-[(E)-[4-(dimethylamino)phenyl]azo]-3-methyl-imidazole-1-yl]propyl]carbamate; methyl sulfate

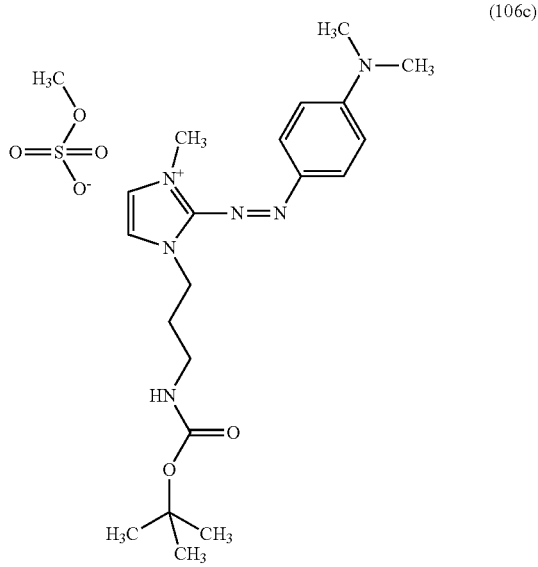

(106c)

Under stirring, 13.1 g (0.028 mol) intermediate prepared in 6b) was dissolved in 250 ml of acetonitrile. The solution was filtrated and 5.58 g (0.055 mol) triethylamine were added. Then, a solution of 5.28 g (0.039 mol) ethanolic dimethylamine (33%) was added dropwise within 5 minutes. The product mixture was stirred at 20° C. for 12 hours. Afterwards, the solvent was evaporated in vacuum to give 9.8 g (71%) of a violet solid which was directly used for the final step.

$^1$H NMR (D$_2$O): δ=1.32 (t; 9H, CH$_3$), 1.85 (m; 2H, CH$_2$), 3.00 (m; 2H, CH$_2$), 3.05 (s; 6H, CH$_3$), 3.76 (s; 3H, CH$_3$), 4.13 (m; 2H, CH$_2$), 6.61 (d; 2H, Aryl-H), 7.25 and 7.31 (m; each 1H, Imidazoyl-H), 7.59 (d; 2H, Aryl-H) ppm.

d) Final Step

To a stirred solution of 9.7 g (0.019 mmol) intermediate prepared in 6c) in 100 ml ethanol was added dropwise within 25 minutes 256 g of an ethanolic HCl-solution (2.5 M). The reaction solution was stirred at 20° C. for 72 hours. Afterwards, the solution was evaporated in vacuum, treated with 100 ml of distilled water and adjusted to pH8 by addition of sodium hydroxide solution (1M). The aqueous solution was freeze-dried to yield 9.8 g of a dark red solid which contained sodium chloride.

$^1$H NMR (D$_2$O): δ=2.15 (m; 2H, CH$_2$), 3.00 (m; 2H, CH$_2$), 3.15 (s; 3H, CH$_3$), 3.85 (s; 3H, CH$_3$), 4.35 (m; 2H, CH$_2$), 6.75 (d; 2H, Aryl-H), 7.31 and 7.38 (m; 1H, Imidazoyl-H), 7.76 (d; 2H, Aryl-H) ppm.

Example 7: 4-[(E)-[3-(5-aminopentyl)-1-methyl-imidazol-2-yl]azo]-N,N-dimethylaniline chloride
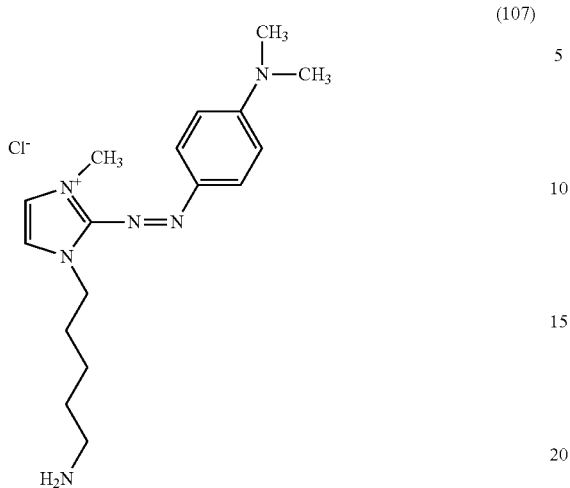
Synthesis Scheme of Example 7
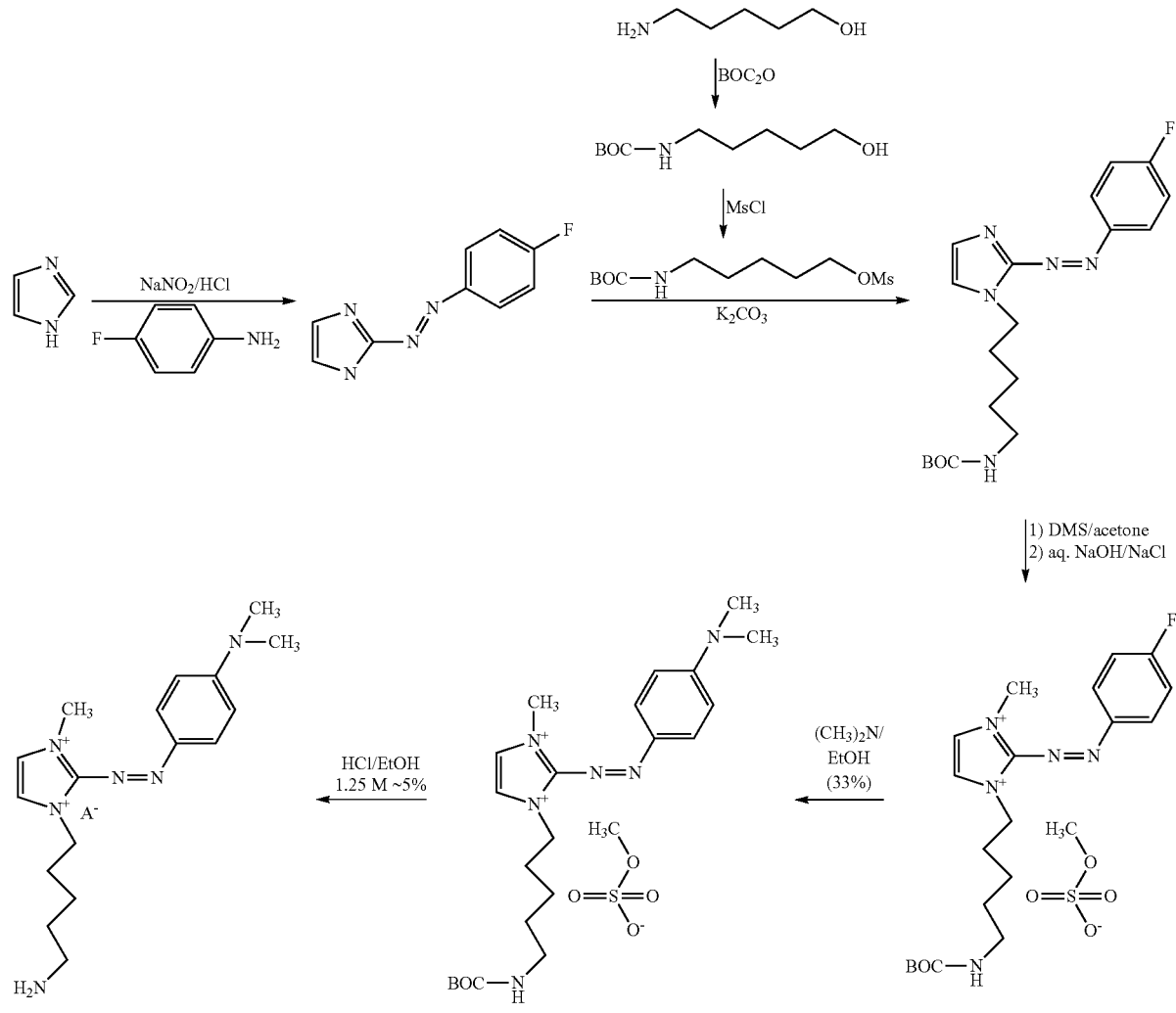

BOC = 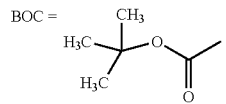

a) Step 1: tert-butyl N-[5-[2-[(E)-(4-fluorophenyl)azo]imidazol-1-yl]pentyl]carbamate

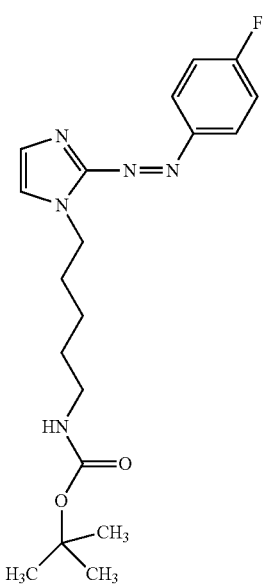

(107a)

Under stirring, 13.6 g (0.072 mol (E)-(4-fluorophenyl)-(1H-imidazol-2-yl)diazene and 18.2 g (0.0132 mol) potassium carbonate were suspended in 300 ml of N,N-dimethylformamide at 20° C. To that solution, a solution of 22.19 g (0.079 mmol) 3-(tert-butoxycarbonylamino)pentyl methanesulfonate (prepared from 1-aminopentanol in two steps according to literature cited in example 6) in 200 ml N,N-dimethylformamide were added dropwise within 10 minutes. The product mixture was heated to 110° C. and kept at that temperature for 4 hours. The reaction mixture was poured into 600 g of ice and stirred for 30 minutes. The formed precipitate was removed by filtration. The mother liquor was stirred at 20° C. for 12 hours. The formed orange precipitate was collected by filtration and dried in high vacuum. Yield: 20.2 g (75%), brownish solid.

$^1$H NMR (DMSO-d$_6$): δ=1.24 (m; 2H, CH$_2$), 1.39 (t; 9H, CH$_3$), 1.42 (m; 2H, CH$_2$), 1.81 (m; 2H, CH$_2$), 2.87 (m; 2H, CH$_2$), 4.39 (m; 2H, CH$_2$), 6.74 (m; 1H, NH), 7.26 (s; 1H, Imidazoyl-H), 7.44 (m; 2H, Aryl-H), 7.61 (s; 1H, Imidazoyl-H), 7.96 (m; 2H, Aryl-H) ppm.

UV λ$_{max}$=535 nm.

b) Step 2: tert-butyl N-[5-[2-[(E)-(4-fluorophenyl)azo]-3-methyl-imidazol-1-yl]pentyl]carbamate methyl sulfate

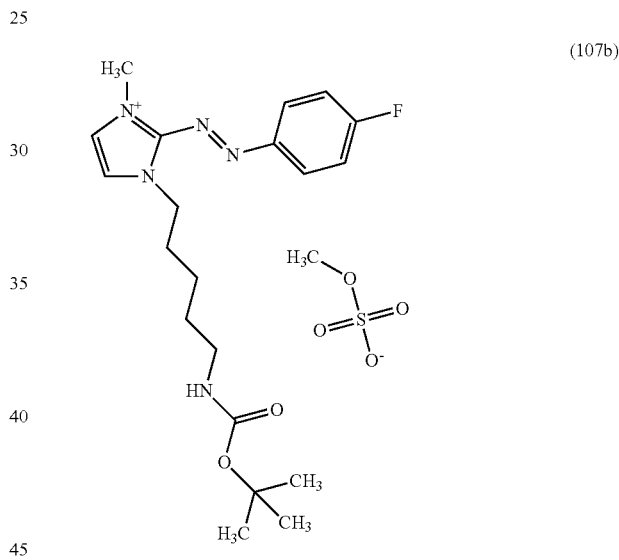

(107b)

Under stirring, 9.4 g (0.024 mol) intermediate from 7a) were dissolved in 150 ml acetone. The solution was treated with 3.5 g (0.028 mol) dimethylsulfate. The reaction and work-up was done according to the procedure described in example 6b).

Yield: 13.7 g raw product which was used directly for the next step.

$^1$H NMR (DMSO-d$_6$): δ=1.3-1.4 (m; signal overlapping, 13H, CH$_2$ and CH$_3$), 1.82 (m; 2H, CH$_2$), 2.88 (m; 2H, CH$_2$), 4.09 (s; CH$_3$), 4.50 (m; 2H, CH$_2$), 6.77 (m; 1H, NH), 7.58 (m; 2H, Aryl-H), 8.05 and 8.10 (s; each 1H, Imidazoyl-H), 8.21 (m; 2H, Aryl-H) ppm.

c) tert-butyl N-[5-[2-[(E)-[4-(dimethylamino)phenyl]azo]-3-methyl-imidazol-1-yl]pentyl]-carbamate methyl sulfate Example 8: 4-[(E)-[1,3-bis(4-aminobutyl)imidazole-1-ium-2-yl]azo]-N,N-dimethyl-aniline bromide

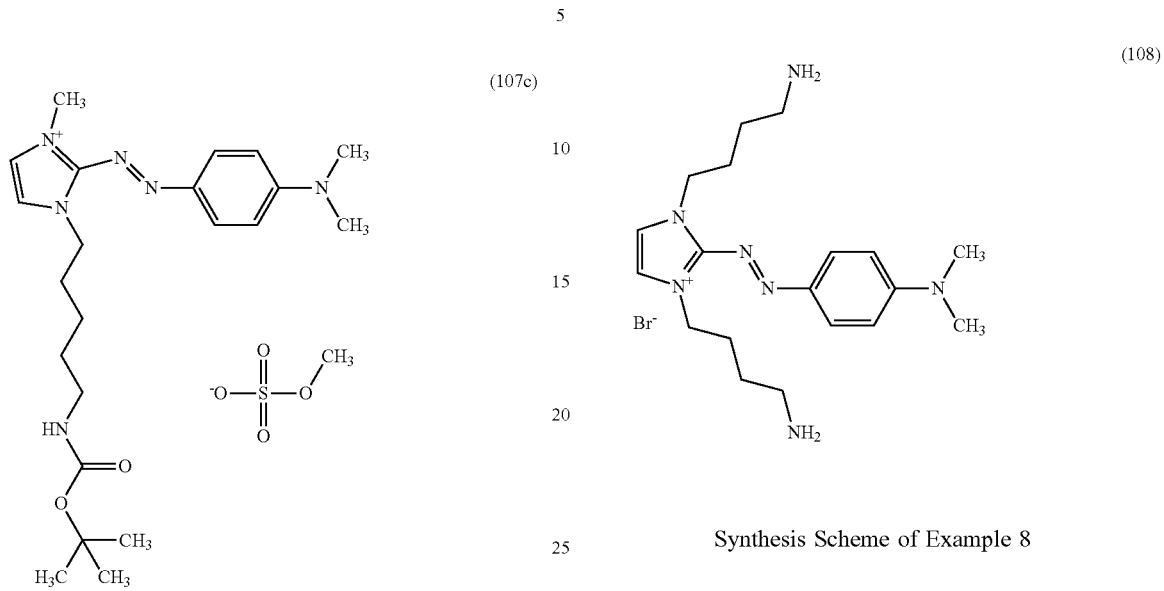

Synthesis Scheme of Example 8

A solution of 13.7 g (0.027 mol) crude intermediate from 7b) in 200 ml acetonitrile was treated with 5.55 g (0.055 mol) N,N-triethylamine and 5.24 g (0.038 mmol) of an ethanolic dimethylamine solution (33%). The reaction and work-up was done as described in example 6c.

Yield: 18.5 g crude material.

$^1$H NMR (DMSO-$d_6$): δ=1.25-1.45 (m; signal overlapping, 13H, CH$_2$ and CH$_3$), 1.75 (m; 2H, CH$_2$), 2.89 (m; 2H, CH$_2$), 3.23 (s; 6H, CH$_3$), 3.96 (s; CH$_3$), 4.39 (m; 2H, CH$_2$), 6.76 (m; 1H, NH), 6.96 (m; 2H, Aryl-H), 7.75 and 7.80 (s; each 1H, Imidazoyl-H), 7.88 (m; 2H, Aryl-H) ppm.

d) Step 4 (Final Step)

24.2 g (0.046 mol) crude intermediate from 7c) in 250 ml ethanol was treated with 465 g ethanolic hydrochloric acid (2.5M). The reaction and work-up was done according to the procedure given in example 6d. Yield: 17.9 g, contained NaCl.

$^1$H NMR (D$_2$O): δ=1.35, 1.58 and 1.77 (m; each 2H, 3×CH$_2$), 2.92 (m; 2H, CH$_2$), 3.12 (s; 6H, CH$_3$), 3.82 (s; 3H, CH$_3$), 4.19 (m; 2H, CH$_2$), 6.69 (d; 2H, Aryl-H), 7.20 and 7.25 (m; each 1H, Imidazoyl-H), 7.68 (d; 2H, Aryl-H) ppm.

a) Step 1: 4-[(E)-[1,3-bis(4-bromobutyl)imidazol-1-ium-2-yl]azo]-N,N-dimethyl-aniline bromide

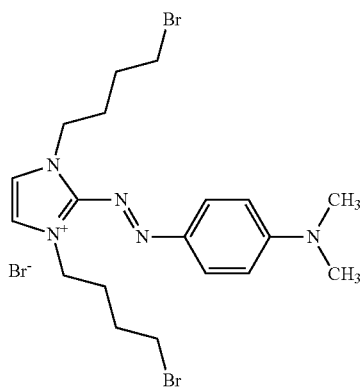

(108a)

A mixture of 6.5 g (0.030 mol) 1,4-dibromobutane and 1.3 g (0.015 mol) sodium bicarbonate in 20 ml acetonitrile was heated to 65° C. Within 2 hours, a suspension of 1.0 g (0.005 mol) 4-[(E)-1H-imidazol-2-ylazo]-N,N-dimethylaniline prepared in example 1a) in 30 ml acetonitrile was added. The product mixture was heated to 85° C. and kept at this temperature for 12 hours. The production mixture was filtrated. The residue was suspended in acetonitrile for 30 minutes and again filtered-off. Both mother liquors were combined and evaporated in vacuum to give a dark red liquid. The raw product was crystallized with a mixture of acetonitrile/ethyl acetate. Yield: 1.24 g (47%) red sticky solid.

b) Step 2: Final Compound 1.24 g (0.002 mol) intermediate 8 a) were suspended in 20 ml water and stirred at 20° C. Around 20 ml of an ammonia solution in dioxane (30%) were added. The product mixture was heated to 75° C. for four hours. Then, the red suspension was cooled down to 20° C. and evaporated to dryness.

Yield: 1.23 g, red, sticky solid, contained sodium bromide.

Example 9: 2-((4-(bis(2-ammonioethyl)amino)phenyl)diazenyl)-1,3-dimethyl-1H-imidazol-3-ium dichloride iodide Synthesis Scheme of Example 9

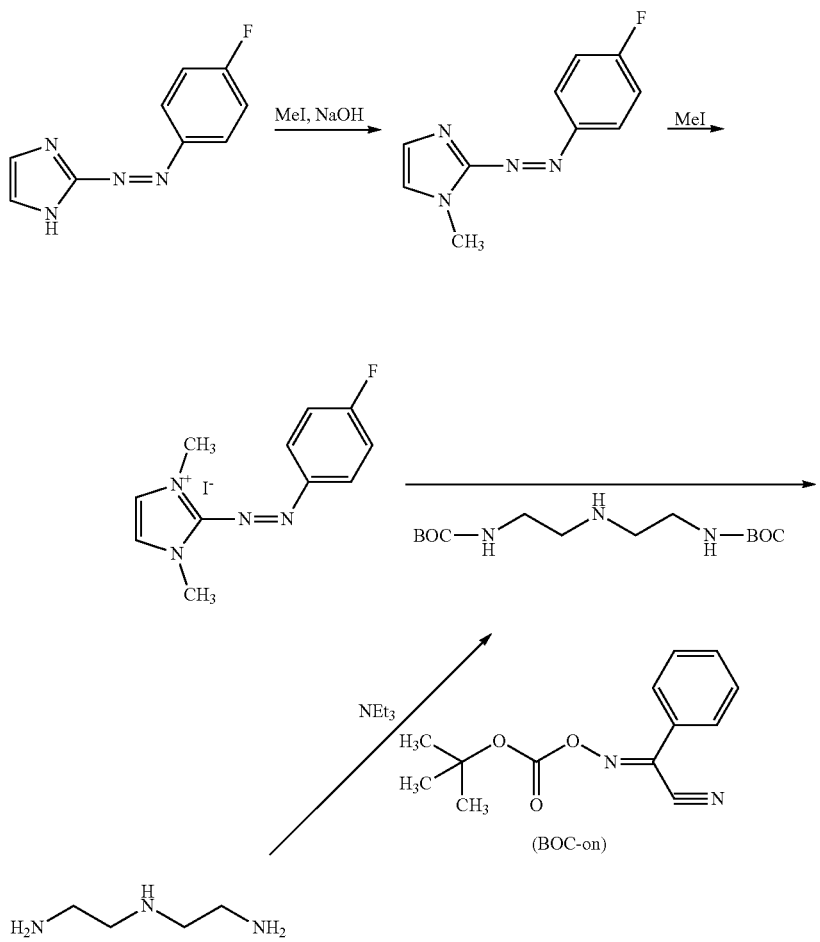

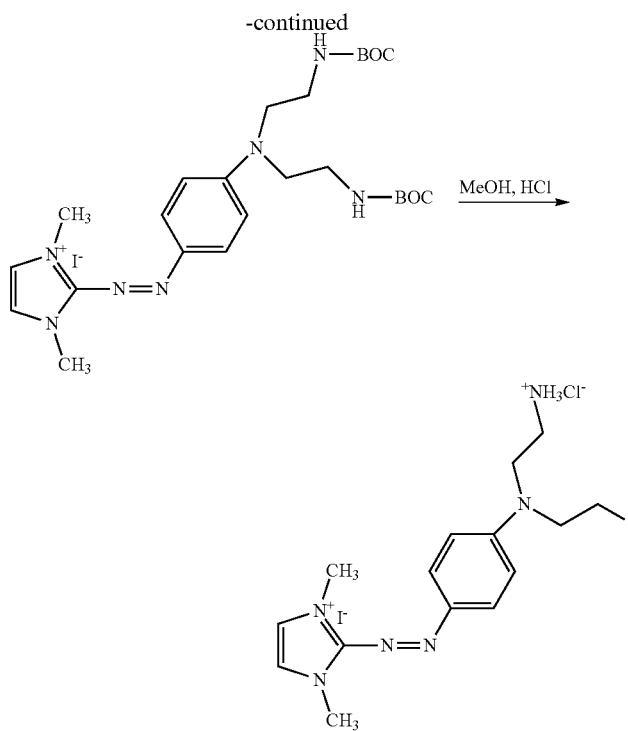

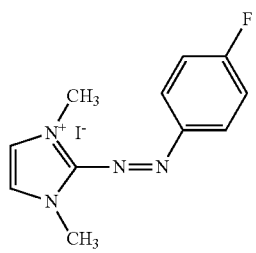

a) Step 1: 2((4-fluorophenyl)diazenyl)-1,3-dimethyl-1H-imidazol-3-ium iodide

I)

Monomethylation: A mixture of 300 g (1.58 mol) 2-((4-fluorphenyl)diazenyl)-1H-imidazole, 63 g (1.58 mol) sodium hydroxide pellets in 660 ml of a mixture of THF/water (600 ml/60 ml) was prepared under stirring. The reaction mixture was cooled to 0° C. Then 244 g (1.58 mol) methyl iodide was added to the mixture dropwise, keeping the inner temperature below 0° C. The reaction mixture was warmed to 20° C. and continued to stir for another two hours after methyl iodide had been added completely. The reaction mixture was concentrated under reduced pressure to remove tetrahydrofuran. Then the residue was poured into 2 liters of ice water. This suspension was stirred for another 30 minutes. Then the solid was filtered off. The residue was washed with water (500 ml, twice; the wet crude product was dried in vacuum at 40° C. for 12 hours. The product was obtained as a brown solid (196 g, 60%) which was used for the next step directly without further purification.

II)

Bismethylation: 195 g (0.96 mol) of the 2-((4-fluorophenyl)diazenyl-1-methyl-1H-imidazole from I), were suspended in a mixture of 500 ml acetonitrile and 100 ml methanol in a 1000 ml three-necked bottle equipped with mechanical stirrer and thermometer. The reaction mixture was stirred at 20° C., and then 272 g (1.92 mol) methyliodide was added to the mixture dropwise within 1 hour. The reaction mixture was continued to stir for another 12 hours at 20° C. after methyl iodide had been added completely. The reaction mixture was poured into 1 l of ethyl acetate. This suspension was stirred for another 20 minutes. Then the solid was filtered and the filter residue was washed with ethyl acetate (250 ml, twice), the crude product was dried in vacuum at 40° C. The product was obtained as a brown solid (290 g, 76%) which was used for the next step directly without further purification.

$^1$H NMR (DMSO-$d_6$): δ=4.10 (s; 6H, CH$_3$), 7.55-7.61 (m; 2H, Aryl-H), 8.05 (s; 2H, Aryl-H), 8.21-8.24 (m; 2H, Aryl-H) ppm.

b) Step 2: 2-((4-(bis(2-(tert-butoxycarbonylamino) ethyl)amino)phenyl)diazenyl)-1,3-dimethyl-1H-imidazol-3-ium dichloride iodide

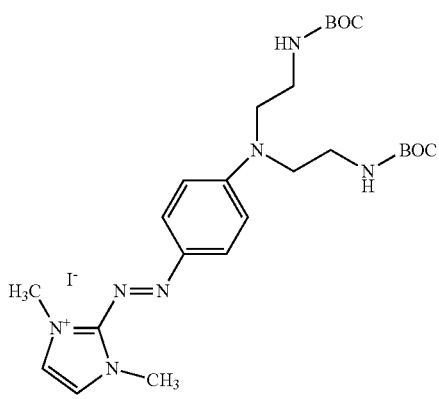

I)

tert-butyl N-[2-[2-(tert-butoxycarbonylamino)ethylamino]ethyl]carbamate

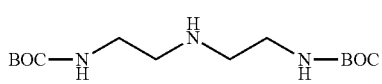

25 g (0.243 mol) N1-(2-aminoethyl)ethane 1,2-diamine and 34.4 g (0.343 mol) triethylamine were suspended in 300 ml THF. The reaction mixture was stirred at 0° C. under argon atmosphere, then a solution of 118.4 g (0.485 mol) (2-tert.-butoxycarbonyloximino)-2-phenylacetonitrile in 100 ml THF was added dropwise within two hours. After addition, the reaction mixture was warmed to 20° C. and stirred for another 12 hours. The reaction mixture was concentrated to remove the THF, and the residue was diluted with 500 ml of dichloromethane. The mixture was washed with 10% aqueous sodium hydroxide solution (100 ml, three times), 100 ml of water and 100 ml of brine. After washing, the organic phases were dried with anhydrous magnesium sulfate. Finally, the organic phases were evaporated to dryness to give 60 g (82%) of crude product as colorless oil. This crude product was used in the next step without purification.

$^1$H NMR (DMSO-$d_6$): δ=1.44 (s; 18H, CH$_3$), 2.72 (m; 4H, CH$_2$), 3.20-3.22 (m; 4H, CH$_2$), 5.04 (br, NH) ppm II) 72 g (0.208 mol) 2-((4-fluorophenyl)diazenyl)-1,3-dimethyl-1H-imidazol-3-ium iodide and 26.6 g (0.317 mol) sodium bicarbonate were suspended in a mixture of 425 ml acetone and 125 ml of water at 20° C. Then the reaction mixture was cooled to 0° C. and stirred for 30 minutes under a nitrogen atmosphere. A solution of 32 g (0.0213 mol) tert.-butyl 2,2'-azanediylbis(ethane-2,1-diyl)dicarbamate prepared above in 100 ml acetone was added to the mixture slowly. The solution was warmed to 20° C. and continued to stir for another 12 hours. Then the reaction mixture was diluted with 300 ml of dichloromethane and poured into a separatory funnel and washed with water (100 ml, five times). The organic phase was dried and contrated to give a crude red solid. The crude product was purified by silica gel chromatography eluted with dichloromethane/methanol (40:1).

Yield: 42 g (63%), red solid.

$^1$H NMR (DMSO-$d_6$): δ=1.36 (s; 18H, CH$_3$), 3.17 (m; 4H, CH$_2$), 3.5-3.6 (m; 4H, CH$_2$), 3.97 (s; CH$_3$), 7.04-7.09 (m, 4H, Aryl-H), 7.73 (s; 2H, Imidazoyl-H) ppm.

c) Step 3 (Final Step)

42 g (0.0668 mol) of tert-butyl N-[2-[2-(tertbutoxycarbonylamino)ethylamino]ethyl]carbamate were dissolved in 150 ml of methanol. The reaction mixture was stirred at 20° C. for three hours while HCl gas was bubbled into the reaction system. The reaction mixture was stirred at 20° C. for another 3 hours, then concentrated to give a red solid. The crude product was purified by reversed phase chromatography (C$_{18}$ column) eluted with water/ethanol gradient (100~10/1).

Yield: 16 g (59%), red solid.

$^1$H NMR (D$_2$O): δ=3.2-3.3 (m; 4H, CH$_2$), 3.8 (s; 6H, CH$_3$), 3.8-3.9 (m; 4H, CH$_2$), 6.8 (m; 2H, Aryl-H), 7.3 (s; 2H, Imidazoyl-H), 7.64 (d; 2H, Aryl-H) ppm.

Example 10: 2-((4-(bis(3-ammoniopropyl)amino)phenyl)diazenyl)-1,3-dimethyl-1H-imidazol-3-ium dichloride iodide

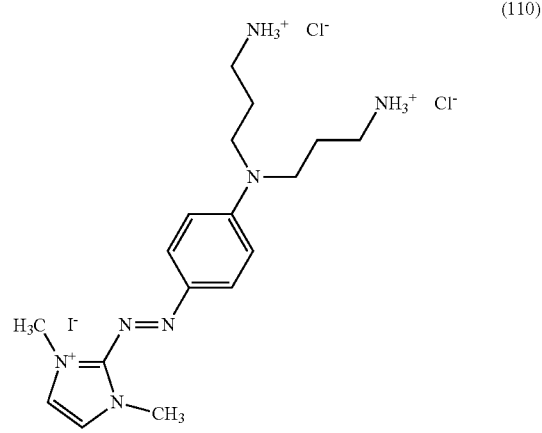 [SMILES: [Cl-] ; Cn1cc[n+](C)c1/N=N/c1ccc(N(CCC[NH3+])CCC[NH3+])cc1 ; [I-] ; [Cl-]]

Synthesis Scheme of Example 10

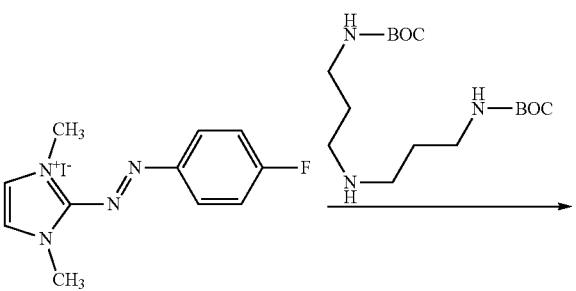

-continued

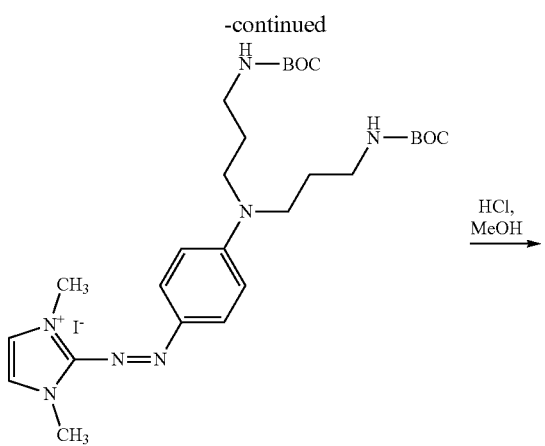

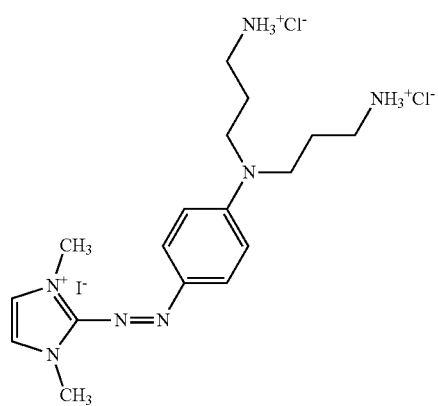

a) Step 1: 2-((4-(bis(2-(tert-butoxycarbonylamino-propyl)amino)phenyl)diazenyl)-1,3-dimethyl-1H-imidazol-3-ium dichloride iodide (110a)

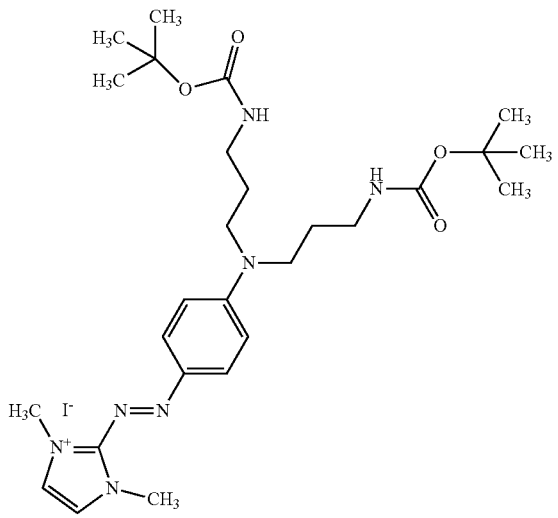

72 g (0.208 mol) 2-((4-fluorophenyl)diazenyl)-1,3-dimethyl-1H-imidazol-3-ium iodide prepared in example 9, step 2 and 26.6 g (0.317 mol) sodium bicarbonate were stirred in acetone/water (4:1) mixture. The reaction mixture was cooled to 0° C. and stirred at this temperature for 30 minutes under nitrogen atmosphere. A solution of 72.4 g (0.2184 mol) tert-butyl 3,3'-azanediylbis(propane-3,1-diyl)dicarbamate (preparation s. example 3) in 200 ml acetone was added into the mixture slowly. The solution was warmed to 20° C. and continued to stir for another 12 hours. Then the reaction mixture was diluted with dichloromethane (300 ml), then the reaction mixture was poured into separatory funnel and washed with water (water 100 ml×5). The organic phase was dried with magnesium sulfate. The organic layer was evaporated to give the crude red solid. The crude product was purified by silica gel chromatography eluted with dichloromethane/methanol (40:1).

Yield: 79.3 g (58%), red solid.

MS: 550 (ESI+, MW-I).

b) Final Step 42 g (120 mmol) of intermediate from example 10, step 1 was dissolved in 250 ml methanol. The reaction mixture was stirred at 20° C. and HCl gas was bubbled through into the reaction system. The reaction mixture was stirred at 20° C. for another 3 hours. Afterwards, the solution was evaporated to dryness. The crude product was purified by reversed phase ($C_{18}$ column) chromatography eluted with water/ethanol (100~10/1) gradient. Yield: 32 g (51%) as red solid.

$^1$H-NMR ($D_2O$): δ=1.95-2.00 (m; 4H, $CH_2$); 2.97-3.02 (m; 4H, $CH_2$); 3.54-3.59 (m; 4H, $CH_2$); 3.87 (s; 6H, $CH_3$); 6.84-6.87 (m; 2H, Aryl-H); 7.27 (s; 2H, Imidazoyl-H); 7.87-7.90 (m, 2H, Aryl-H) ppm.

MS: 330 (ESI+).

Example 11: 2-((4-(bis(4-ammoniobutyl)amino)phenyl)diazenyl)-1,3-dimethyl-1H-imidazol-3-ium dichloride iodide (111)

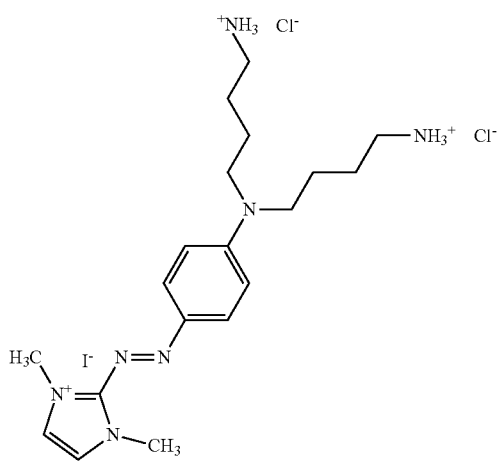

Synthesis Scheme of Example 11
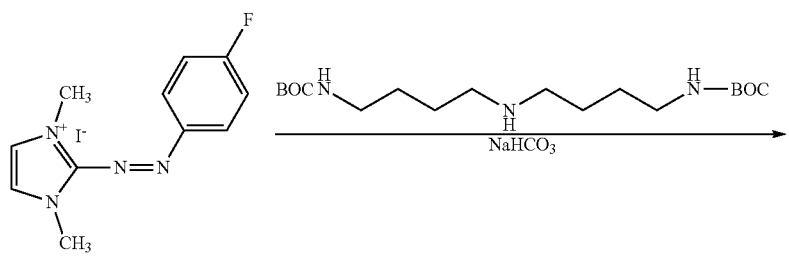
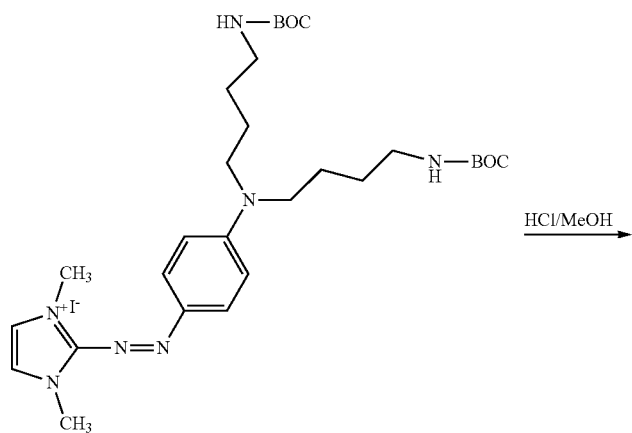
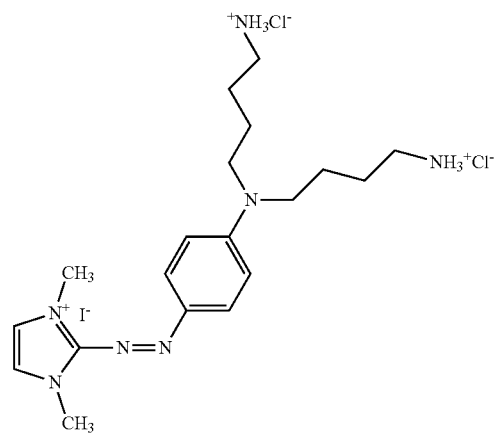

a) Step 1: 2-((4-(bis(2-(tert-butoxycarbonylaminobutyl)amino)phenyl)diazenyl)-1,3-dimethyl-1H-imidazol-3-ium dichloride iodide

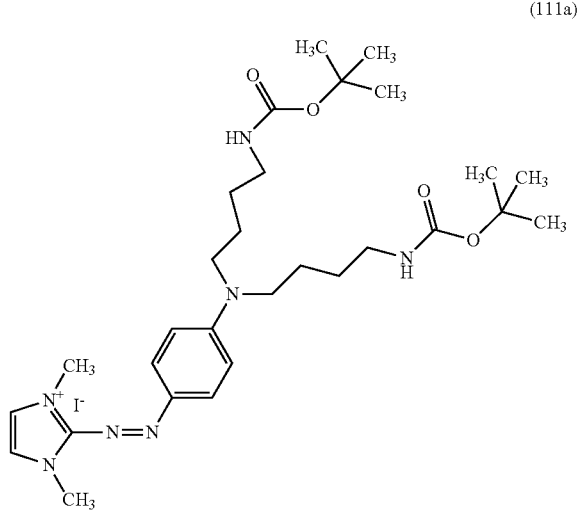 [SMILES: Cn1cc[n+](C)c1N=Nc1ccc(N(CCCCNC(=O)OC(C)(C)C)CCCCNC(=O)OC(C)(C)C)cc1 ; [I-]]

(111a)

84.8 g (245.12 mmol) 2-((4-fluorophenyl)diazenyl)-1,3-dimethyl-1H-imidazol-3-ium iodide and 31 g (367.68 mmol) sodium bicarbonate were suspended in 500 ml of acetone, 125 ml water were added. The reaction mixture was cooled to 0° C. and stirred for 30 minutes at this temperature. A solution of 44 g (122.56 mmol) tert-butyl N-[4-[4-(tert-butoxycarbonylamino)butylamino]butyl]carbamate [preparation: M. Bradley et al., Tetrahedron, 53 (51) 17317 (1997); R. Bergeron, Synthesis 9 (1981) 732; R. Bergeron, Synthesis 8 (1982) 689] in 100 ml acetone was added dropwise. The reaction solution was warmed to 20° C. and continued to stir for another 48 hours. Afterwards, the reaction mixture was diluted with 300 ml dichloromethane (300 ml), poured into a separatory funnel and washed with water. The organic phase was dried with magnesium sulfate and evaporated in vacuum to give the crude material. The crude product was purified by silica gel chromatography eluted with dichloromethane/methanol (50:1). Yield: 42 g (51%), red solid.

b) Step 2 (Final Step)

42 g (61.31 mmol) intermediate from step 1 were dissolved in 150 ml methanol and stirred at 20° C. HCl gas was bubbled through into the reaction system. The reaction mixture was stirred at 20° C. for another 3 hours. The reaction solution was evaporated and the crude product was purified by reverse phase chromatography ($C_{18}$ column) eluted with water/ethanol gradient (100~10/1). Yield: 24.3 g (86%), red solid.

$^1$H NMR ($D_2O$): δ=1.74, 3.03 and 3.60 (each s, br; 10H, $CH_2$), 3.94 (s, 6H, $CH_3$), 6.94, 7.33 and 7.94 (each m, 6H, Aryl-H) ppm.

Example 12: 2-((4-(bis(5-ammoniopentyl)amino)phenyl)diazenyl)-1,3-dimethyl-1H-imidazol-3-ium dichloride iodide

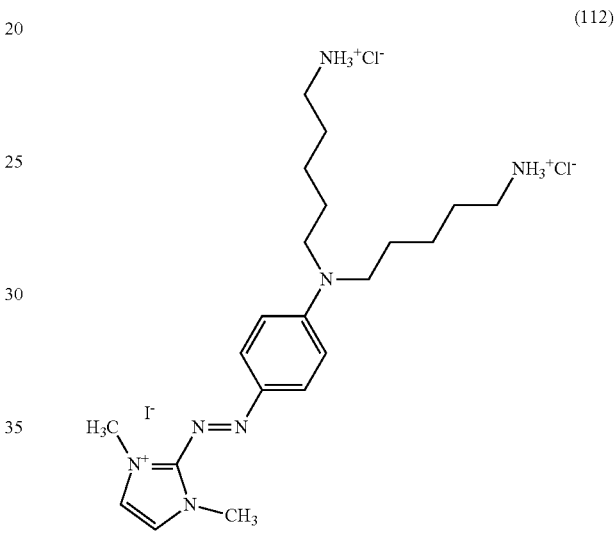

(112)

Synthesis Scheme of Example 12

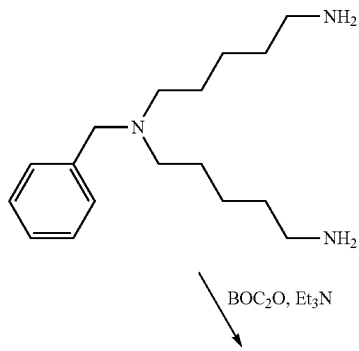

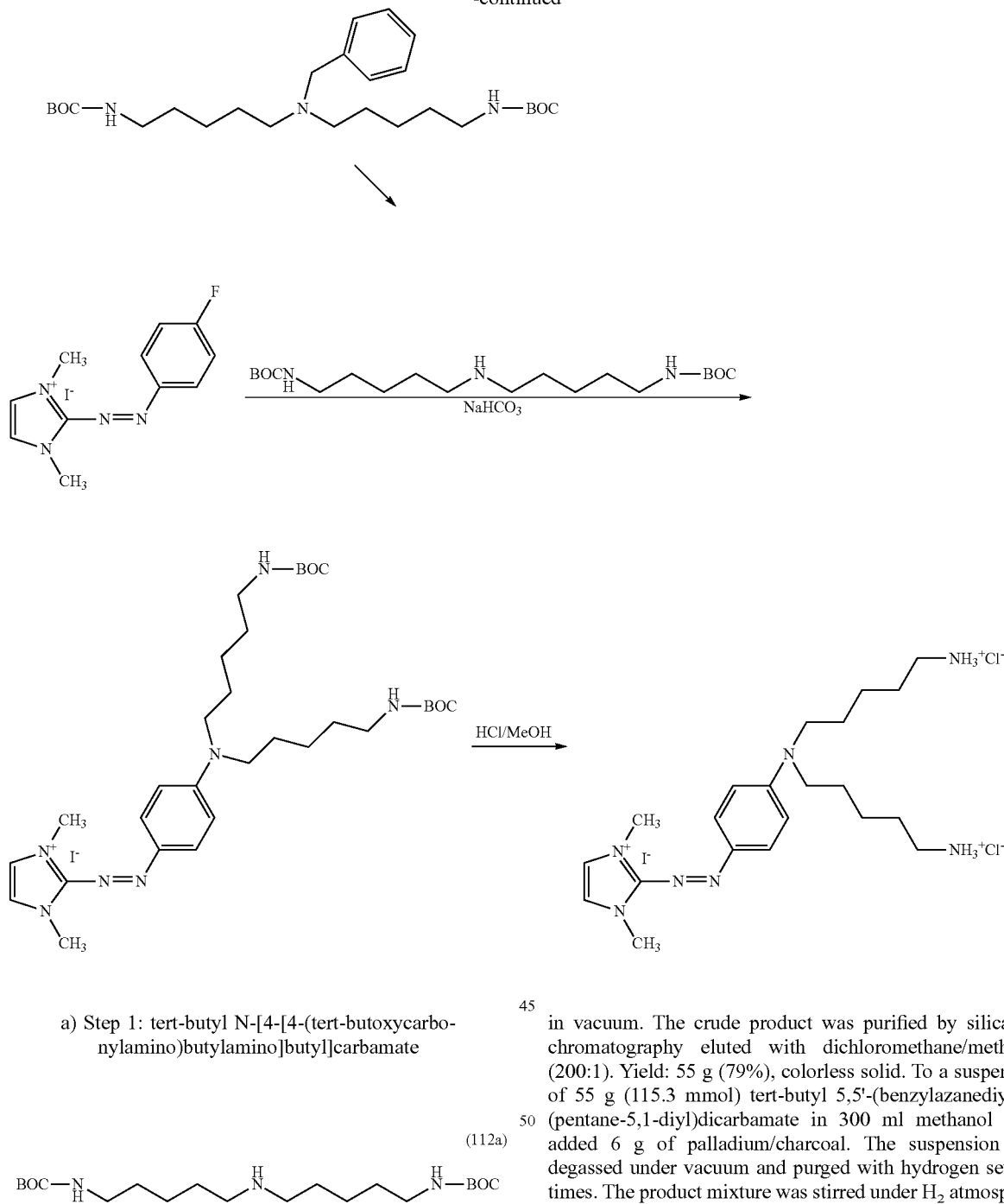

a) Step 1: tert-butyl N-[4-[4-(tert-butoxycarbonylamino)butylamino]butyl]carbamate (112a)

40 g (144.4 mmol) of N1-(5-aminopentyl)-N1-benzylpentane-1,5-diamine prepared according to literature [R. Poulin et al, Bioorg. Med. Chem. Lett. 13 (2003), 3267] and 43.7 g (432.7.4 mmol) N,N-triethylamine were suspended in 400 ml THF. The reaction mixture was cooled to 0° C. A solution of 64 g (293.6 mmol) di-tert-butyl dicarbonate in 100 ml THF was added to the mixture dropwise. Stirring was continued for another 12 hours at 20° C. Afterwards, the product mixture was poured into 1 l of water. The mixture was extracted with ethyl acetate (250 ml, three times). The organic layers were combined and dried with anhydrous magnesium sulfate. The dried organic phase was evaporated in vacuum. The crude product was purified by silica gel chromatography eluted with dichloromethane/methanol (200:1). Yield: 55 g (79%), colorless solid. To a suspension of 55 g (115.3 mmol) tert-butyl 5,5'-(benzylazanediyl)bis(pentane-5,1-diyl)dicarbamate in 300 ml methanol were added 6 g of palladium/charcoal. The suspension was degassed under vacuum and purged with hydrogen several times. The product mixture was stirred under $H_2$ atmosphere at 20° C. for 12 hours. The obtained product suspension was filtered. The filtrate was evaporated to give 39 g crude product as colorless oil. This was treated with 300 ml petrol ether. Under stirring, the reaction mixture was heated to 50° C. for 2 hours until the crude product was completely dissolved. Then, the reaction mixture was cooled to 0° C. for 2 hours. A white precipitate crushed out. The precipitate was collected by filtration, washed with 100 ml petroleum ether and dried in high vacuum at 30° C. for 12 hours.

Yield: 35 g (78%), white solid.

$^1$H-NMR (CDCl$_3$): δ=1.35-1.37 (m; 4H); 1.44 (s; 18H); 1.52-1.57 (m; 4H); 2.48-2.49 (m; 4H); 2.63-2.68 (m; 4H); 4.62-4.63 (m; 2H) ppm; MS m/z: 387 (ESI+).

b) Step 2: tert-butyl N-[5-[N-[5-(tert-butoxycarbonylamino)pentyl]-4-[(E)-(1,3-dimethylimidazol-1-ium-2-yl)azo]anilino]pentyl]carbamate iodide

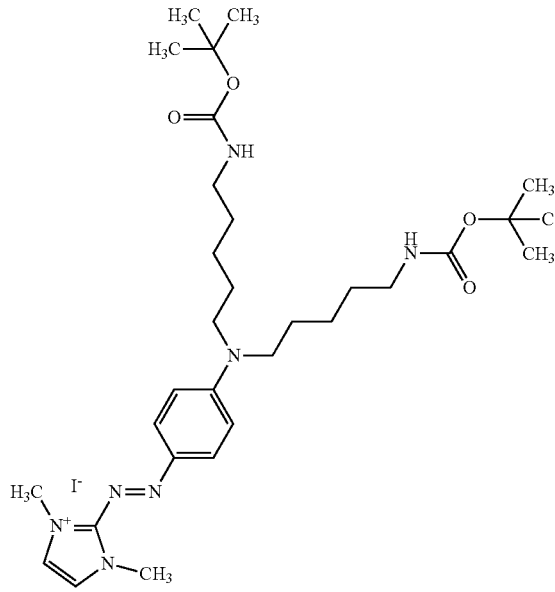
(112c)

60 g (174.0 mmol) 2-((4-fluorophenyl)diazenyl)-1,3-dimethyl-1H-imidazol-3-ium iodide and 22 g (264.5 mmol) sodium bicarbonate were suspended in a mixture of 400 ml acetone and 100 ml water. The reaction mixture was stirred at 0° C. for 30 min under N2 atmosphere. A solution of 35 g (88.2 mmol) tert-butyl N-[4-[4-(tert-butoxycarbonylamino)butylamino]butyl]carbamate from step 1 in 100 ml acetone was added into the mixture slowly. The solution was warmed to 20° C. and continued to stir for another 48 hours. The reaction mixture was diluted with 300 ml dichloromethane and poured into a separatory funnel. The organic layers were washed with water thoroughly. The organic phase was dried and evaporated in vacuum to give the crude red solid. The crude product was purified by silica gel chromatography eluted with dichloromethane/methanol (50:1).

Yield: 39 g (60%), red solid.

$^1$H-NMR (CDCl3): δ 1.45 (s, 18H, CH$_2$); 1.51-1.59 (m, 5H, CH$_2$); 1.73 (s, 7H, CH$_2$); 3.12-3.16 (m, 4H, CH$_2$); 3.46-3.50 (m, 4H, CH$_2$); 4.13 (s, 6H, CH$_3$); 4.65-4.67 (m, 2H) ppm. MS: 586 (ESI+).

c) Step 3: Final Step 50 g (70.1 mmol) tert-butyl N-[5-[N-[5-(tert-butoxycarbonylamino)pentyl]-4-[(E)-(1,3-dimethylimidazole-1-ium-2-yl)azo]anilino]pentyl]carbamate iodide from step 2 was dissolved in 250 ml methanol and stirred at 20° C. Then, HCl gas was bubbled through into the reaction system. The reaction mixture was stirred for another 3 hrs. The obtained solution was evaporated in vacuum. The crude product was purified by reverse phase chromatography (C18 column) eluted with water/ethanol gradient (100~10/1).

Yield: 21 g (51%), red solid.

$^1$H NMR (D$_2$O): δ=1.43 (m, br; 4H, CH$_2$), 1.68 (m, br; 8H, CH$_2$), 3.00 (m, br; 4H, CH$_2$), 3.42 (m, br; 4H, CH$_2$), 3.78 (s; 6H, CH$_3$), 6.70, 7.19 and 7.62 (each m; 6H, Aryl-H) ppm.

Example 13: N1-[4-[(E)-(1-methylpyridine-1-ium-2-yl)azo]phenyl]benzene-1,4-diamine chloride

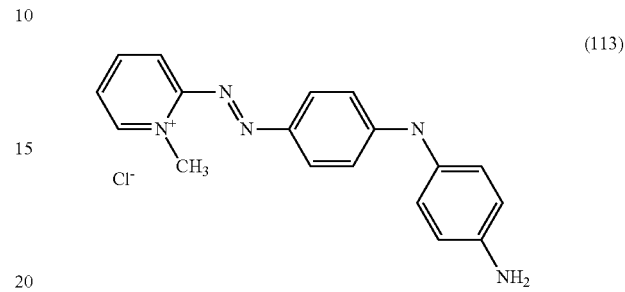
(113)

Synthesis Scheme Example 13

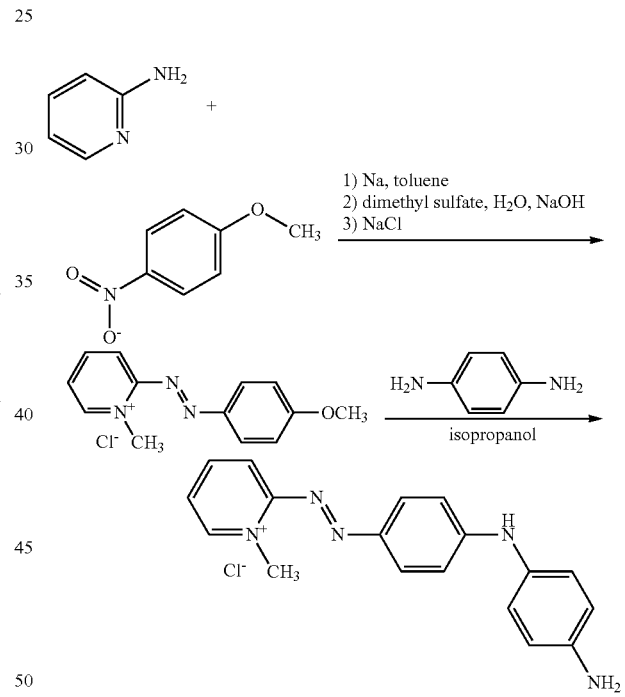

a) Step 1: (E)-(4-methoxyphenyl)-(1-methylpyridin-1-ium-2-yl)diazene chloride

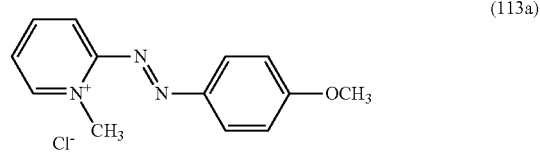 [SMILES: COc1ccc(/N=N/c2cccc[n+]2C)cc1 ; [Cl-]]
(113a)

A mixture of 23.5 g (0.25 mol) 2-aminopyridine and 42.1 (0.275 mol) 4-nitroanisole in 500 ml toluene were reacted with 12.7 g sodium according to literature [E. Taylor, C. P. Tseng, J. B. Rampal, J. Org. Chem. 47 (1982) 552; K. Rück-Braun, S. Dietrich, S. Kempa, B. Priewisch, Science of Synthesis, 31 b (2007)1425]. Yield: 21 g (39%). 20 g (around 0.093 mol) of crude (E)-(4-methoxyphenyl)-(2-pyridyl)diazene was dissolved in 160 ml water. 61.2 g (46 ml, 0.485 mol) dimethylsulfate were added dropwise within 1 hour. Simultaneously, pH 9 was adjusted by the addition of aqueous sodium hydroxide (10%) solution. During the addition, temperature of the reaction mixture must be kept below 30° C. The product mixture was stirred at 20° C. for 12 hours, again a pH of 9 was adjusted with sodium hydroxide solution.

To that production suspension, 50 g of solid sodium chloride and 30 g of potassium chloride were added. Afterwards, the reaction mixture was carefully evaporated in vacuum while the temperature was kept below 60° C. The residue was treated with 400 ml ethanol and stirred for 1 hour. The solution was filtrated and the ethanolic solution evaporated to 1/10 of the volume. The product was precipitated with 100 ml of diethyl ether. The precipitate was filtered-off and dried at 40° C. in vacuum. Yield: 9.6 g (39%), brownish solid.

b) Step 2 (Final Step)

A solution of 1.25 g (5 mmol) (E)-(4-methoxyphenyl)-(1-methylpyridine-1-ium-2-yl)diazene was suspended in 25 ml 2-propanol. 0.75 g (7 mmol) p-phenylenediamine was added dropwise within 10 minutes. The obtained dark suspension was diluted with 8 ml methanol and stirred at 20° C. for 12 hours. Then, the product suspension was heated to 40° C. and stirred for another 3 hours. The dark-blue suspension was cooled to 10° C. The formed precipitate was collected by filtration, washed with 200 ml of 2-propanol and dried at 30° C. for 12 hours.

Yield: 1.44 g (86%), blue solid.

$^1$H NMR (D$_2$O): δ=4.20 (s; 6H, CH$_3$), 6.6-7.0 (m; 6H, Aryl-H), 7.51 (m; 1H, Aryl-H), 7.71 (m; 2H, Aryl-H), 7.80, 8.18 and 8.37 (m; each 1H, Aryl-H) ppm.

Example 14: 3-[2-[(E)-[4-(4-aminoanilino)phenyl]azo]pyridine-1-ium-1-yl]propylammonium dibromide

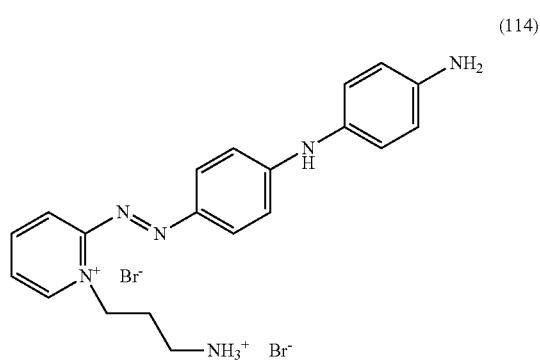 [SMILES: Nc1ccc(Nc2ccc(/N=N/c3cccc[n+]3CCC[NH3+])cc2)cc1 ; [Br-] ; [Br-]]
(114)

Synthesis Scheme for Example 14

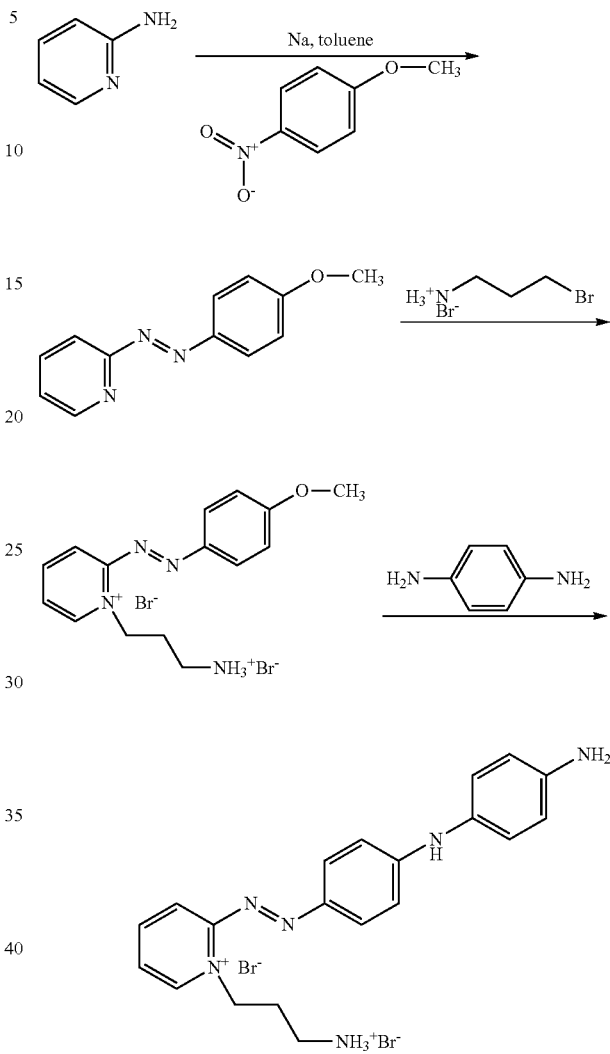

a) Step 1: 2-[p-Methoxyphenyl)azo]pyridine

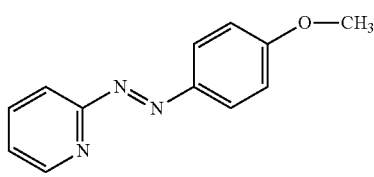
(114a)

2-[p-Methoxyphenyl)azo]pyridine has been prepared by condensation of 5.5 g (0.059 mol) pyridine-2-amine with 9.94 g (0.065 mol) 4-nitroanisole using sodium according to literature [E. Taylor, C. P. Tseng, J. B. Rampal, J. Org. Chem. 47 (1982) 552; K. Ruček-Braun, S. Dietrich, S. Kempa, B. Priewisch, Science of Synthesis, 31b (2007)1425].

Yield: 5.2 g (41%) dark oil.

b) Step 2: 3-[2-[(E)-[4-(4-aminoanilino)phenyl]azo]pyridin-1-ium-1-yl]propylammonium dibromide

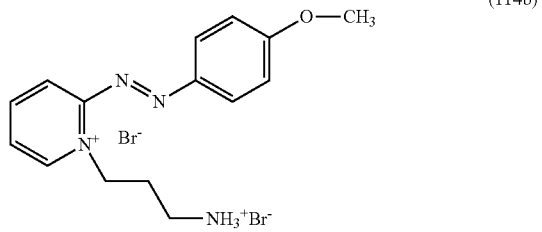
(114b)

The reaction was performed under nitrogen. 1.2 g (0.006 mol) 2-[p-Methoxyphenyl)azo]pyridine were dissolved in 60 ml of acetonitrile. To the dark orange solution, 2.99 g (0.014 mol) 3-bromopropylamine hydrobromide were added. The reaction mixture was heated to 80° C. and kept at that temperature for 48 hours. During the heating period, a brown sticky precipitate was formed. The reaction mixture was cooled to 20° C. and the supernatant liquid was decanted. The solid residue was dissolved in methanol and the organic solution is evaporated.

Yield: 2.0 g (81%), red solid.

$^1$H NMR (CD$_3$OD): δ=2.49, 3.20 and 5.25 (m; each 2H, CH$_2$), 4.04 (s; 3H, OCH$_3$), 7.27 (m; 2H, Aryl-H), 8.16 (m; 1H, Aryl-H), 8.29 (m; 2H, Aryl-H), 8.37, 8.72 and 9.21 (m; each 1H, Aryl-H) ppm.

c) Step 3: Final Step

The reaction is performed under nitrogen. 2.5 g (0.006 mol) 3-[2-[(E)-(4-methoxyphenyl)azo]pyridine-1-ium-1-yl]propylammonium dibromide were dissolved in 50 ml of methanol and stirred 20° C. Then, 0.8 g (0.007 mol) p-phenylendiamine was added. The reaction mixture has been stirred for 3 hours at 20° C. Afterwards, a mixture of 300 ml of isopropanol and 600 ml of ethyl acetate were poured into the reaction mixture. Within 30 minutes, the product precitated. The residue was filtered off, dissolved in methanol and evaporated to dryness.

Yield: 0.4 g (13%), dark-violet solid.

$^1$H NMR (CD$_3$OD): δ=2.42, 3.18 and 5.03 (m; each 2H, CH$_2$), 6.81, 6.92, 7.12, 7.72, 8.05, 8.23, 8.38, 8.81 (m; totally 12H, Aryl-H) ppm.

UV: λ$_{max}$=569 nm.

Example 15: 2-((4-(bis(3-ammoniopropyl)amino)phenyl)diazenyl)-3-methyl 1,3-thiazole-3-ium trichloride

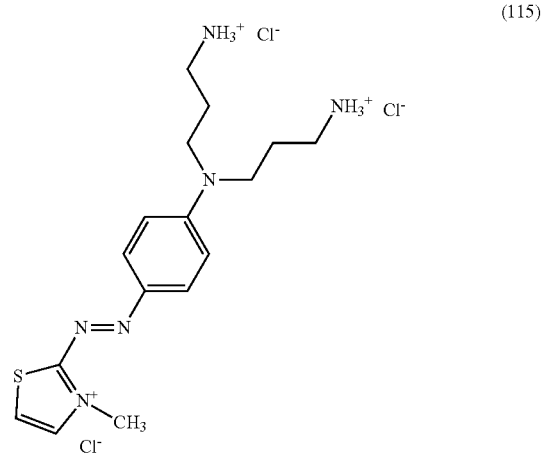 [SMILES: C[n+]1ccsc1/N=N/c1ccc(N(CCC[NH3+])CCC[NH3+])cc1 ; [Cl-] ; [Cl-] ; [Cl-]]
(115)

Synthesis Scheme of Example 15

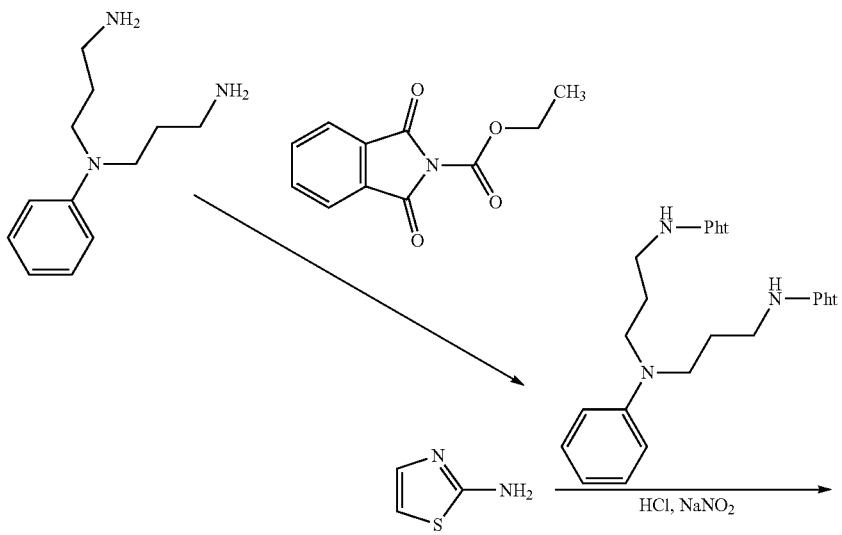

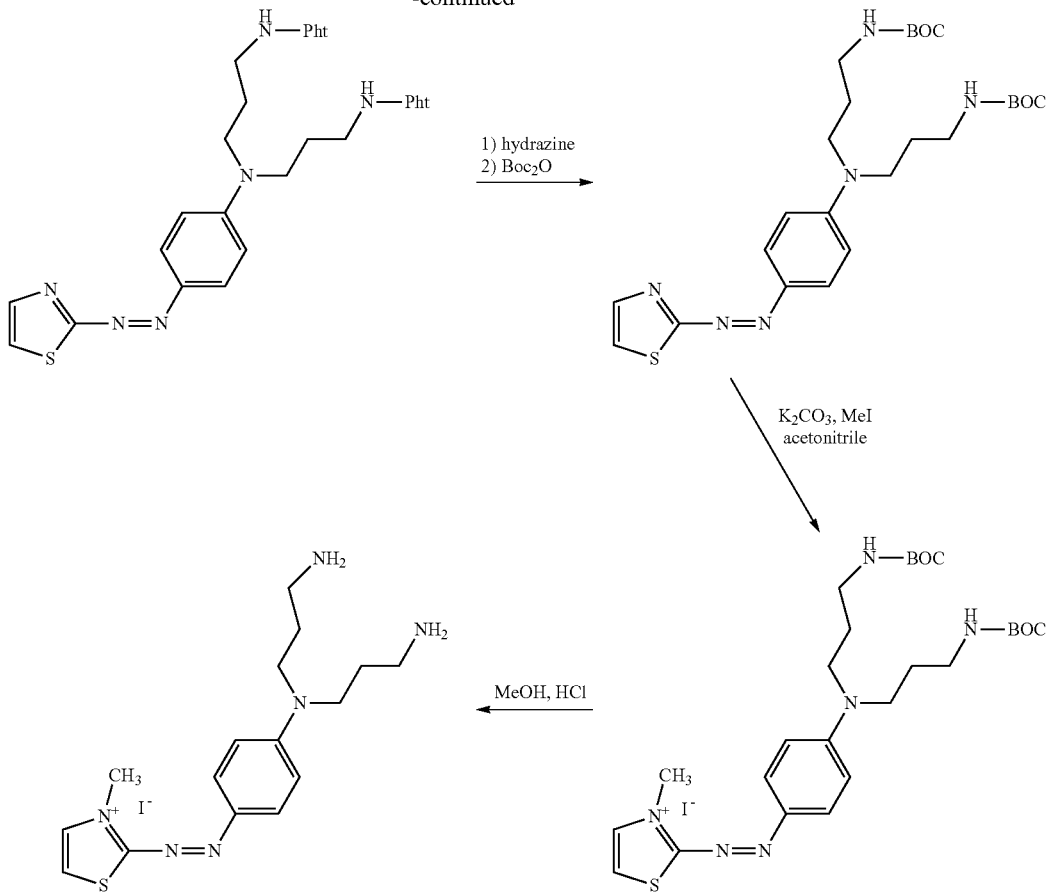

a) Step 1: 2,2'-(((4-(1,3-thiazol-2-yldiazenyl)phenyl)imino)di-3,1-propanediyl-bis(1H-isoindol-1,3(2H)-dione I) 2,2'-(iminodi-3,1-propanediyl)bis(1H-isoindol-1,3(2H)-dione

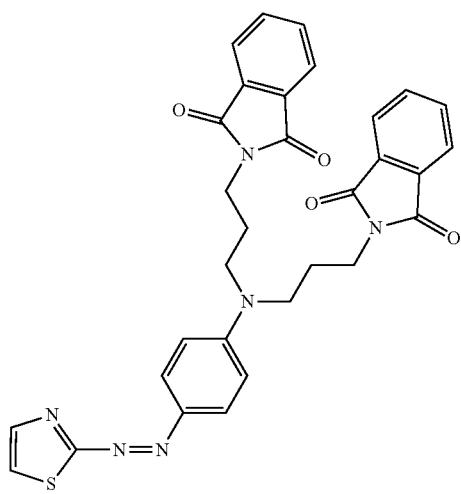
(115a)

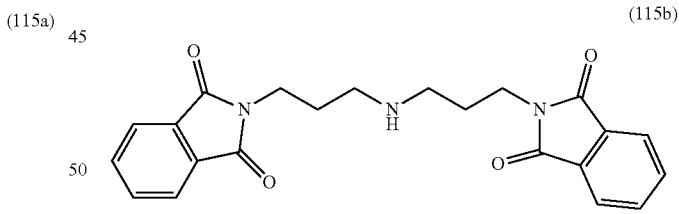
(115b)

5 g (0.024 mol) N,N-bis(3-aminopropyl)aniline prepared according to literature [Arbusov et al. Doklady Ademii Nauk SSR, 91 (1953) 269] and 16 g (0.073 mol) ethyl 1,3-dioxoisoindolin-2-carboxylate were suspended in 100 ml chloroform and stirred at 20° C. Afterwards, the reaction mixture was heated to 70° C. and kept at this temperature for 12 hours. The solution was concentrated to dryness to give crude product as brown oil which was purified by recrystallization using methanol. Yield: 10.6 g (89%), white solid.

Yield: 10.6 g (89%), white solid.

II)

Diazotization/Coupling: A mixture of 12.5 g (0.125 mol) thiazol-2-amine, 20 ml acetic acid (20 ml), 40 ml concentrated hydrochloric acid and 40 ml water was stirred at 20° C. The reaction mixture was cooled to 0° C. and stirred at this temperature for 30 min under nitrogen atmosphere. 9.3 g (0.134 mol) sodium nitrite solution in 40 ml water was added into the mixture slowly while keeping the inner temperature below 5° C. The solution was continued to stir at −5-0° C. for another 30 minutes. Then, a solution of 45 g (0.096 mol) 2-formyl-N-[3-[3-[(2-formylbenzoyl)amino]propylamino]propyl]benzamide from I) in 100 ml THF was added slowly while keeping the inner temperature between 0 and 5° C. The solution was stirred at 0° C. for another 30 minutes. The reaction mixture was warmed to 20° C., diluted with water (1000 ml) and neutralized with 2M sodium hydroxide solution. The reaction mixture was poured into a separatory funnel and extracted with 500 ml dichloromethane. The organic phase were combined, dried with magnesium sulfate and evaporated to dryness. The crude product was purified by silica gel chromatography eluted with dichloromethane/ethyl acetate (20:1). Yield: 36 g (65%), red solid.

b) Step 2: tert-butyl N-[3-[N-[3-(tert-butoxycarbonylamino)propyl]-4-[(E)-thiazol-2-ylazo]anilino]propyl]carbamate

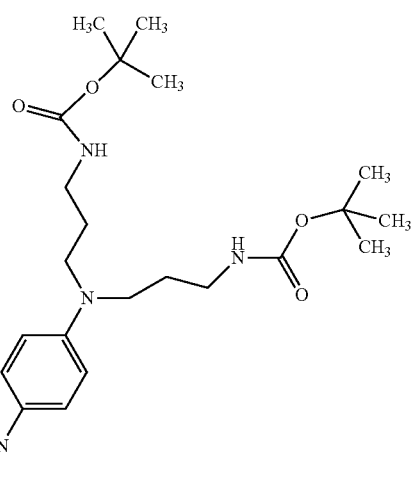

(115c)

A mixture of 30 g (0.052 mol) intermediate 15 a) was stirred in 600 ml of a mixture of dichloromethane/methanol (1:1). Then 30.5 g (0.52 mol) hydrazine hydrate was added dropwise under argon. After addition, the reaction mixture was stirred at 20° C. for another 12 hours. The reaction mixture was filtered and the filtrate was concentrated to give crude product. This crude product was dissolved in 300 ml of a mixture of dichloromethane/methanol (1:1) and stirred at 20° C. A solution of 283.4 g (1.3 mol) ditert-butyl dicarbonate in 300 ml dichloromethane was added dropwise under argon. After addition, the reaction mixture was stirred at 20° C. for another 12 hours. Then, the solution was evaporated to dryness. The crude product was purified by silica gel chromatography eluted with dichloromethane/methanol (40:1). Yield: 11.6 g (42%), red solid.

c) Step 3: tert-butyl N-[3-[N-[3-(tert-butoxycarbonylamino)propyl]-4-[(E)-(3-methylthiazole-3-ium-2-yl)azo]anilino]propyl]carbamate chloride

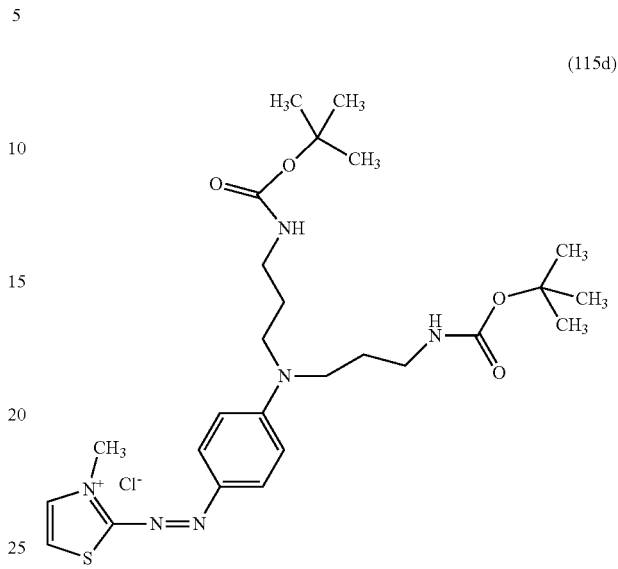

(115d)

A reaction mixture of 18 g (34.75 mmol) intermediate from step 2 and 18 g (130 mmol) potassium carbonate in 180 ml acetonitrile was stirred at 20° C. 49.3 g (347 mmol) methyliodide was added dropwise. The reaction mixture was heated to 50° C. and kept for 12 hours at this temperature under nitrogen atmosphere. The reaction mixture was filtered and the filtrate evaporated to dryness. The crude product was purified by silica gel chromatography eluted with dichloromethane/methanol (50:1). Yield: 13.8 g (75%), blue solid.

d) Step 4 (Final Step)

19 g (35.6 mmol) intermediate from step 3 was dissolved in 100 ml methanol and stirred at 20° C. Then, HCl gas was bubbled through into the reaction system. The reaction mixture was stirred at 20° C. for another 3 hours. The solution was evaporated to dryness in vacuum. The obtained crude product was purified by reversed phase chromatography ($C_{18}$ column) eluted with water/ethanol gradient (100~10/1).

Yield: 11.7 g (81%), blue solid.

$^1$H NMR ($D_2O$): δ=2.09 (s, br; 4H, $CH_2$), 3.15 (s, br; 4H, $CH_2$), 3.68 (m; 4H, $CH_2$), 3.88 (s; 3H, $CH_3$), 6.83 (s, br; Aryl-H), 7.42 (d; 2H, Aryl-H), 7.65 (s, br; 2H, Aryl-H) ppm.

Example 16: 1-(3-aminopropyl)-4-((E)-(4-(dimethylamino)phenyl)diazenyl)pyridinium bromide

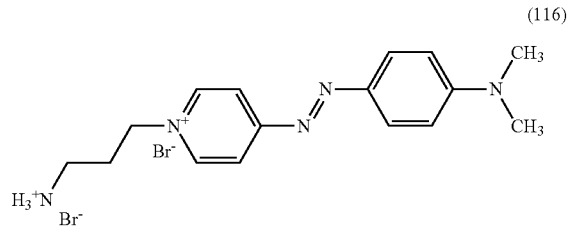

(116)

Scheme Example 16

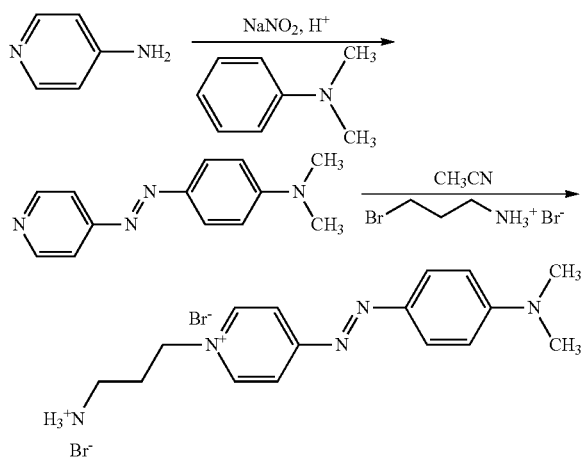

a) Step 1: N,N-Dimethyl-4-[(E)-pyridin-1-ium-4-ylazo]aniline bromide (116a)

This compound has been prepared according to a slightly modified literature procedure [S. Yitzchaik et al., J. Am. Chem. Soc. 2008, 130 (12) 4158].

a) Diazotization: To a stirred mixture of 20 ml phosphoric acid (65%) and 10 ml nitric acid at 20° C., 4.0 g (0.043 mol) 4-amino-pyridine were added. The formed colorless solution was cooled down to a temperature range of 0-5° C. Within 30 minutes, 3.0 g (0.043 mol) of solid sodium nitrite were added portionwise. The reaction mixture was stirred for 20 minutes at 0-5° C., then 50 g of ice were given into the solution.

b) Coupling: 3.2 g (0.026 mol) N,N-dimethylaniline were dissolved in 40 ml of phosphoric acid (65%). The formed yellowish solution was cooled down to a temperature range of 0-5° C. To that solution, the fresh diazo solution prepared in a) was added dropwise within 5 minutes. The formed orange reaction mixture was stirred for 4 hours at 0-5° C. Then no diazo could be detected (test with H-acid). The reaction mixture was warmed-up to 20° C. and further stirred for twelve hours.

Work-up: The orange suspension was adjusted to pH 8.2 with 91.7 ml of 30% sodium hydroxide solution. The precipitate was filtered off and washed with 1000 ml of water. It was suspended in 1000 ml of water, stirred for 30 minutes and filtered off again. The moist residue was dissolved in 200 ml of methanol, heated to 60° C. and evaporated until recrystallization started. Then the reaction mixture is cooled down to 0° C., stirred at that temperature for 1 hour. The formed precipitate is filtered off and dried in high vacuum at 40° C.

Yield: 1.63 g (27%) orange powder. $\lambda_{max}$=540 nm.

b) Final Step 0.5 g (0.0022 mol) N,N-Dimethyl-4-[(E)-pyridin-1-ium-4-ylazo]aniline bromide prepared in example 11a) was dissolved in 20 ml of acetonitrile. To that reddish orange solution, 0.6 g (0.0026 mol) of 3-bromopropylamine hydrobromide was added. The reaction mixture was heated to 80° C. and kept at that temperature for 12 hours. Another 0.6 g (0.0026 mol) of bromopropylamine hydrobromide were added. The reaction mixture was stirred for another 12 hours. The formed red-violet precipitate was filtered off, washed with little cold acetonitrile and 100 ml of ethyl acetate and dried in high vacuum at 30° C. Yield: 910 mg dark green powder, contains unreacted 3-brompropylamine hydrobromide.

$^1$H NMR (D$_2$O): δ=2.3 (m; 4H, CH$_2$), 3.12 (m; 4H, CH$_2$), 3.24 (s; 6H, CH$_3$), 4.53 (m; 4H, CH$_2$), 6.96 (m; 2H, Aryl-H), 7.9-8.0 (m; 4H, Aryl-H), 8.59 (m; 2H, Aryl-H) ppm.

UV $\lambda_{max}$=572 nm, MS (ESI): m/z=284 (C$_{16}$H$_{22}$N$_5$Br)$^+$.

Example 17: 1-(4-aminobutyl)-4-((E)-(methyl(phenyl)hydrazono)methyl)pyridinium bromide

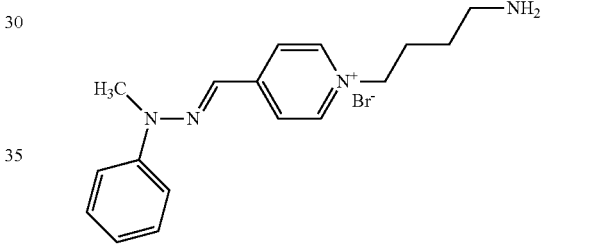

(117)

Synthesis Scheme Example 17

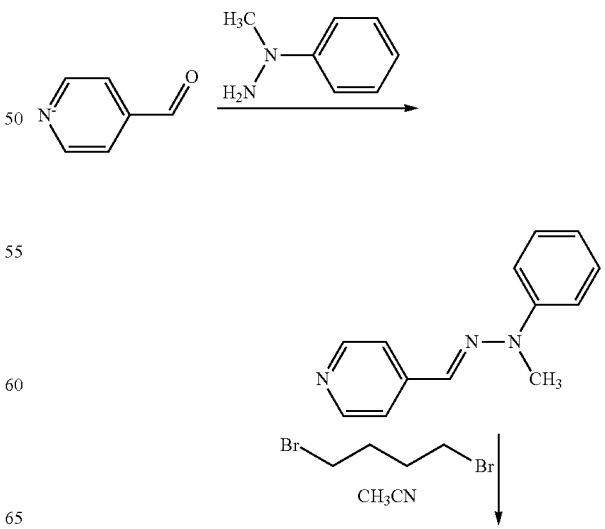

-continued

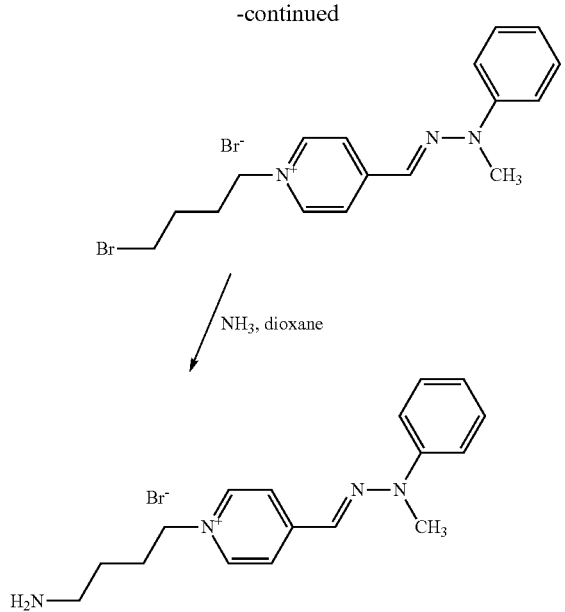

a) Step 1: N-methyl-N-[(E)-4-pyridylmethyl-eneamino]aniline

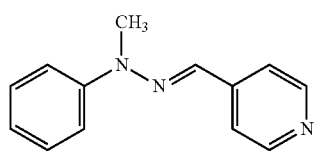

25.5 g (238 mmol) N-methyl-phenylhydrazine and 24.8 g (202 mmol) 4-pyridinealdehyde were reacted according to the procedure given in WO2007025889. Yield: 36.4 g (85%).

b) Step 2: 1-(4-brombutyl)-4-((E)-(methyl(phenyl) hydrazono)methyl)pyridinium bromide

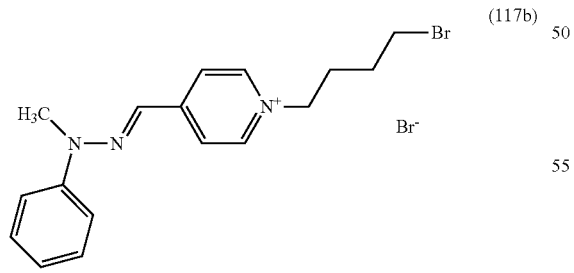

2.11 g (0.010 mol) of N-methyl-N-[(E)-4-pyridylmethyl-eneamino]aniline prepared in step 1 and 10.8 g (0.05 mol) 1,4-dibrombutane were suspended in 50 ml of acetonitrile and stirred for 15 minutes at 20° C. The reaction mixture was heated to 85° C. and kept at this temperature for 12 hours. Afterwards, the reaction mixture was evaporated in vacuum to dryness. The sticky orange residue was suspended in 100 ml of acetone, heated to 50° C. for some minutes and cooled down to 20° C. The solution was evaporated to ¼ of the original volume followed by the addition of 50 ml 2-propanol. A precipitate was formed which was filtered off and dried in high vacuum at 40° C.

Yield: 2.4 g (56%), orange sticky solid.

c) Final Step 2.1 g (0.010 mol) of 1-(4-brombutyl)-4-((E)(methyl(phenyl)hydrazono)methyl)pyridinium bromide were suspended in a mixture of 60 ml water/dioxane (1:1) and stirred for 15 minutes at 20° C. To that yellow solution, 10 ml of 30% aqueous ammonia solution was added. The reaction mixture was heated up to 75° C. and kept at that temperature for three hours. Afterwards, the yellow solution was evaporated in vacuum to of the original volume, at the same time the product crushed out.

Yield: 2.2 g (62%), dark orange solid.

$^1$H NMR (DMSO-$d_6$): δ=1.58, 1.98, 2.87, 4.52 (m; each 2H, CH$_2$), 3.61 (s; 6H, CH$_3$), 7.12, 7.43, 7.60, 7.85 8.21, 8.90 (each m; 10H, Aryl-H and CH=N) ppm.

Example 18: N1-[4-[(E)-(1,3-dimethylimidazol-1-ium-2-yl)azo]phenyl]propane-1,2-diamine chloride

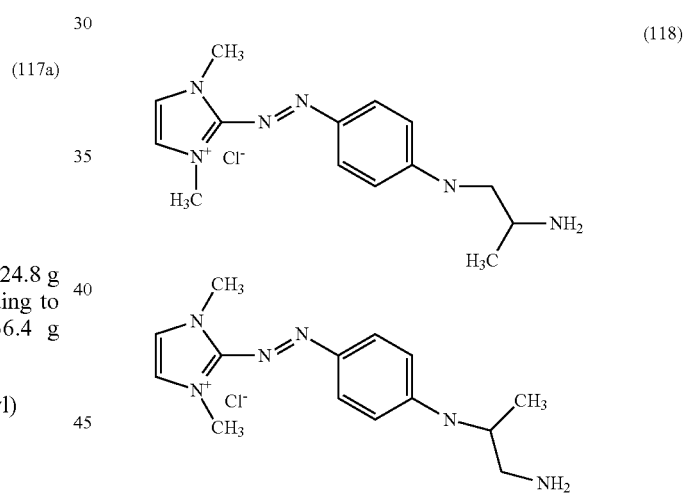

isomeric mixture

Synthesis Scheme of Example 18

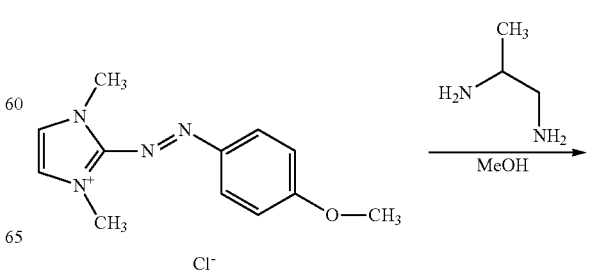

-continued

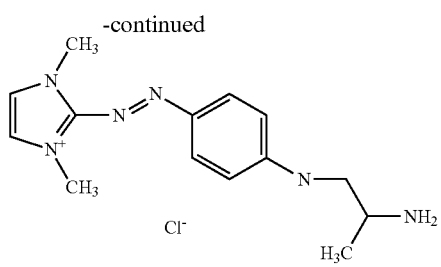

6.7 g (7.8 ml, 90 mmol) of 1,2-diminopropane were suspended in 30 ml methanol. The stirred solution was heated to 60-65° C. At this temperature, a solution of 8.0 g (30 mmol) (E)-(1,3-dimethylimidazol-1-ium-2-yl)-(4-methoxyphenyl)diazene chloride prepared according to literature [WO2012150549, WO200909121] in 30 ml methanol was added dropwise within four hours. The product suspension were kept at 60-65° C. for 12 hours and then cooled to 20° C. The reaction mixture was evaporated in vacuum. The residue was dissolved in 100 ml of distilled water and 10 ml of potassium chloride solution (3M) were added. The solution was filtrated and evaporated to dryness in vacuum. The raw product was treated with 100 ml of methanol and the solution stored at 0° C. for 12 hours. Then, the formed precipitate was collected by filtration. Yield: 2.2 g (24%), red solid. The product was obtained as isomeric mixture.

Example 19: N'-[4-[(E)-(1,3-dimethylimidazole-1-ium-2-yl)azo]phenyl]butane-1,4-diamine chloride (119)

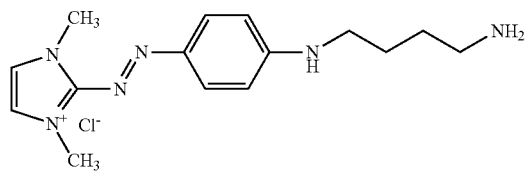

Synthesis Scheme of Example 19

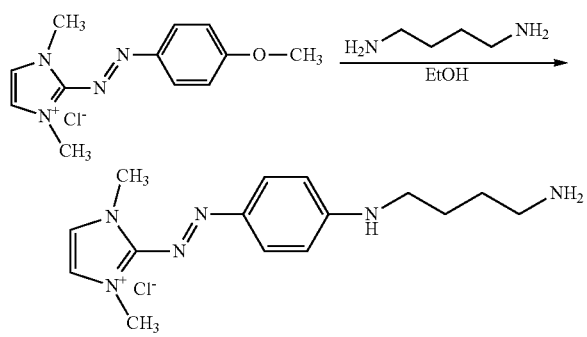

40.0 g (0.15 mol) of 2((4-methoxyphenyl)diazenyl)-1,3-dimethyl-1H-imidazol-3-ium chloride [preparation s. WO2009090125] were dissolved in 50 ml ethanol. Under stirring at 20° C., 75 g (0.85 mol) 1,4-diaminobutane were added. The reaction solution was heated to 45° C. and kept at this temperature for 2 hours. The product mixture was diluted with 50 ml of ethanol and filtrated. The mother liquor was evaporated to of original volume. To that solution, 500 ml of methyl tert.butylether were added. The precipitate was collected by filtration and dried in high vacuum at 60° C. Yield: 38.7 g (80%), red solid.

Example 20: 1-amino-3-[4-[(E)-(1,3-dimethylimidazol-1-ium-2-yl)azo]anilino]propan-2-ol chloride (120)

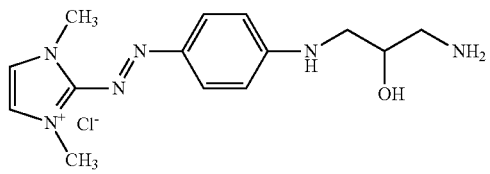

Synthesis Scheme of Example 20

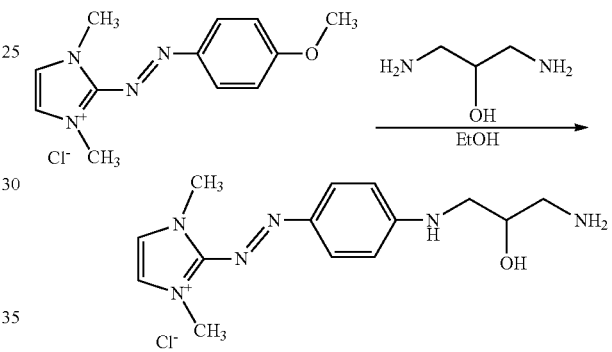

Under stirring, 34.6 g (0.1298 mol) 2((4-methoxyphenyl)diazenyl)-1,3-dimethyl-1H-imidazol-3-ium chloride were suspended in 80 g ethanol. The mixture was heated to reflux and filtrated hot. The mother liquor was cooled to 20° C. Under stirring, 28.41 g (0.2995 mol) 1,3-diamino-2-propanol was added. The mixture was heated to 55° C. for 10 hours. The formed precipitate was removed by filtration. The mother liquor was evaporated in vacuum until dryness. The raw product was treated with 150 ml methanol and heated to reflux. To that hot mixture, 300 g isopropanol was added. The formed precipitate was collected by filtration.

Yield: 15.1 g (38%), red solid.

Example 21: N'-[2-[4-[(E)-(1,3-dimethylimidazol-1-ium-2-yl)azo]anilino]ethyl]ethane-1,2-diamine chloride (121)

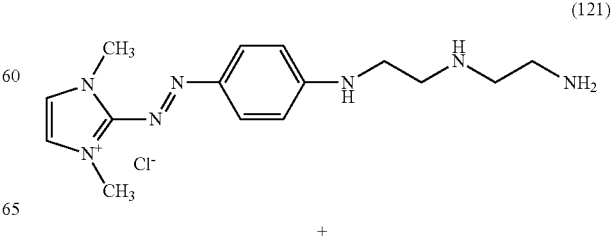

+

-continued

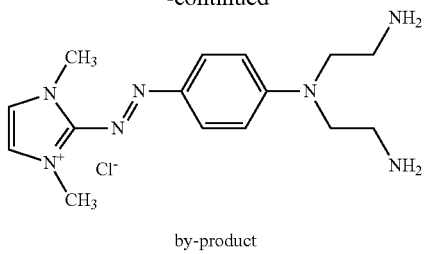

by-product

Synthesis Scheme of Example 21

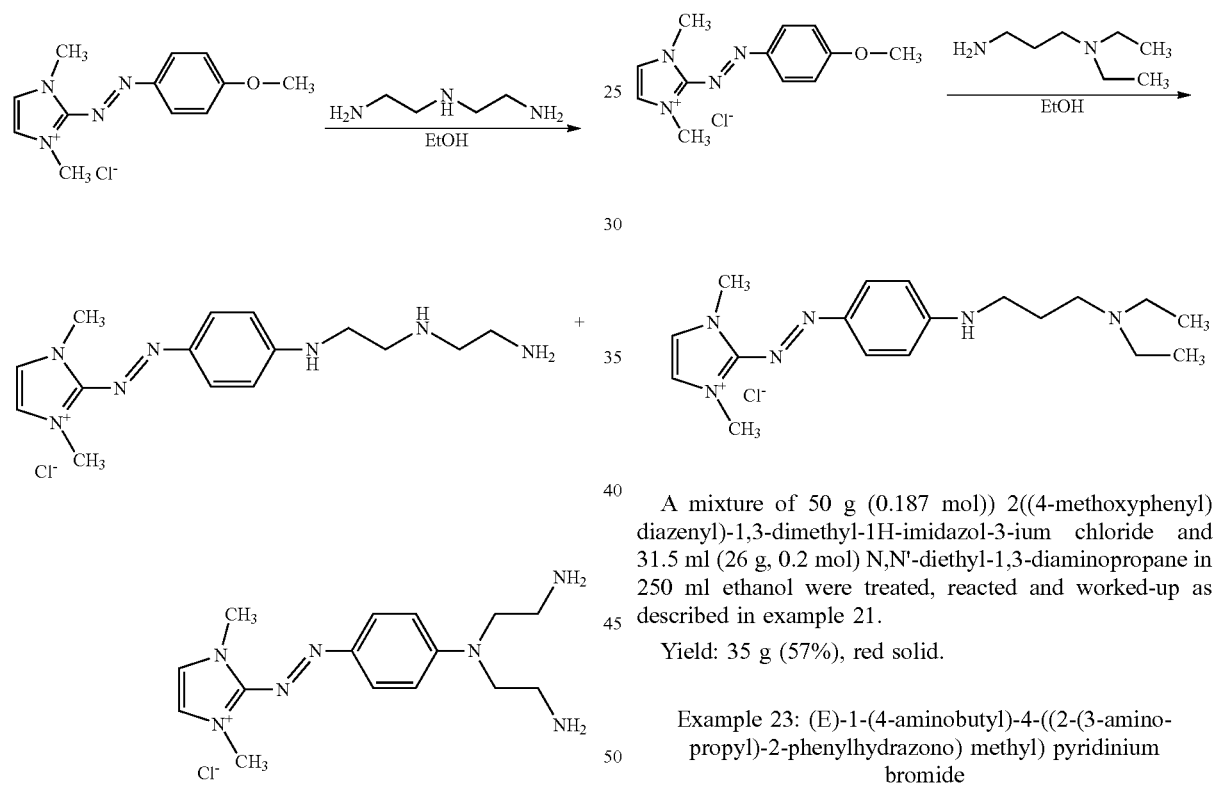

66.5 g (0.25 mol) 2((4-methoxyphenyl)diazenyl)-1,3-dimethyl-1H-imidazol-3-ium chloride were suspended in 300 ml ethanol. The mixture was heated to reflux and filtrated hot. The mother liquor was stirred at 55° C. At this temperature 26.03 g (0.25 mol) diethylenetriamine were added in portions within one hour. The product mixture was kept at 55° C. for 10 hours. The formed precipitate was removed by filtration. The mother liquor was evaporated in vacuum to dryness. The raw product was recrystallized in 400 ml of isopropanol. Yield: 9 g (11%), red solid. The product is a mixture of two isomers.

Example 22: N-[4-[(E)-(1,3-dimethylimidazol-1-ium-2-yl)azo]phenyl]-N',N'-diethylpropane-1,3-diamine chloride (122)

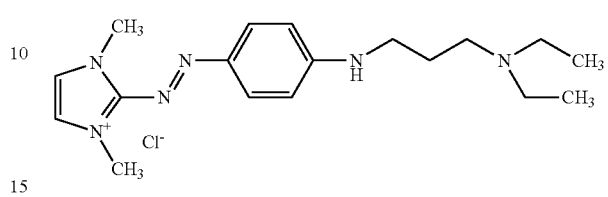

Synthesis Scheme of Example 22

A mixture of 50 g (0.187 mol)) 2((4-methoxyphenyl)diazenyl)-1,3-dimethyl-1H-imidazol-3-ium chloride and 31.5 ml (26 g, 0.2 mol) N,N'-diethyl-1,3-diaminopropane in 250 ml ethanol were treated, reacted and worked-up as described in example 21.

Yield: 35 g (57%), red solid.

Example 23: (E)-1-(4-aminobutyl)-4-((2-(3-aminopropyl)-2-phenylhydrazono) methyl) pyridinium bromide (123)

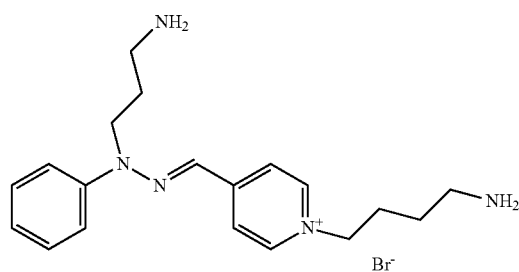

Synthesis Scheme of Example 23
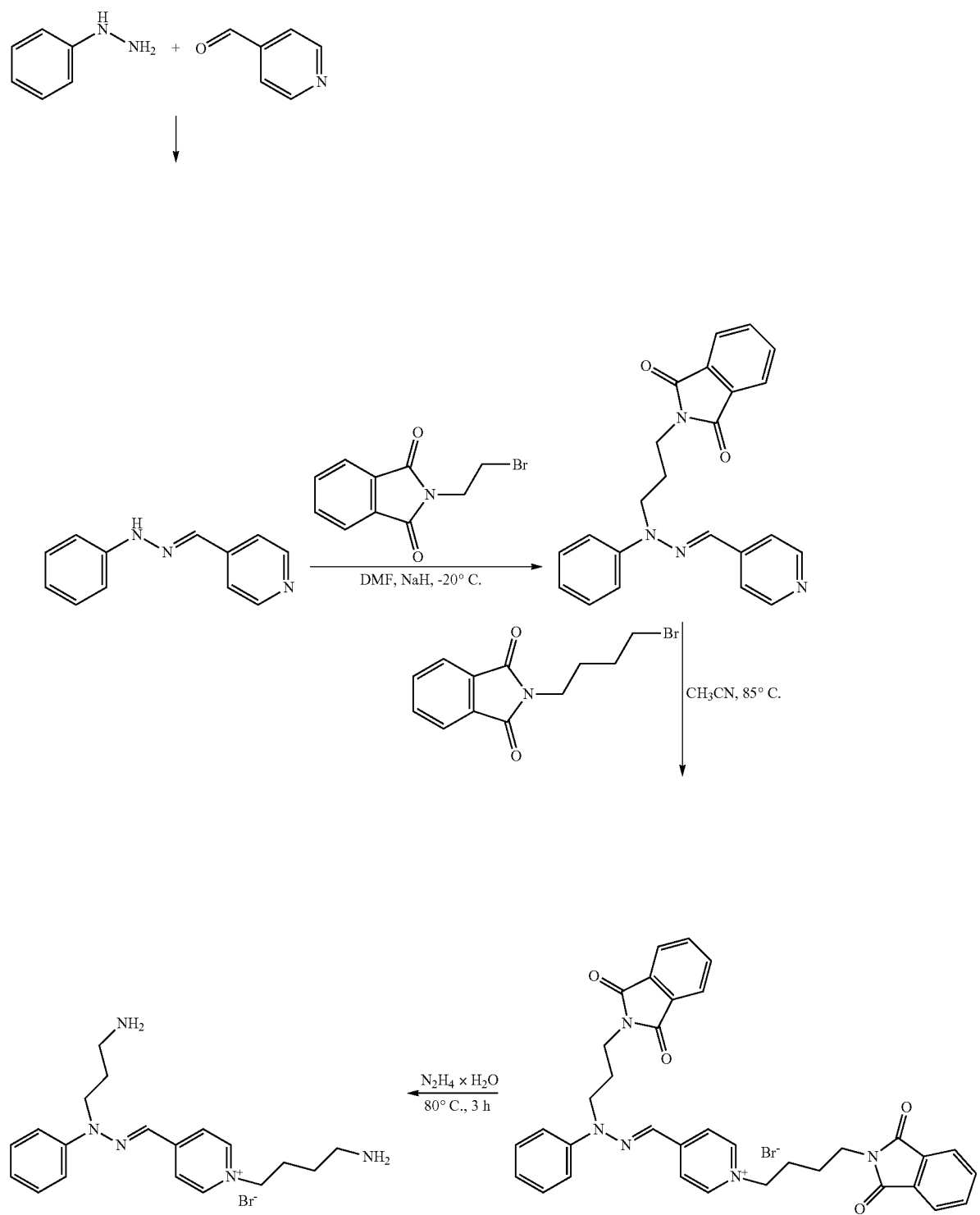

a) Step 1: 2-[3-(N-[(E)-4-pyridylmethyleneamino]anilino)propyl]isoindoline-1,3-dione

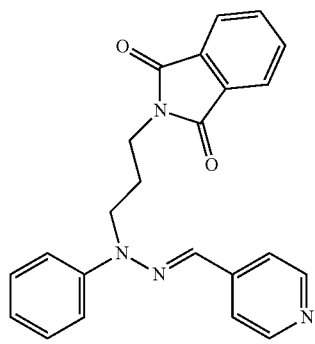

(123a)

75 g (0.38 mmol) N-[(E)-4-pyridylmethyleneamino]aniline prepared according to WO2013046041 were suspended in 450 ml N,N-dimethylformamide and stirred at 20° C. under argon atmosphere. The reaction mixture was cooled down −30° C. 27.5 g (1.13 mol) sodium hydride was added slowly while keeping the reaction temperature below −25° C. A solution of 152 g (0.565 mol) N-(3-bromopropyl)phthalimide in 500 ml DMF was added into the mixture dropwise within one hour. Afterwards, the solution was warmed to 20° C. and continued to stir for another 12 hours. The reaction mixture was quenched by adding 100 ml water and poured into 1500 ml water. Stirring was continued for one hour. The obtained precipitate was collected by filtration, washed twice with 100 ml water and dried to give a yellow solid which was used for the next step directly without further purification.

Yield: 74 g (63%).

$^1$H NMR (CDCl$_3$): δ=2.11, 3.84 and 4.01 (m; each 2H, CH$_2$), 6.98, 7.32, 7.46, 7.73, 7.85, 8.00 and 8.52 (m; totally 14H, Aryl-H and CH=N) ppm.

ESI-MS m/z 385.2 [M$^+$].

b) Step 2: 2-[4-[4-[(E)-[3-(1,3-dioxoisoindolin-2-yl)propyl-phenyl-hydrazono]-methyl]pyridin-1-ium-1-yl]butyl]isoindoline-1,3-dione bromide

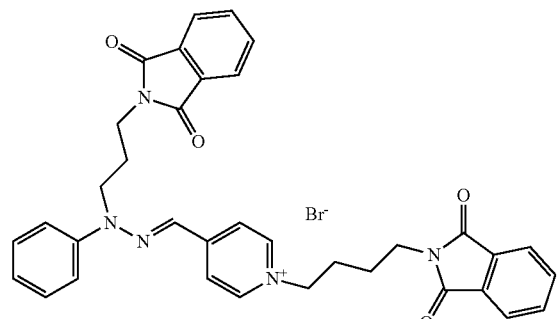

(123b)

74 g (0.193 mol) intermediate from step a) were suspended in 750 ml acetonitrile and stirred at 20° C. 114 g (0.405 mol) N-(4-brombutyl)phthalimide was added into the mixture. The product mixture was heated to reflux (85° C.) for another 24 hours. Afterwards, the reaction mixture was evaporated to dryness in vacuum. The crude product was purified by silica gel chromatography eluted with dichloromethane/methanol gradient (80:1~50:1).

Yield: 74 g (69%), yellow solid.

$^1$H NMR (DMSO-d$_6$): δ=2.04, 3.77, 4.25 and 4.91 (m; CH$_2$), 7.10, 7.40, 7.57, 7.85, 8.19, 8.91 (m; Aryl-H and CH=N) ppm.

c) Final Step 74 g (0.125 mol) intermediate from step b) were dissolved in 1200 ml ethanol and stirred at 20° C. under argon atmosphere. Within 20 minutes, 51 g (0.920 mol) hydrazine hydrate was added into the mixture dropwise. Subsequently, the reaction mixture was heated to 80° C. for 3 hours and afterwards concentrated to remove the solvent. When ⅓ of solvent was removed, lots of white solid precipitated. This precipitate was filtered-off and washed with 50 ml ethanol twice. The organic phases were combined and concentrated to obtain a crude oil. The crude oil was stirred with 250 ml dichloromethane for 30 minutes. The formed precipitate was collected by filtration, washed twice with 50 ml dichloromethane and dried at 30° C.

Yield: 27 g (60%).

$^1$H NMR (DMSO-d$_6$): δ=1.44 (m; 2H, CH$_2$), 1.85-1.97 (m; 4H, CH$_2$), 2.77 (m; 4H, CH$_2$), 4.23 (m; 2H, CH$_2$), 4.53 (m; 2H, CH$_2$), 7.13 (m; 1H, Aryl-H), 7.43 (d; 2H, Aryl-H), 7.62 (d; 2H, Aryl-H), 8.02 (m; 1H, CH=N), 8.22 (d; 2H, Aryl-H), 8.87 (d; 2H, Aryl-H) ppm.

ESI-MS m/z 326.2 [M$^+$].

Example 24: N'-[(E)-(1-hexylpyridin-1-ium-4-yl)methyleneamino]-N'-phenyl-propane-1,3-diamine bromide

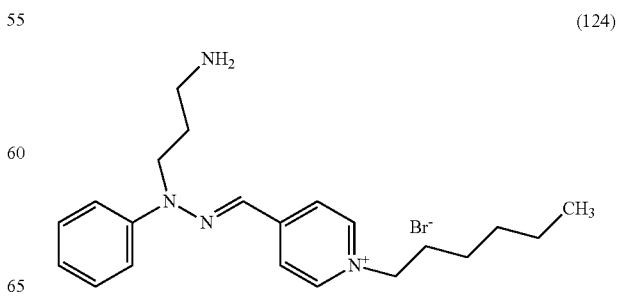

(124)

Synthesis Scheme of Example 24

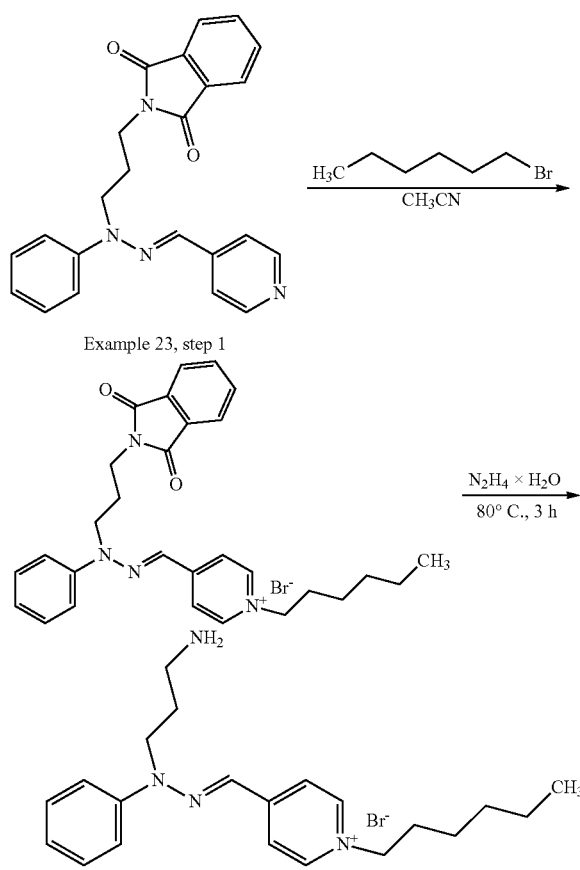

a) Step 1: 2-[3-(N-[(E)-(1-hexylpyridin-1-ium-4-yl)methyleneamino]anilino)propyl]isoindoline-1,3-dione bromide (124a)

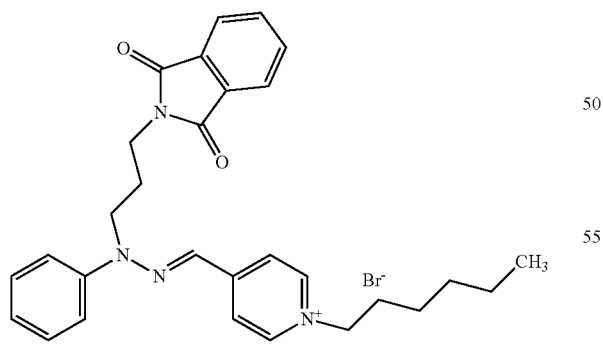

A suspension of 120 g (0.313 mol) 2-[3-(N-[(E)-4-pyridylmethyleneamino]anilino)propyl]isoindoline-1,3-dione prepared according to example 23, step 1 was stirred in 1000 ml acetonitrile at 20° C. 129 g (0.781 mol) 1-bromohexane was added into the mixture slowly. The reaction mixture was continued to stir for another 12 hours. Afterwards, the reaction mixture was concentrated to give the crude product which was purified by silica gel chromatography eluted with a dichloromethane/methanol mixture (50:1).

Yield: 134 g (78%), yellow solid.

$^1$H NMR (DMSO-$d_6$): δ=0.84 (m; Alkyl-H), 1.2-1.4 (m (br), CH$_2$), 1.9-2.2 (m (br); CH$_2$), 3.85, 4.13 and 4.76 (m, CH$_2$), 7.1 (m; Aryl-H), 7.3-7.5 (m (br); Aryl-H), 7.7-7.9 (m (br); Aryl-H), 8.07 and 9.00 (Aryl-H and CH=N) ppm.

ESI-MS m/z 469.3 [M$^+$].

b) Final Step

A mixture of 100 g (0.181 mol) 2-[3-(N-[(E)-(1-hexylpyridin-1-ium-4-yl)methyleneamino]anilino)propyl]isoindoline-1,3-dione bromide in 1000 ml ethanol was treated with 48 g (0.914 mol) hydrazine hydrate. The reaction was done according to the procedure described in example 23, final step. The final purification by precipitation was done with toluene/tetrahydrofuran (5:1) mixture.

Yield: 29 g (38%), yellow solid.

$^1$H NMR (DMSO-$d_6$): δ=0.88 (m; 3H, CH$_3$), 1.29 (m; 6H, CH$_2$), 1.73-1.88 (m; 6H, CH$_2$), 2.69 (m; 2H, CH$_2$), 4.20 (m; 2H, CH$_2$), 4.46 (m; 2H, CH$_2$), 7.12 (m; 1H, Aryl-H), 7.41 (m; 2H, Aryl-H), 7.61 (m (br); 2H, Aryl-H), 7.93 (s; 1H, CH=N), 8.16 (d; 2H, Aryl-H), 8.82 (d; 2H, Aryl-H) ppm.

ESI-MS m/z 339.3 [M$^+$].

Example 25: N'-[(E)-(1-pentylpyridin-1-ium-4-yl)methyleneamino]-N'-phenyl-propane-1,3-diamine bromide (125)

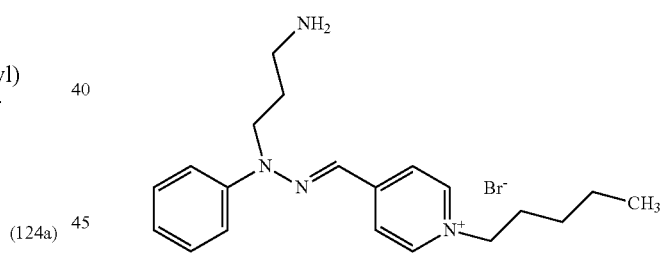

Synthesis Scheme of Example 25

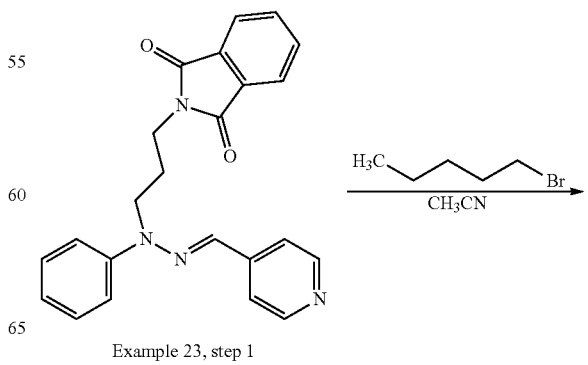

Example 23, step 1

-continued

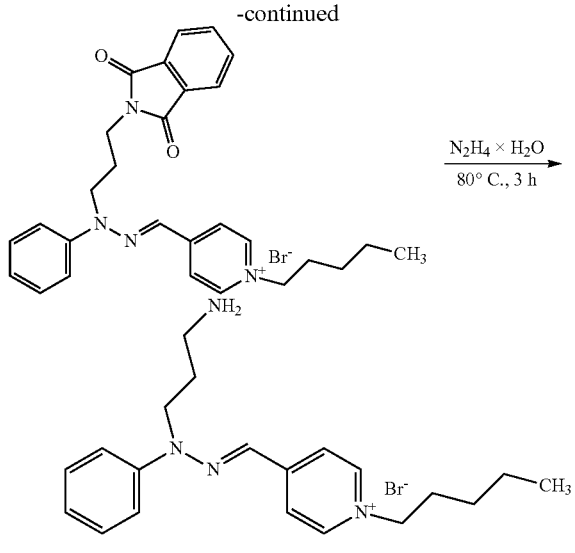

a) 2-[3-(N-[(E)-(1-pentylpyridin-1-ium-4-yl)methyl-
eneamino]anilino)propyl]isoindoline-1,3-dione bromide (125a)

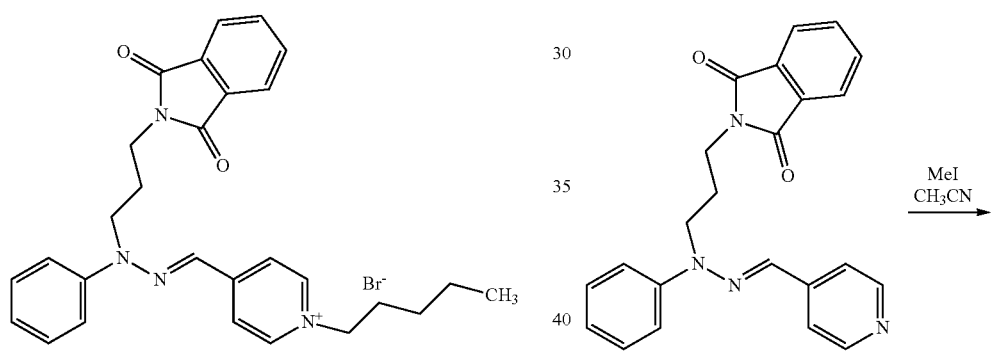

A mixture of 120 g (0.313 mol) 2-[3-(N-[(E)-4-pyridyl-methyleneamino]anilino)propyl]-isoindoline-1,3-dione and 118 g (0.781 mol) 1-bromopentane in 1000 ml acetonitrile was treated, reacted and worked-up according to the procedure given in example 24, step 1.

Yield: 138 g (80%), yellow solid.

$^1$H NMR (DMSO-$d_6$): δ=0.87 (m; Alkyl-H), 1.2-1.4 (m (br), CH$_2$), 1.9-2.2 (m (br); CH$_2$), 3.85, 4.13 and 4.79 (m, CH$_2$), 7.1 (m; Aryl-H), 7.3-7.5 (m (br); Aryl-H), 7.7-7.9 (m (br); Aryl-H), 8.1 and 9.05 (Aryl-H and CH=N) ppm.

ESI-MS m/z 455.2 [M$^+$].

b) Final Step

A mixture of 100 g (0.181 mol) 2-[3-(N-[(E)-(1-pentylpyridin-1-ium-4-yl)methyleneamino]anilino)propyl]isoindoline-1,3-dione bromide and 48 g (0.914 mol) hydrazine hydrate were treated, reacted and worked-up according to the procedure described in example 23, final step. The purification by precipitation was done with a toluene/tetrahydrofuran (5:1) mixture.

Yield: 26 g (35%), yellow solid.

$^1$H NMR (DMSO-$d_6$): δ=0.88 (m; 3H, CH$_3$), 1.33 (m; 4H, CH$_2$), 1.74 (m; 2H, CH$_2$), 1.90 (m; 2H, CH$_2$), 2.70 (m; 2H, CH$_2$), 4.19 (m; 2H, CH$_2$), 4.47 (m; 2H, CH$_2$), 7.12 (m; 1H, Aryl-H), 7.42 (m; 2H, Aryl-H), 7.62 (m (br); 2H, Aryl-H), 7.94 (s; 1H, CH=N), 8.17 (d; 2H, Aryl-H), 8.83 (d; 2H, Aryl-H) ppm.

ESI-MS m/z 325.2 [M$^+$].

Example 26: N'-[(E)-(1-methylpyridin-1-ium-4-yl)methyleneamino]-N'-phenyl-propane-1,3-diamine iodide (126)

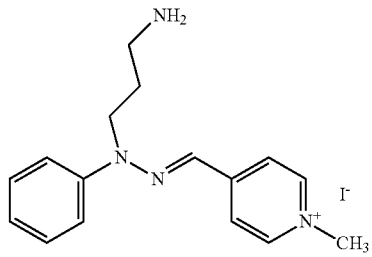

Synthesis Scheme of Example 26

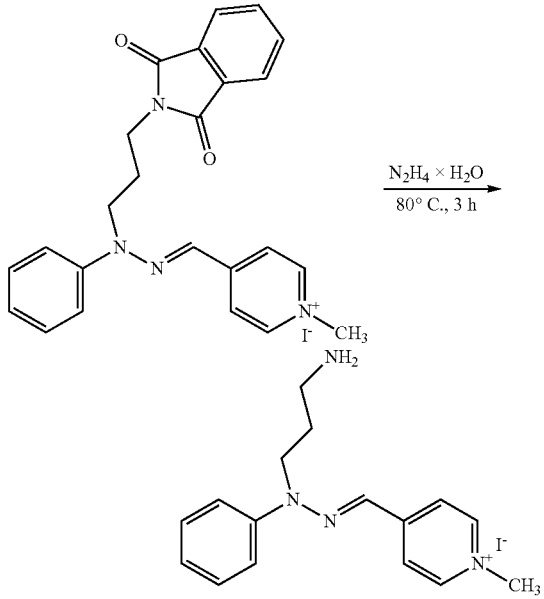

Example 23, step 1 a) Step 1: 2-[3-(N-[(E)-(1-methylpyridin-1-ium-4-yl)methyleneamino]anilino)propyl]isoindoline-1,3-dione iodide

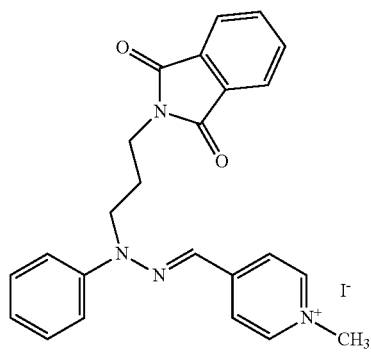

(126a)

A mixture of 120 g (0.313 mol) 2-[3-(N-[(E)-4-pyridyl-methyleneamino]anilino)propyl]-isoindoline-1,3-dione and 111 g (0.781 mol) methyl iodide in 1000 ml acetonitrile was treated, reacted and worked-up according to the procedure given in example 24, step 1. Column chromatography was done with a dichloromethane/methanol mixture (50:1).

Yield: 124 g (75%), yellow solid.

$^1$H NMR (DMSO-d$_6$): δ=2.1 (m (br), CH$_2$), 3.87 and 4.14 (m; CH$_2$), 4.51 (s; CH$_3$), 7.1 (m; Aryl-H), 7.2-7.4 (m (br); Aryl-H), 7.8-8.0 (m (br); Aryl-H), 8.06 and 8.90 (Aryl-H and CH=N) ppm.

ESI-MS m/z 399.2 [M$^+$].

b) Final Step

A reaction mixture of 86 g (0.183 mol) 2-[3-(N-[(E)-(1-methylpyridin-1-ium-4-yl)methyleneamino]anilino)propyl] isoindoline-1,3-dione iodide and 48 g (0.914 mol) hydrazine hydrate was treated, reacted and worked-up according to the procedure described in example 23, final step. The purification by precipitation was done with toluene/tetrahydrofuran (5:1) mixture.

Yield: 22 g (30%), yellow solid.

$^1$H NMR (DMSO-d$_6$): δ=1.83 (m; 2H, CH$_2$), 2.85 (m; 2H, CH$_2$), 4.24 (m; 5H, CH$_3$+CH$_2$), 5.34 (d (br); 2H, CH$_2$), 7.12 (m; 1H, Aryl-H), 7.44 (m; 2H, Aryl-H), 7.62 (m; 2H, Aryl-H), 7.95 (s; 1H, CH=N), 8.16 (d; 2H, Aryl-H), 8.74 (d; 2H, Aryl-H) ppm.

ESI-MS m/z 269.2 [M$^+$].

Example 27: N'-[(E)-(1-methylpyridin-1-ium-4-yl)methyleneamino]-N'-phenyl-pentane-1,5-diamine iodide

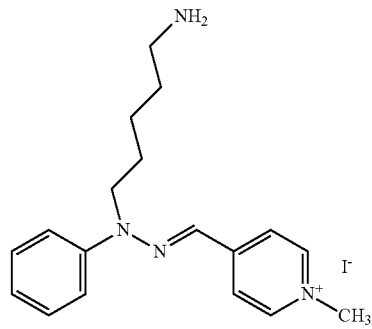

(127)

Synthesis Scheme of Example 27

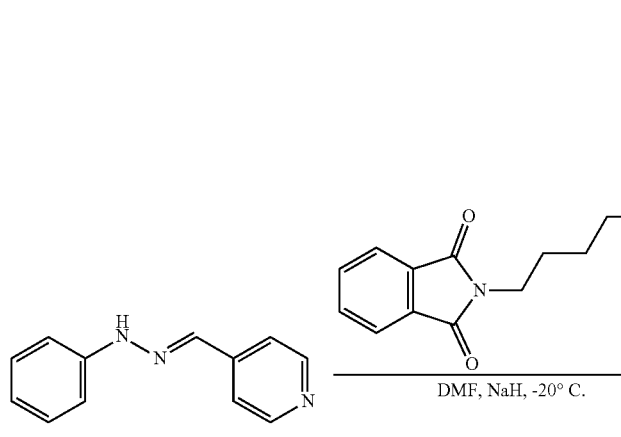

-continued

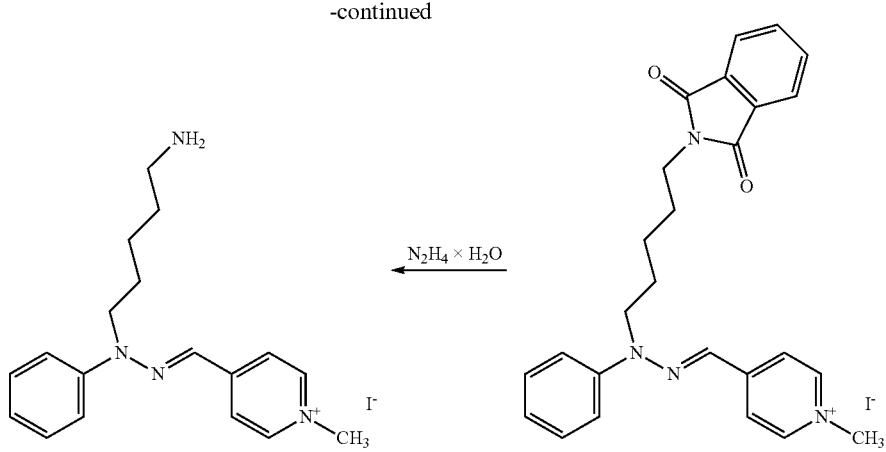

a) Step 1: 2-[5-(N-[(E)-4-pyridylmethyleneamino]anilino)pentyl]isoindoline-1,3-dione b) 2-[5-(N-[(E)-(1-methylpyridin-1-ium-4-yl)methyleneamino]anilino)pentyl]isoindoline-1,3-dione iodide

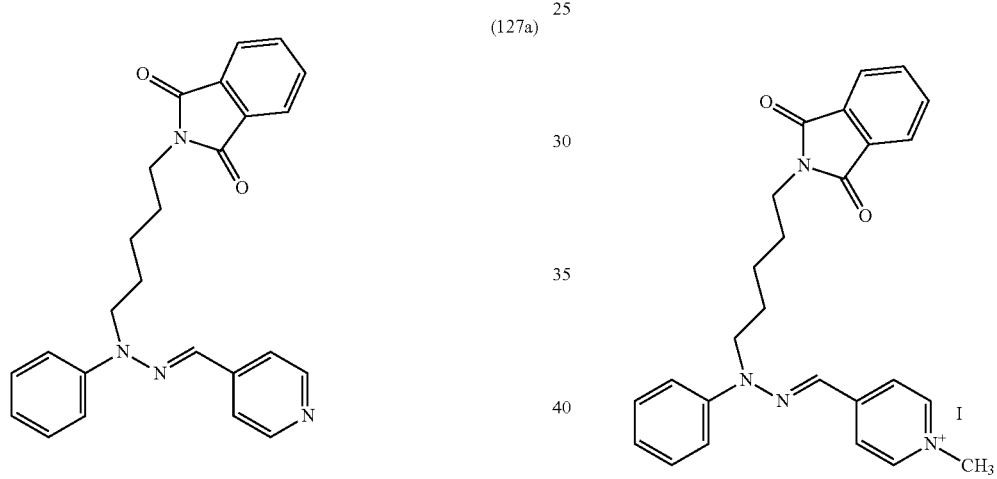

60 g (0.302 mol) N-[(E)-4-pyridylmethyleneamino]aniline in 350 ml N,N-dimethylformamide were stirred at 20° C. under argon atmosphere. The reaction mixture was cooled down −30° C. 22 g (0.903 mol) sodium hydride was added slowly while keeping the reaction temperature below −25° C. Afterwards, a solution of 121 g (0.452 mol) N-(5-bromopentyl)phthalimide in 500 ml N,N-dimethylformamide was added into the mixture dropwise within one hour. After the addition, the product mixture was warmed to 20° C. and continued to stir for another 12 hours. Then, the reaction was quenched by adding 20 ml water. Another 600 ml water were poured into the reaction mixture. The formed precipitate was collected by filtration and washed with distilled water. The obtained crude product was used for the next step directly without further purification.

Yield: 88 g (75%), yellow solid.

ESI-MS m/z 412.2 [M+].

71 g (0.183 mol) crude 2-[5-(N-[(E)-4-pyridylmethyleneamino]anilino)pentyl]isoindoline-1,3-dione were suspended in 500 ml dichloromethane and stirred at 20° C. 54.5 g (0.384 mol) methyl iodide were added into the mixture slowly. The solution was continued to stir at 20° C. for another 12 hours. Afterwards, the reaction mixture was evaporated to dryness in vacuum. The crude product was purified by silica gel chromatography eluted with a dichloromethane/methanol gradient (50:1~20:1).

Yield: 74 g (69%), yellow solid.

$^1$H NMR (DMSO-$d_6$): δ=1.50, 1.67, 1.87 (m; $CH_2$), 3.28 and 4.13 (m; $CH_2$), 4.23 (s; $CH_3$), 7.12 (m; Aryl-H), 7.42 (m; Aryl-H), 7.56 (m; Aryl-H), 7.88 (m; Aryl-H), 8.17 (m; Aryl-H), 8.4-8.6 (m (br); Aryl-H and CH=N), 8.75 (m; Aryl-H) ppm.

c) Final Step 70 g (0.165 mol) 2-[5-(N-[(E)-(1-methylpyridin-1-ium-4-yl)methyleneamino]anilino)pentyl]isoindoline-1,3-dione iodide was dissolved in 1000 ml ethanol and stirred at 20° C. under argon atmosphere. 47 g (0.827 mol) hydrazine hydrate were added into the mixture dropwise within 20 minutes. The reaction mixture was heated to 80° C. and stirred at this temperature for three hours. Afterwards, the reaction mixture was cooled down to 20° C. The formed precipitate was collected and washed with ethanol. The combined organic phases were evaporated in vacuum to yield an oily raw product. This crude oil was taken up with 1000 ml of toluene/tetrahydrofuran mixture (5:1). Again, the formed precipitate was filtered-off and washed with the used toluene/tetrahydrofuran mixture. This crystallization was repeated twice.

Yield: 21 g (55%), yellow solid.

$^1$H NMR (D$_2$O): δ=1.45 (m; 4H, CH$_2$), 1.68 (m; 2H, CH$_2$), 2.95 (t; 2H, CH$_2$), 3.71 (m; 2H, CH$_2$), 3.96 (s; 3H, CH$_3$), 6.81 (m; 1H, Aryl-H), 6.82 (m; 3H, Aryl-H+CH=N), 7.25 (m; 2H, Aryl-H), 7.59 (m; 2H, Aryl-H), 8.10 (s; 2H, Aryl-H) ppm.

ESI-MS m/z 297.2 [M$^+$].

B. APPLICATION EXAMPLES

A 0.5% solution of the dye adjusted to pH 10 with ammonia is mixed with the same weight of 6% hydrogen peroxide solution.

This mixture is applied with a brush on two hair strands (Piedmont white hair from international Hair Importers). After 30 min. at room temperature the tresses are rinsed, shampooed, rinsed and dried.

To determine the wash fastness one dyed tress is washed with a commercial shampoo using approx. 0.5 g shampoo for each tress under tap water (water temperature: 37° C.+/−1° C.; flow rate 5-6 l/min). Finally the tress is rinsed under tap water, pressed out with a paper towel, combed and dried with a hair dryer or at room temperature. This procedure is repeated 24 times.

The results are summarized in the following table:

| Color | dE washing fastness 24 × washed with shampoo | Example |
|---|---|---|
| Red | 4.5 | 1 |
| Red | 9.3 | 2 |
| Red | 6.2 | 3 |
| Red | 2.7 | 4 |
| Red | 4.6 | 6 |
| Red | 3.6 | 7 |
| Red | 3.8 | 8 |
| Blue | 5.2 | 13 |
| Violet | 2.0 | 16 |
| Yellow | 2.8 | 17 |

The invention claimed is:

1. Compounds of formula

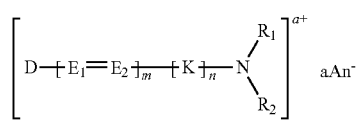

(1)

wherein
D is a cationic heteroaromatic group having a

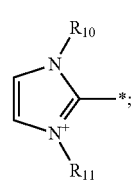

formula (1a)

K is an aromatic or group;
R$_1$ and R$_2$ independently from each other are hydrogen; C$_1$-C$_{12}$alkyl; C$_1$-C$_{12}$alkyl, which is substituted by hydroxy; amino-C$_6$-C$_{10}$aryl; N(R$_6$R$_7$)—C$_1$-C$_8$alkyl; N(R$_6$R$_7$)—C$_1$-C$_{12}$alkyl, which is substituted by hydroxy or interrupted by —NR$_9$—; C$_6$-C$_{10}$aryl; or
R$_6$, R$_7$ and R$_9$, independently from each other are hydrogen; C$_1$-C$_5$alkyl; amino-C$_1$-C$_5$alkyl; C$_1$-C$_5$alkylamino-C$_1$-C$_5$alkyl; or di-C$_1$-C$_5$alkylamino-C$_1$-C$_5$alkyl;
R$_{10}$ and R$_{11}$ independently from each other are hydrogen; C$_1$-C$_{12}$alkyl; N(R$_{13}$R$_{14}$)—C$_1$-C$_{12}$alkyl; N(R$_{13}$R$_{14}$)—C$_1$-C$_{12}$alkyl which is interrupted by phenylene; N$^+$(R$_{13}$R$_{14}$R$_{15}$)—C$_1$-C$_{12}$alkyl which is interrupted by phenylene;
R$_{13}$, R$_{14}$, R$_{15}$ independently from each other are hydrogen; C$_1$-C$_5$alkyl; amino-C$_1$-C$_5$alkyl; C$_1$-C$_5$alkylamino-C$_1$-C$_5$alkyl; or di-C$_1$-C$_5$alkylamino-C$_1$-C$_5$alkyl;
E$_1$ and E$_2$ independently from each other are =N—;
An is an anion
a is a number from 1 to 3;
m and n are 1;
wherein for group D, at least one of the radicals R$_1$, R$_2$, R$_{10}$, and R$_{11}$ is substituted by radical comprising at least one amino group.

2. Compounds according to claim 1, wherein D in formula (1a)
R$_{10}$ and R$_{11}$ independently from each other are C$_1$-C$_{12}$alkyl; amino-C$_1$-C$_{12}$alkyl; di-C$_1$-C$_5$alkylamino-C$_1$-C$_{12}$alkyl; or N$^+$(R$_3$R$_4$R$_5$)—C$_1$-C$_{12}$alkyl.

3. Compounds according to claim 1, which correspond to formula

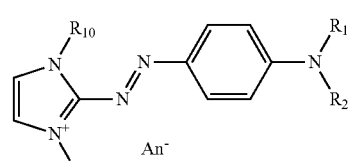

(2)

wherein
R$_1$ and R$_2$ independently from each other are hydrogen; C$_1$-C$_{12}$alkyl; C$_1$-C$_{12}$alkyl, which is substituted by hydroxy; amino-C$_6$-C$_{10}$aryl; N(R$_6$R$_7$)—C$_1$-C$_8$alkyl; N(R$_6$R$_7$)—C$_1$-C$_8$alkyl, which is interrupted by —NR$_9$—;
R$_{10}$ and R$_{11}$ independently from each other are C$_1$-C$_{12}$alkyl; C$_1$-C$_{12}$alkyl which is substituted by hydroxy or interrupted by phenylene; amino-C$_1$-C$_{12}$alkyl; di-C$_1$-C$_5$alkyl-amino-C$_1$-C$_{12}$alkyl; or N$^+$(R$_3$R$_4$R$_5$)—C$_1$-C$_{12}$alkyl;
An is an anion; and
R$_3$, R$_4$, R$_5$, R$_6$, R$_7$, and R$_9$ independently from each other are hydrogen; C$_1$-C$_5$alkyl; amino-C$_1$-C$_5$alkyl; C$_1$-C$_5$alkylamino-C$_1$-C$_5$alkyl; or di-C$_1$-C$_5$alkylamino-C$_1$-C$_5$alkyl.

4. Compounds according to claim 1, wherein $R_1$ and $R_2$ independently from each other are $C_1$-$C_{12}$alkyl;

$R_6$, $R_7$, $R_5$, independently from each other are hydrogen; or $C_1$-$C_6$alkyl; and $R_{10}$ and $R_{11}$ independently from each other are $C_1$-$C_{12}$alkyl; or $N^+(R_3R_4R_5)$—$C_1$-$C_{12}$alkyl; and $R_3$, $R_4$ and $R_5$ independently from each other are hydrogen; or $C_1$-$C_5$alkyl.

5. Compounds according to claim 1, wherein $R_1$ and $R_2$ are hydrogen; or $C_1$-$C_5$alkyl;

$R_6$, $R_7$, $R_5$, independently from each other are hydrogen; or $C_1$-$C_5$alkyl; and $R_{10}$ and $R_{11}$ are $C_1$-$C_5$alkyl; or $N^+(R_{13}R_{14}R_{15})$—$C_1$-$C_5$alkyl; or $N(R_{13}R_{14})$—$C_1$-$C_5$alkyl; and $R_3$ and $R_4$ independently from each other are hydrogen; or $C_1$-$C_5$alkyl.

6. Compounds according to claim 1, wherein $R_1$ and $R_2$ independently from each other are $C_1$-$C_{12}$alkyl; and $R_{11}$ and $R_{12}$ independently from each other are $C_1$-$C_5$alkyl; or amino-$C_1$-$C_5$alkyl.

7. A compound selected from the group consisting of:

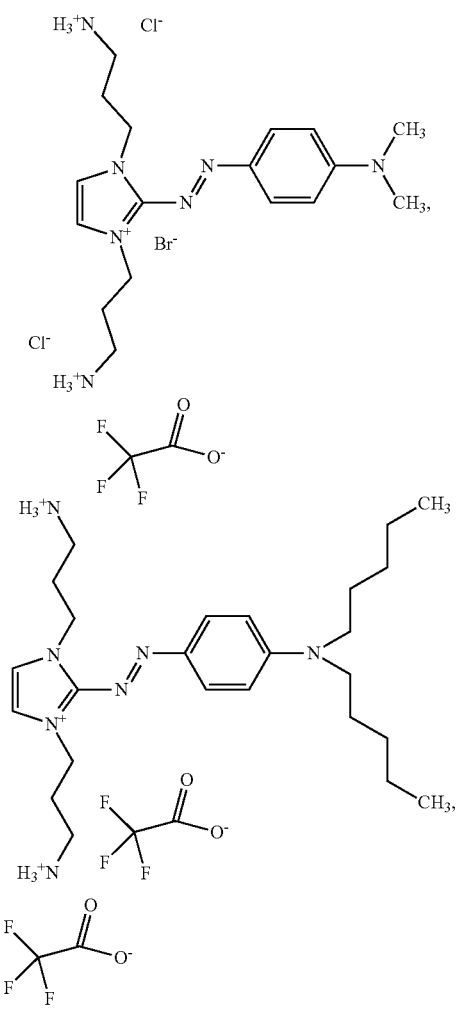

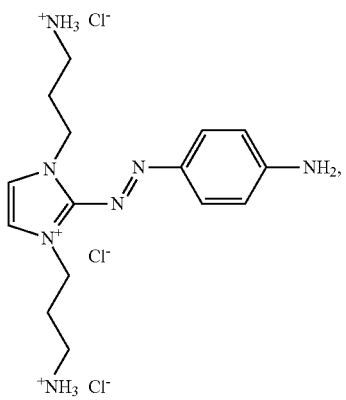

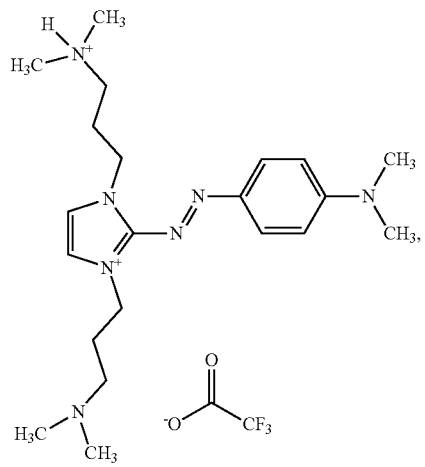

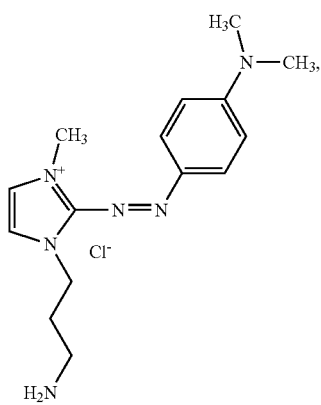

105
-continued
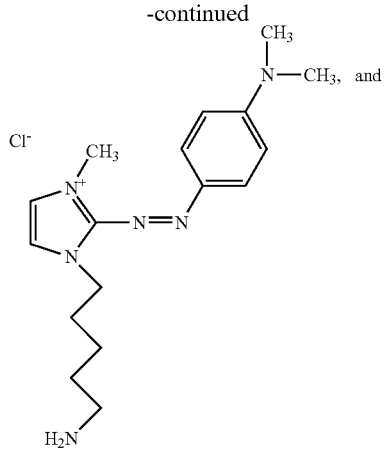
and
106
-continued
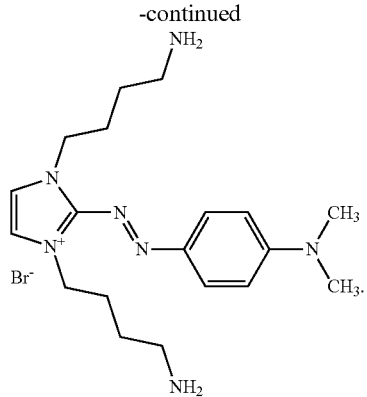
* * * * *